US009505735B2

(12) United States Patent
McLellan et al.

(10) Patent No.: US 9,505,735 B2
(45) Date of Patent: Nov. 29, 2016

(54) COMPOUNDS FOR TREATING INFECTIOUS DISEASES

(71) Applicants: Whitehead Institute for Biomedical Research, Cambridge, MA (US); The General Hospital Corporation, Boston, MA (US)

(72) Inventors: Catherine McLellan, Somerville, MA (US); Ralph Mazitschek, Belmont, MA (US); Luke Whitesell, Somerville, MA (US); Susan L. Lindquist, Cambridge, MA (US)

(73) Assignees: Whitehead Institute for Biomedical Research, Cambridge, MA (US); The General Hospital Corporation, Boston, MA (US)

( * ) Notice: Subject to any disclaimer, the term of this patent is extended or adjusted under 35 U.S.C. 154(b) by 0 days.

(21) Appl. No.: 14/408,605

(22) PCT Filed: Jun. 21, 2013

(86) PCT No.: PCT/US2013/047035
§ 371 (c)(1),
(2) Date: Dec. 17, 2014

(87) PCT Pub. No.: WO2013/192517
PCT Pub. Date: Dec. 27, 2013

(65) Prior Publication Data
US 2015/0284356 A1    Oct. 8, 2015

Related U.S. Application Data

(60) Provisional application No. 61/798,834, filed on Mar. 15, 2013, provisional application No. 61/662,755, filed on Jun. 21, 2012.

(51) Int. Cl.
| | | |
|---|---|---|
| C07D 213/643 | (2006.01) | |
| C07D 263/56 | (2006.01) | |
| C07D 277/64 | (2006.01) | |
| A61K 31/44 | (2006.01) | |
| A61K 31/167 | (2006.01) | |
| A61K 31/428 | (2006.01) | |
| C07D 311/08 | (2006.01) | |
| A61K 45/06 | (2006.01) | |
| C07D 213/75 | (2006.01) | |
| C07D 311/16 | (2006.01) | |
| C07D 263/58 | (2006.01) | |
| C07D 277/82 | (2006.01) | |
| C07C 235/24 | (2006.01) | |
| C07C 235/38 | (2006.01) | |
| C07C 233/29 | (2006.01) | |
| C07D 263/57 | (2006.01) | |

(52) U.S. Cl.
CPC ............ *C07D 311/08* (2013.01); *A61K 45/06* (2013.01); *C07C 233/29* (2013.01); *C07C 235/24* (2013.01); *C07C 235/38* (2013.01); *C07D 213/643* (2013.01); *C07D 213/75* (2013.01); *C07D 263/57* (2013.01); *C07D 263/58* (2013.01); *C07D 277/64* (2013.01); *C07D 277/82* (2013.01); *C07D 311/16* (2013.01)

(58) Field of Classification Search
None
See application file for complete search history.

(56) References Cited

U.S. PATENT DOCUMENTS

| | | | | |
|---|---|---|---|---|
| 5,583,147 A | * | 12/1996 | Ko ...................... | C07D 213/75 514/255.05 |
| 7,605,158 B2 | * | 10/2009 | Kawaguchi .......... | C07D 405/14 514/233.5 |
| 2010/0022547 A1 | | 1/2010 | Hedstrom et al. | |
| 2011/0195999 A1 | | 8/2011 | Nakamoto et al. | |

FOREIGN PATENT DOCUMENTS

| | | |
|---|---|---|
| JP | S61-126071 A | 6/1986 |
| JP | H11-222431 A | 8/1999 |
| WO | WO 2004/048567 A2 | 6/2004 |
| WO | WO 2010/111653 A2 | 9/2010 |
| WO | WO 2010/111713 A2 | 9/2010 |
| WO | WO 2013/163404 A1 | 10/2013 |

OTHER PUBLICATIONS

International Search Report and Written Opinion for Application No. PCT/US2013/047035, mailed Dec. 19, 2013.
International Preliminary Report on Patentability for Application No. PCT/US2013/047035, mailed Dec. 31, 2014.
[No Author Listed], CHEMCATS Compound RN 1002071-75-1. STN on the Web. Feb. 8, 2008. 1 page.
[No Author Listed], CHEMCATS Compound RN 1329243-62-0. STN on the Web. Sep. 7, 2011. 1 page.

(Continued)

*Primary Examiner* — Zinna Northington Davis
(74) *Attorney, Agent, or Firm* — Wolf, Greenfield & Sacks, P.C.

(57) ABSTRACT

The present invention provides compounds of Formula I, pharmaceutically acceptable salts thereof, and pharmaceutical compositions thereof. Compounds of the present invention are useful for inhibiting fungal or parasitic growth. The compounds are useful as inhibitors of glycosylphosphatidylinositol (GPI)-anchor biosynthesis, in particular, as inhibitors of fungal Gwt1 activity. The present invention further provides methods of using the compounds described herein for treating fungal or parasitic infections. The compounds can also be used as biological probes to study the effects of inhibiting Gwt1 activity.

38 Claims, 23 Drawing Sheets

(56) References Cited

OTHER PUBLICATIONS

[No Author Listed], CHEMCATS Compound RN 1331089-50-9. STN on the Web. Sep. 11, 2011. 1 page.
[No Author Listed], CHEMCATS Compound RN 303226-63-3. STN on the Web. Nov. 20, 2000. 1 page.
[No Author Listed], CHEMCATS Compound RN 522606-00-4. STN on the Web. May 30, 2003. 1 page.
Alberti et al., A suite of Gateway cloning vectors for high-throughput genetic analysis in *Saccharomyces cerevisiae*. Yeast. Oct. 2007;24(10):913-9.
Berge et al., Pharmaceutical salts. J Pharm Sci. Jan. 1977;66(1):1-19.
Bryant et al., Vacuole biogenesis in *Saccharomyces cerevisiae*: protein transport pathways to the yeast vacuole. Microbiol Mol Biol Rev. Mar. 1998;62(1):230-47. Review.
Castillon et al., The yeast p24 complex regulates GPI-anchored protein transport and quality control by monitoring anchor remodeling. Mol Biol Cell. Aug. 15, 2011;22(16):2924-36. Doi: 10.1091/mbc.E11-Apr. 0294. Epub Jun. 16, 2011.
Cowen et al., Evolution of drug resistance in Candida albicans. Annu Rev Microbiol. 2002;56:139-65. Epub Jan. 30, 2002. Review.
Cox et al., Transcriptional induction of genes encoding endoplasmic reticulum resident proteins requires a transmembrane protein kinase. Cell. Jun. 18, 1993;73(6):1197-206.
Depristo et al., A framework for variation discovery and genotyping using next-generation DNA sequencing data Nat Genet. May 2011;43(5):491-8. Doi: 10.1038/ng.806. Epub Nov. 1, 2011. 19 pages.
Fankhauser et al., Purification, biosynthesis and cellular localization of a major 125-kDa glycophosphatidylinositol-anchored membrane glycoprotein of *Saccharomyces cerevisiae*. Eur J Biochem. Jan. 30, 1991;195(2):439-48.
Fonzi et al., Isogenic strain construction and gene mapping in Candida albicans. Genetics. Jul. 1993;134(3):717-28.
Fujita et al., Inositol deacylation by Bst1p is required for the quality control of glycosylphosphatidylinositol-anchored proteins. Mol Biol Cell. Feb. 2006;17(2):834-50. Epub Nov. 30, 2005.
Giaever et al., Functional profiling of the *Saccharomyces cerevisiae* genome. Nature. Jul. 25, 2002;418(6896):387-91.
Gillum et al., Isolation of the Candida albicans gene for orotidine-5'-phosphate decarboxylase by complementation of *S. cerevisiae* ura3 and *E. coli* pyrF mutations. Mol Gen Genet. 1984;198(1):179-82.
Hata et al., Efficacy of oral E1210, a new broad-spectrum antifungal with a novel mechanism of action, in murine models of candidiasis, aspergillosis, and fusariosis. Antimicrob Agents Chemother. Oct. 2011;55(10):4543-51. Doi: 10.1128/AAC.00366-11. Epub Jul. 25, 2011.
Heckman et al., Molecular evidence for the early colonization of land by fungi and plants. Science. Aug. 10, 2001;293(5532):1129-33.
Heifetz et al., Mechanism of action of tunicamycin on the UDP-GlcNAc:dolichyl-phosphate Glc-Nac-1-phosphate transferase. Biochem. May 29, 1979;18(11):2186-92.
Hoon et al., An integrated platform of genomic assays reveals small-molecule bioactivities. Nat Chem Biol. Aug. 2008;4(8):498-506. Doi: 10.1038/nchembio.100. Epub Jul. 11, 2008. Erratum in: Nat Chem Biol. Oct. 2008;4(10):632.
Hu et al., Approaching a complete repository of sequence-verified protein-encoding clones for *Saccharomyces cerevisiae*. Genome Res. Apr. 2007;17(4):536-43. Epub Feb. 23, 2007.
Huh et al., Global analysis of protein localization in budding yeast. Nature. Oct. 16, 2003;425(6959):686-91.
Khan et al., Studies on haloaromatics and haloheterocyclics. Part I. Synthesis of some new haloaromatics from aryloxy acetic acids as possible fungicides. Agr Biol Chem. 1976;40(12):2481-3. Abstract. 2 pages.
Klis et al., Covalently linked cell wall proteins of Candida albicans and their role in fitness and virulence. FEMS Yeast Res. Oct. 2009;9(7):1013-28. Doi: 10.1111/j.1567-1364.2009.00541.x. Epub Jun. 22, 2009. Review.
Li et al., Fast and accurate short read alignment with Burrows-Wheeler transform. Bioinformatics. Jul. 15, 2009;25(14):1754-60. Doi: 10.1093/bioinformatics/btp324. Epub May 18, 2009.
Li et al., The Sequence Alignment/Map format and SAMtools. Bioinformatics. Aug. 15, 2009;25(16):2078-9. Doi: 10.1093/bioinformatics/btp352. Epub Jun. 8, 2009.
Liu et al., Suppression of hyphal formation in Candida albicans by mutation of a STE12 homolog. Science. Dec. 9, 1994;266(5191):1723-6. Erratum in: Science Jan. 6, 1995;267(5194):17.
Ma et al., The unfolding tale of the unfolded protein response. Cell. Dec. 28, 2001;107(7):827-30. Review.
Miyazaki et al., In vitro activity of E1210, a novel antifungal, against clinically important yeasts and molds. Antimicrob Agents Chemother. Oct. 2011;55(10):4652-8. Doi: 10.1128/AAC.00291-11. Epub Aug. 8, 2011.
Monk et al., Outwitting multidrug resistance to antifungals. Science. Jul. 18, 2008;321(5887):367-9. Doi: 10.1126/science.1159746.
Murakami et al., PIG-W is critical for inositol acylation but not for flipping of glycosylphosphatidylinositol-anchor. Mol Biol Cell. Oct. 2003;14(10):4285-95. Epub Jun. 13, 2003.
Nakamoto et al., Synthesis and evaluation of novel antifungal agents-quinoline and pyridine amide derivatives. Bioorg Med Chem Lett. Aug. 1, 2010;20(15):4624-6. Doi: 10.1016/j.bmcl.2010.06.005. Epub Jun. 8, 2010.
Noble et al., Systematic screens of a Candida albicans homozygous deletion library decouple morphogenetic switching and pathogenicity. Nat Genet. Jul. 2010;42(7):590-8. Doi: 10.1038/ng.605. Epub Jun. 13, 2010.
Orlean et al., Thematic review series: lipid posttranslational modifications. GPI anchoring of protein in yeast and mammalian cells, or: how we learned to stop worrying and love glycophospholipids. J Lipid Res. May 2007;48(5):993-1011. Epub Mar. 14, 2007. Review.
Ostrosky-Zeichner et al., An insight into the antifungal pipeline: selected new molecules and beyond. Nat Rev Drug Discov. Sep. 2010;9(9):719-27. Doi: 10.1038/nrd3074. Epub Aug. 20, 2010. Review.
Pfaller et al., Epidemiology of invasive candidiasis: a persistent public health problem. Clin Microbiol Rev. Jan. 2007;20(1):133-63. Review.
Pollard et al., Ero1p: a novel and ubiquitous protein with an essential role in oxidative protein folding in the endoplasmic reticulum. Mol Cell. Jan. 1998;1(2):171-82.
Poulain et al., Candida albicans cell wall glycans, host receptors and responses: elements for a decisive crosstalk. Curr Opin Microbiol. Aug. 2004;7(4):342-9. Review.
Richard et al., GPI7 affects cell-wall protein anchorage in *Saccharomyces cerevisiae* and Candida albicans. Microbiology. Jul. 2002;148(Pt 7):2125-33.
Sagane et al., Analysis of membrane topology and identification of essential residues for the yeast endoplasmic reticulum inositol acyltransferase Gwt1p. J Biol Chem. Apr. 22, 2011;286(16):14649-58. Doi: 10.1074/jbc.M110.193490. Epub Mar. 2, 2011.
Shapiro et al., Regulatory circuitry governing fungal development, drug resistance, and disease. Microbiol Mol Biol Rev. Jun. 2011;75(2):213-67. Doi: 10.1128/MMBR.00045-10. Review.
Shen et al., The Candida albicans pescadillo homolog is required for normal hypha-to-yeast morphogenesis and yeast proliferation. Proc Natl Acad Sci U S A. Dec. 30, 2008;105(52):20918-23. Doi: 10.1073/pnas.0809147105. Epub Dec. 15, 2008.
Smyth, Linear models and empirical bayes methods for assessing differential expression in microarray experiments. Stat Appl Genet Mol Biol. 2004;3:Article3. Epub Feb. 12, 2004. 26 pages.
Strating et al., The p24 family and selective transport processes at the ER-Golgi interface. Biol Cell. Sep. 2009;101(9):495-509. Doi: 10.1042/BC20080233. Review.
Sudbery, Growth of Candida albicans hyphae. Nat Rev Microbiol. Aug. 16, 2011;9(10):737-48. Doi: 10.1038/nrmicro2636. Review.

(56) References Cited

OTHER PUBLICATIONS

Tsukahara et al., Medicinal genetics approach towards identifying the molecular target of a novel inhibitor of fungal cell wall assembly. Mol Microbiol. May 2003;48(4):1029-42.

Umemura et al., GWT1 gene is required for inositol acylation of glycosylphosphatidylinositol anchors in yeast. J Biol Chem. Jun. 27, 2003;278(26):23639-47. Epub Apr. 24, 2003.

Walter et al., The unfolded protein response: from stress pathway to homeostatic regulation. Science. Nov. 25, 2011;334(6059):1081-6. Doi: 10.1126/science.1209038. Review.

Watanabe et al., E1210, a new broad-spectrum antifungal, suppresses Candida albicans hyphal growth through inhibition of glycosylphosphatidylinositol biosynthesis. Antimicrob Agents Chemother. Feb. 2012;56(2):960-71. Doi: 10.1128/AAC.00731-11. Epub Dec. 5, 2011.

Wheeler et al., A drug-sensitive genetic network masks fungi from the immune system. PloS Pathog. Apr. 2006;2(4):e35. Epub Apr. 28, 2006. 12 pages.

Wheeler et al., Dynamic, morphotype-specific Candida albicans beta-glucan exposure during infection and drug treatment. PloS Pathog. Dec. 2008;4(12):e1000227. Doi: 10.1371/journal.ppat.1000227. Epub Dec. 5, 2008. 12 pages.

White et al., Stable azole drug resistance associated with a substrain of Candida albicans from an HIV-infected patient. Oral Dis. May 1997;3 Suppl 1:S102-9.

White, Increased mRNA levels of ERG16, CDR, and MDR1 correlate with increases in azole resistance in Candida albicans isolates from a patient infected with human immunodeficiency virus. Antimicrob Agents Chemother. Jul. 1997;41(7):1482-7.

White, The presence of an R467K amino acid substitution and loss of allelic variation correlate with an azole-resistant lanosterol 14alpha demethylase in Candida albicans. Antimicrob Agents Chemother. Jul. 1997;41(7):1488-94.

Wilen et al., Strategies in optical resolutions. Tetrahedron. 1977;33(21):2725-36.

* cited by examiner

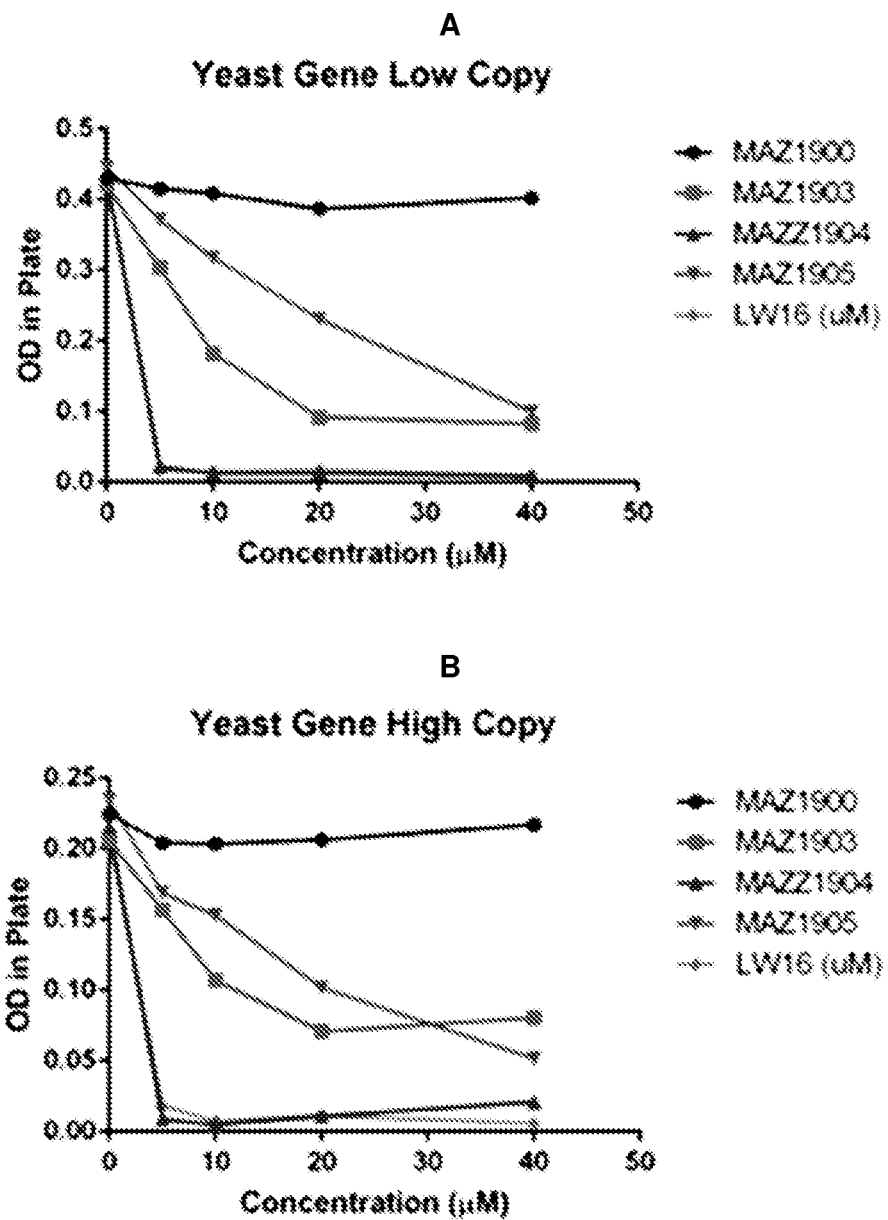
Figure 22A-B

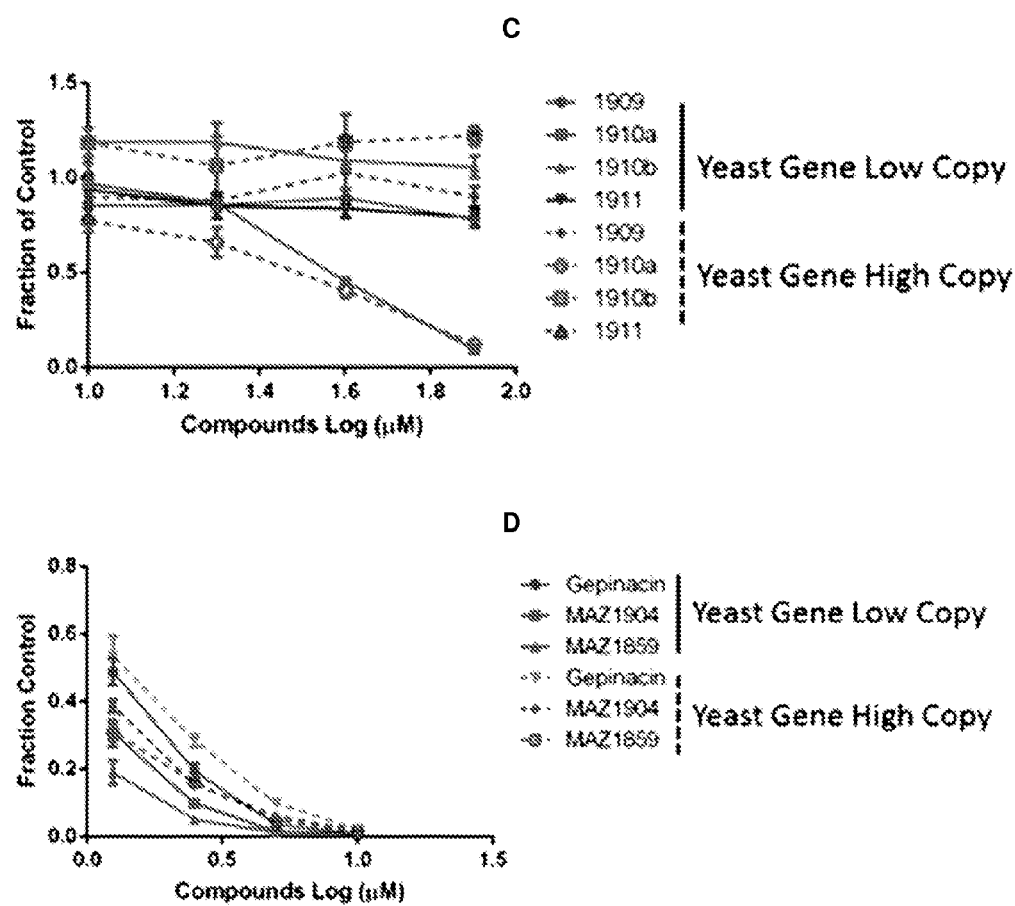
Figure 22C-D

COMPOUNDS FOR TREATING INFECTIOUS DISEASES

RELATED APPLICATIONS

The present application is a national stage filing under 35 U.S.C. §371 of international PCT application, PCT/US2013/047035, filed Jun. 21, 2013, which claims priority under 35 U.S.C. §119(e) to U.S. provisional patent applications, U.S. Ser. No. 61/662,755, filed Jun. 21, 2012, and U.S. Ser. No. 61/798,834, filed Mar. 15, 2013, each of which is incorporated herein by reference.

BACKGROUND OF THE INVENTION

Fungi are a prominent cause of hospital-acquired infections that are becoming increasingly difficult to control (Pfaller, et al. (2007) *Clin Microbiol Rev* 20, 133-163). This disturbing trend is driven by the growing number of severely immunocompromised individuals in the population that has occurred as a result of advances in the management of cancer, organ transplantation, autoimmune disorders, and HIV. Most fungus-related morbidity and mortality is caused by the pathogens *Candida albicans* and *Aspergillus fumigatus*, which remain costly to treat and extremely difficult to eradicate in the immunocompromised host. *Candida* species are currently the fourth leading cause of hospital-acquired bloodstream infection and kill up to 40% of their victims, while disseminated *Aspergillus* infections kill up to 80% of the patients they afflict (Cowen, et al. (2002) *Annu Rev Microbiol* 56, 139-165; Monk, et al. (2008) *Science* 321, 367-369).

Fungal pathogens present a particular therapeutic challenge because as eukaryotes, they share many of the same basic molecular mechanisms that support the maintenance and proliferation of mammalian cells. As a consequence, the number of unique exploitable drug targets that have been identified in fungi remains very limited. Only three mechanistically distinct classes of anti-mycotic agents are in widespread clinical use for the treatment of systemic infections. The most widely deployed class, the azoles (e.g., fluconazole), inhibit the cytochrome P450 enzyme 14 α-demethylase. This blocks the conversion of lanosterol to ergosterol, the functional homolog of cholesterol in mammals. Ergosterol is an essential component of the fungal membrane, and the selective fungistatic activity of the azoles results from their disruption of its biosynthesis. Ergosterol itself is the primary target of the oldest class of antifungals, the polyenes (e.g., amphotericin B) which selectively bind this sterol and directly disrupt fungal membrane integrity. The newest class of antifungals, the echinochandins (e.g., caspofungin), inhibits 1, 3 β-glucan synthase. This enzyme mediates an essential step in the production of glucan, the major structural component of the fungal cell wall. Unfortunately, high-grade resistance to all three classes of antifungals occurs frequently in the clinical setting through molecular mechanisms that can involve both target-related mutations and increased transporter-mediated drug efflux. Accordingly, there remains a need to find anti-fungal agents with new targets.

SUMMARY OF THE INVENTION

Motivated by a long-standing interest in the basic biology of stress responses and how they enable diverse organisms to adapt and evolve, the present inventors identified a chemical structure that induces profound stress in the endoplasmic reticulum (ER) of fungi. Intrigued by its high fungal selectivity against a broad range of medically relevant species, they sought to define its mechanism of action through a combination of genetic and biochemical approaches. The present inventors found that a compound coined gepinacin (FIG. 1a) specifically inhibits an essential step in the production of glycosylphosphatidylinositol (GPI)-anchors within the ER of fungi, but not mammalian cells. Guided by this insight, gepinacin was used as a probe to investigate how inhibiting this biosynthetic pathway disrupts protein homeostasis in fungi and alters key interactions between pathogen and host that are known to contribute to fungal virulence.

The present invention provides compounds and pharmaceutically acceptable forms thereof for use in inhibiting fungal growth and treating fungal infections. The present invention also provides compounds and pharmaceutically acceptable forms thereof for use in inhibiting parasitic growth and treating parasitic infections. In certain embodiments, compounds of the present invention are useful as inhibitors of glycosylphosphatidylinositol (GPI)-anchor biosynthesis, in particular, as inhibitors of Gwt1 activity. The present invention further provides pharmaceutical compositions and methods of using the compounds described herein. In certain embodiments, compounds described herein can be used as biological probes to study the effects of inhibiting enzyme activity, e.g., Gwt1 activity. Provided compounds can also be used as therapeutics, e.g., for the treatment of fungal or parasite infections in a subject.

In one aspect, the present invention provides compounds of Formula I:

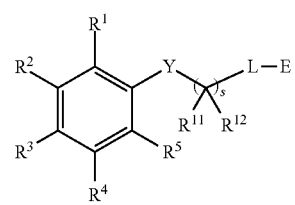

or pharmaceutically acceptable forms (e.g., pharmaceutically acceptable salts) thereof, wherein $R^1$, $R^2$, $R^3$, $R^4$, $R^5$, $R^{11}$, $R^{12}$, Y, L, E, and s are as defined herein.

In certain embodiments, the present invention provides compounds of formula II:

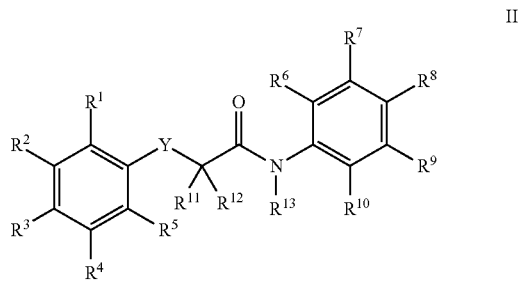

or pharmaceutically acceptable forms (e.g., pharmaceutically acceptable salts) thereof, wherein $R^1$, $R^2$, $R^3$, $R^4$, $R^5$, $R^6$, $R^7$, $R^8$, $R^9$, $R^{10}$, $R^{11}$, $R^{12}$, $R^{13}$, and Y are as defined herein.

In certain embodiments, the present invention provides compounds of formula III:

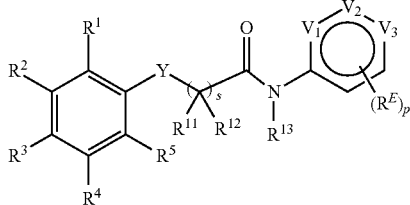

or pharmaceutically acceptable forms (e.g., pharmaceutically acceptable salts) thereof, wherein $R^1$, $R^2$, $R^3$, $R^4$, $R^5$, $R^{11}$, $R^{12}$, $R^E$, Y, $V_1$, $V_2$, $V_3$, p, and s are as defined herein.

In certain embodiments, the present invention provides compounds of formula IV:

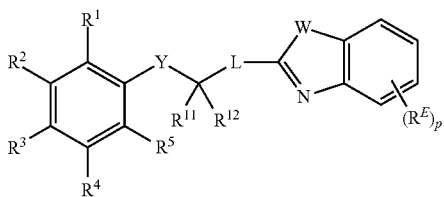

or pharmaceutically acceptable forms (e.g., pharmaceutically acceptable salts) thereof, wherein $R^1$, $R^2$, $R^3$, $R^4$, $R^5$, $R^{11}$, $R^{12}$, $R^E$, Y, L, W, and p are as defined herein.

In certain embodiments, the present invention provides compounds of formula V:

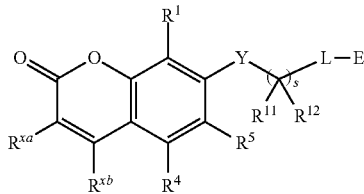

or pharmaceutically acceptable forms (e.g., pharmaceutically acceptable salts) thereof, wherein $R^1$, $R^4$, $R^5$, $R^{11}$, $R^{12}$, $R^{xa}$, $R^{xb}$, L, E, and s are as defined herein.

In certain embodiments, the present invention provides compounds of formula VI:

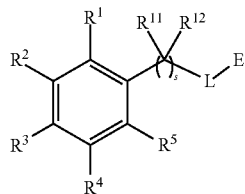

or pharmaceutically acceptable forms (e.g., pharmaceutically acceptable salts) thereof, wherein $R^1$, $R^2$, $R^3$, $R^4$, $R^5$, $R^{11}$, $R^{12}$, L, E, and s are as defined herein.

In another aspect, pharmaceutical compositions are provided which comprise a compound described herein (e.g., a compound of Formula I), or a pharmaceutically acceptable form (e.g., pharmaceutically acceptable salt) thereof, in an amount effective to treat a fungal or parasite infection and a pharmaceutically acceptable excipient.

In yet another aspect, methods of inhibiting fungal growth are provided which comprise contacting a fungus with a compound described herein (e.g., a compound of Formula I), or a pharmaceutically acceptable form (e.g., pharmaceutically acceptable salt) thereof, in an amount sufficient to inhibit growth of the fungus. In certain embodiments, the fungus is *Candida albicans*. In certain embodiments, the fungus is *Candida glabrata*. In certain embodiments, the fungus is *Aspergillus fumigatus*. In certain embodiments, the fungus is *Aspergillus terreus*.

In another aspect, methods of inhibiting parasitic growth are provided which comprise contacting a parasite with a compound described herein (e.g., a compound of Formula I), or a pharmaceutically acceptable form (e.g., pharmaceutically acceptable salt) thereof, in an amount sufficient to inhibit growth of the parasite. In certain embodiments, the parasite is *Plasmodium falciparum*. In certain embodiments, the parasite is *Trypanosome brucei*. In certain embodiments, the parasite is *Trypanosome cruzi*.

In certain embodiments, methods of inhibiting GPI-anchor biosynthesis are provided which comprise contacting a cell with a compound described herein (e.g., a compound of Formula I), or a pharmaceutically acceptable form (e.g., pharmaceutically acceptable salt) thereof, in an amount sufficient to inhibit GPI-anchor biosynthesis in the cell In certain embodiments, methods of inhibiting an acyltransferase (e.g., Gwt1) are provided which comprise contacting the acyltransferase with a compound described herein (e.g., a compound of Formula I), or a pharmaceutically acceptable form (e.g., pharmaceutically acceptable salt) thereof, in an amount sufficient to inhibit activity of the acyltransferase. In certain embodiments, methods of inhibiting Gwt1, or a mutant or variant thereof, are provided which comprise contacting Gwt1, or a mutant or variant thereof, with a compound described herein (e.g., a compound of Formula I), or a pharmaceutically acceptable form (e.g., pharmaceutically acceptable salt) thereof, in an amount sufficient to inhibit activity of the Gwt1, or mutant or variant, thereof. The Gwt1, or mutant or variant thereof, may be purified or crude, and may be present in a cell, tissue, or a subject. Thus, such methods encompasses both inhibition of Gwt1 activity in vitro and in vivo. In certain embodiments, the Gwt1 is wild-type Gwt1.

In still another aspect, methods of preventing or treating fungal infection in a subject are provided which comprise administering an effective amount of a compound described herein (e.g., a compound of Formula I), or a pharmaceutically acceptable form (e.g., pharmaceutically acceptable salt) thereof, to a subject in need of treatment. In certain embodiments, the fungal infection is caused by *Candida albicans*. In certain embodiments, the fungal infection is caused by *Candida glabrata*. In certain embodiments, the fungal infection is caused by *Aspergillus fumigatus*. In certain embodiments, the fungal infection is caused by *Aspergillus terreus*.

In yet another aspect, the present invention provides methods of assaying compounds for Gwt1 activity. In certain embodiments, the present invention provides methods of identifying a compound that inhibits Gwt 1 which comprise contacting Gwt1, or a mutant or variant thereof, with a compound described herein (e.g., a compound of Formula I), or a salt thereof, and determining whether the compound inhibits Gwt1, or a mutant or variant thereof. In certain embodiments, a library of compounds of Formula I is screened for inhibition of Gwt1. In certain embodiments, the compound or library of compounds are also screened against PigW, and selectivity for Gwt 1 compared with PigW is determined.

This application refers to various issued patent, published patent applications, journal articles, and other publications, all of which are incorporated herein by reference.

The details of one or more embodiments of the present invention are set forth herein. Other features, objects, and advantages of the present invention will be apparent from the Detailed Description, the Figures, the Examples, and the Claims.

DEFINITIONS

Chemical Definitions

Definitions of specific functional groups and chemical terms are described in more detail below. The chemical elements are identified in accordance with the Periodic Table of the Elements, CAS version, *Handbook of Chemistry and Physics*, 75$^{th}$ Ed., inside cover, and specific functional groups are generally defined as described therein. Additionally, general principles of organic chemistry, as well as specific functional moieties and reactivity, are described in Thomas Sorrell, *Organic Chemistry*, University Science Books, Sausalito, 1999; Smith and March, *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various isomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. Isomers can be isolated from mixtures by methods known to those skilled in the art, including chiral high pressure liquid chromatography (HPLC) and the formation and crystallization of chiral salts; or preferred isomers can be prepared by asymmetric syntheses. See, for example, Jacques et al., *Enantiomers, Racemates and Resolutions* (Wiley Interscience, New York, 1981); Wilen et al., *Tetrahedron* 33:2725 (1977); Eliel, *Stereochemistry of Carbon Compounds* (McGraw-Hill, NY, 1962); and Wilen, *Tables of Resolving Agents and Optical Resolutions* p. 268 (E. L. Eliel, Ed., Univ. of Notre Dame Press, Notre Dame, Ind. 1972). The invention additionally encompasses compounds described herein as individual isomers substantially free of other isomers, and alternatively, as mixtures of various isomers.

Unless otherwise stated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

"Alkyl" refers to a radical of a straight-chain or branched saturated hydrocarbon group having from 1 to 20 carbon atoms ("$C_{1-20}$ alkyl"). In some embodiments, an alkyl group has 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), isopropyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently optionally substituted, i.e., unsubstituted (an "unsubstituted alkyl") or substituted (a "substituted alkyl") with one or more substituents. In certain embodiments, the alkyl group is unsubstituted $C_{1-10}$ alkyl (e.g., $CH_3$). In certain embodiments, the alkyl group is substituted $C_{1-10}$ alkyl.

"Alkenyl" refers to a radical of a straight-chain or branched hydrocarbon group having from 2 to 20 carbon atoms, one or more carbon-carbon double bonds, and no triple bonds ("$C_{2-20}$ alkenyl"). In some embodiments, an alkenyl group has 2 to 10 carbon atoms ("$C_{2-10}$ alkenyl"). In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1 Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently optionally substituted, i.e., unsubstituted (an "unsubstituted alkenyl") or substituted (a "substituted alkenyl") with one or more substituents. In certain embodiments, the alkenyl group is unsubstituted $C_{2-10}$ alkenyl. In certain embodiments, the alkenyl group is substituted $C_{2-10}$ alkenyl.

"Alkynyl" refers to a radical of a straight-chain or branched hydrocarbon group having from 2 to 20 carbon atoms, one or more carbon-carbon triple bonds, and optionally one or more double bonds ("$C_{2-20}$ alkynyl"). In some embodiments, an alkynyl group has 2 to 10 carbon atoms ("$C_{2-10}$ alkynyl"). In some embodiments, an alkynyl group has 2 to 9 carbon atoms ("$C_{2-9}$ alkynyl"). In some embodiments, an alkynyl group has 2 to 8 carbon atoms ("$C_{2-8}$ alkynyl"). In some embodiments, an alkynyl group has 2 to 7 carbon atoms ("$C_{2-7}$ alkynyl"). In some embodiments, an alkynyl group has 2 to 6 carbon atoms ("$C_{2-6}$ alkynyl"). In some embodiments, an alkynyl group has 2 to 5 carbon atoms ("$C_{2-5}$ alkynyl"). In some embodiments, an alkynyl group has 2 to 4 carbon atoms ("$C_{2-4}$ alkynyl"). In some embodiments, an alkynyl group has 2 to 3 carbon atoms ("$C_{2-3}$ alkynyl"). In some embodiments, an alkynyl group has 2 carbon atoms ("$C_2$ alkynyl"). The one or more carbon-carbon triple bonds can be internal (such as in 2-butynyl) or terminal (such as in 1-butynyl). Examples of $C_{2-4}$ alkynyl groups include, without limitation, ethynyl ($C_2$), 1-propynyl ($C_3$), 2-propynyl ($C_3$), 1-butynyl ($C_4$), 2-butynyl ($C_4$), and the like. Examples of $C_{2-6}$ alkenyl groups include the aforementioned $C_{2-4}$ alkynyl groups as well as pentynyl ($C_5$), hexynyl ($C_6$), and the like. Additional examples of alkynyl include heptynyl ($C_7$), octynyl ($C_8$), and the like. Unless otherwise specified, each instance of an alkynyl group is independently optionally substituted, i.e., unsubstituted (an "unsubstituted alkynyl") or substituted (a "substituted alkynyl") with one or more substituents. In certain embodiments, the alkynyl group is unsubstituted $C_{2-10}$ alkynyl. In certain embodiments, the alkynyl group is substituted $C_{2-10}$ alkynyl.

"Carbocyclyl" or "carbocyclic" refers to a radical of a non-aromatic cyclic hydrocarbon group having from 3 to 10 ring carbon atoms ("$C_{3-10}$ carbocyclyl") and zero heteroatoms in the non-aromatic ring system. In some embodiments, a carbocyclyl group has 3 to 8 ring carbon atoms ("$C_{3-8}$ carbocyclyl"). In some embodiments, a carbocyclyl group has 3 to 6 ring carbon atoms ("$C_{3-6}$ carbocyclyl"). In some embodiments, a carbocyclyl group has 3 to 6 ring carbon atoms ("$C_{3-6}$ carbocyclyl"). In some embodiments, a carbocyclyl group has 5 to 10 ring carbon atoms ("$C_{5-10}$ carbocyclyl"). Exemplary $C_{3-6}$ carbocyclyl groups include, without limitation, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), and the like. Exemplary $C_{3-8}$ carbocyclyl groups include, without limitation, the aforementioned $C_{3-6}$ carbocyclyl groups as well as cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), and the like. Exemplary $C_{3-10}$ carbocyclyl groups include, without limitation, the aforementioned $C_{3-8}$ carbocyclyl groups as well as cyclononyl ($C_9$), cyclononenyl ($C_9$), cyclodecyl ($C_{10}$), cyclodecenyl ($C_{10}$), octahydro-1H-indenyl ($C_9$), decahydronaphthalenyl ($C_{10}$), spiro[4.5]decanyl ($C_{10}$), and the like. As the foregoing examples illustrate, in certain embodiments, the carbocyclyl group is either monocyclic ("monocyclic carbocyclyl") or contain a fused, bridged, or spiro ring system such as a bicyclic system ("bicyclic carbocyclyl") and can be saturated or can be partially unsaturated. "Carbocyclyl" also includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently optionally substituted, i.e., unsubstituted (an "unsubstituted carbocyclyl") or substituted (a "substituted carbocyclyl") with one or more substituents. In certain embodiments, the carbocyclyl group is unsubstituted $C_{3-10}$ carbocyclyl. In certain embodiments, the carbocyclyl group is a substituted $C_{3-10}$ carbocyclyl.

In some embodiments, "carbocyclyl" is a monocyclic, saturated carbocyclyl group having from 3 to 10 ring carbon atoms ("$C_{3-10}$ cycloalkyl"). In some embodiments, a cycloalkyl group has 3 to 8 ring carbon atoms ("$C_{3-8}$ cycloalkyl"). In some embodiments, a cycloalkyl group has 3 to 6 ring carbon atoms ("$C_{3-6}$ cycloalkyl"). In some embodiments, a cycloalkyl group has 5 to 6 ring carbon atoms ("$C_{5-6}$ cycloalkyl"). In some embodiments, a cycloalkyl group has 5 to 10 ring carbon atoms ("$C_{5-10}$ cycloalkyl"). Examples of $C_{5-6}$ cycloalkyl groups include cyclopentyl ($C_5$) and cyclohexyl ($C_5$). Examples of $C_{3-6}$ cycloalkyl groups include the aforementioned $C_{5-6}$ cycloalkyl groups as well as cyclopropyl ($C_3$) and cyclobutyl ($C_4$). Examples of $C_{3-8}$ cycloalkyl groups include the aforementioned $C_{3-6}$ cycloalkyl groups as well as cycloheptyl ($C_7$) and cyclooctyl ($C_8$). Unless otherwise specified, each instance of a cycloalkyl group is independently unsubstituted (an "unsubstituted cycloalkyl") or substituted (a "substituted cycloalkyl") with one or more substituents. In certain embodiments, the cycloalkyl group is unsubstituted $C_{3-10}$ cycloalkyl. In certain embodiments, the cycloalkyl group is substituted $C_{3-10}$ cycloalkyl.

"Heterocyclyl" or "heterocyclic" refers to a radical of a 3 to 10-membered non aromatic ring system having ring carbon atoms and 1 to 4 ring heteroatoms, wherein each heteroatom is independently selected from nitrogen, oxygen, and sulfur ("3-10 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or a fused, bridged or spiro ring system such as a bicyclic system ("bicyclic heterocyclyl"), and can be saturated or can be partially unsaturated. Heterocyclyl bicyclic ring systems can include one or more heteroatoms in one or both rings. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently optionally substituted, i.e., unsubstituted (an "unsubstituted heterocyclyl") or substituted (a "substituted heterocyclyl") with one or more substituents. In certain embodiments, the heterocyclyl group is unsubstituted 3-10 membered heterocyclyl. In certain embodiments, the heterocyclyl group is substituted 3-10 membered heterocyclyl.

In some embodiments, a heterocyclyl group is a 5-10 membered non-aromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has one ring heteroatom selected from nitrogen, oxygen, and sulfur.

Exemplary 3-membered heterocyclyl groups containing one heteroatom include, without limitation, azirdinyl, oxiranyl, thiorenyl. Exemplary 4-membered heterocyclyl groups containing one heteroatom include, without limitation, azetidinyl, oxetanyl and thietanyl. Exemplary 5-membered heterocyclyl groups containing one heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5 heterocyclyl groups containing two heteroatoms include, without limitation, dioxolanyl, oxasulfuranyl, disulfuranyl, and oxazolidin-2-one. Exemplary 5-membered heterocyclyl groups containing three heteroatoms include, without limitation, triazolinyl, oxadiazolinyl, and thiadiazolinyl. Exemplary 6-membered heterocyclyl groups containing one heteroatom include, without limitation, piperidinyl, tetrahydropyranyl, dihydropyridinyl, and thianyl. Exemplary 6-membered heterocyclyl groups containing two heteroatoms include, without limitation, piperazinyl, morpholinyl, dithianyl, and dioxanyl. Exemplary 6 heterocyclyl groups containing two heteroatoms include, without limitation, triazinanyl. Exemplary 7-membered heterocyclyl groups containing one heteroatom include, without limitation, azepanyl, oxepanyl and thiepanyl. Exemplary 8-membered heterocyclyl groups containing one heteroatom include, without limitation, azocanyl, oxecanyl, and thiocanyl. Exemplary 5-membered heterocyclyl groups fused to a $C_6$ aryl ring (also referred to herein as a 5,6-bicyclic heterocyclic ring) include, without limitation, indolinyl, isoindolinyl, dihydrobenzofuranyl, dihydrobenzothienyl, benzoxazolinonyl, and the like. Exemplary 6-membered heterocyclyl groups fused to an aryl ring (also referred to herein as a 6,6-bicyclic heterocyclic ring) include, without limitation, tetrahydroquinolinyl, tetrahydroisoquinolinyl, and the like.

"Aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently optionally substituted, i.e., unsubstituted (an "unsubstituted aryl") or substituted (a "substituted aryl") with one or more substituents. In certain embodiments, the aryl group is unsubstituted $C_{6-14}$ aryl. In certain embodiments, the aryl group is substituted $C_{6-14}$ aryl.

"Heteroaryl" refers to a radical of a 5-10 membered monocyclic or bicyclic 4n+2 aromatic ring system (e.g., having 6 or 10 π electrons shared in a cyclic array) having ring carbon atoms and 1-4 ring heteroatoms provided in the aromatic ring system, wherein each heteroatom is independently selected from nitrogen, oxygen and sulfur ("5-10 membered heteroaryl"). In heteroaryl groups that contain one or more nitrogen atoms, the point of attachment can be a carbon or nitrogen atom, as valency permits. Heteroaryl bicyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused (aryl/heteroaryl) ring system. Bicyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently optionally substituted, i.e., unsubstituted ("unsubstituted heteroaryl") or substituted ("substituted heteroaryl") with one or more substituents. In certain embodiments, the heteroaryl group is unsubstituted 5-14 membered heteroaryl. In certain embodiments, the heteroaryl group is substituted 5-14 membered heteroaryl.

Exemplary 5-membered heteroaryl groups containing one heteroatom include, without limitation, pyrrolyl, furanyl and thiophenyl. Exemplary 5-membered heteroaryl groups containing two heteroatoms include, without limitation, imidazolyl, pyrazolyl, oxazolyl, isoxazolyl, thiazolyl, and isothiazolyl. Exemplary 5-membered heteroaryl groups containing three heteroatoms include, without limitation, triazolyl, oxadiazolyl, and thiadiazolyl. Exemplary 5-membered heteroaryl groups containing four heteroatoms include, without limitation, tetrazolyl. Exemplary 6-membered heteroaryl groups containing one heteroatom include, without limitation, pyridinyl. Exemplary 6-membered heteroaryl groups containing two heteroatoms include, without limitation, pyridazinyl, pyrimidinyl, and pyrazinyl. Exemplary 6-membered heteroaryl groups containing three or four heteroatoms include, without limitation, triazinyl and tetrazinyl, respectively. Exemplary 7-membered heteroaryl groups containing one heteroatom include, without limitation, azepinyl, oxepinyl, and thiepinyl. Exemplary 5,6-bicyclic heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6 heteroaryl groups include, without limitation, naphthyridinyl, pteridinyl, quinolinyl, isoquinolinyl, cinnolinyl, quinoxalinyl, phthalazinyl, and quinazolinyl.

"Partially unsaturated" refers to a group that includes at least one double or triple bond. The term "partially unsaturated" is intended to encompass rings having multiple sites of unsaturation, but is not intended to include aromatic groups (e.g., aryl or heteroaryl groups) as herein defined. Likewise, "saturated" refers to a group that does not contain a double or triple bond, i.e., contains all single bonds.

Alkyl, alkenyl, alkynyl, carbocyclyl, heterocyclyl, aryl, and heteroaryl groups, as defined herein, are optionally substituted (e.g., "substituted" or "unsubstituted" alkyl, "substituted" or "unsubstituted" alkenyl, "substituted" or "unsubstituted" alkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$—C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, wherein each alkyl, alkenyl, alkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, —OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{cc}$, —SC(=S)SR$^{cc}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{3-10}$ carbocyclyl, 3-10 membered heterocyclyl, C$_{6-10}$ aryl, 5-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups, or two geminal $R^{dd}$ substituents can be joined to form =O or =S;

each instance of $R^{ee}$ is, independently, selected from $C_{1-6}$ alkyl, $C_{1-6}$ perhaloalkyl, $C_{2-6}$ alkenyl, $C_{2-6}$ alkynyl, $C_{3-10}$ carbocyclyl, $C_{6-10}$ aryl, 3-10 membered heterocyclyl, and 3-10 membered heteroaryl, wherein each alkyl, alkenyl, alkynyl, carbocyclyl, heterocyclyl, aryl, and heteroaryl is independently substituted with 0, 1, 2, 3, 4, or 5 $R^{gg}$ groups;

each instance of $R^{ff}$ is, independently, selected from hydrogen, $C_{1-6}$ alkyl, $C_{1-6}$ perhaloalkyl, $C_{2-6}$ alkenyl, $C_{2-6}$ alkynyl, $C_{3-10}$ carbocyclyl, 3-10 membered heterocyclyl, $C_6$-10 aryl and 5-10 membered heteroaryl, or two $R^{ff}$ groups are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3^+$X$^-$, —NH(C$_{1-6}$ alkyl)$_2^+$X$^-$, —NH$_2$(C$_{1-6}$ alkyl)$^+$X$^-$, —NH$_3^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$—C(=S)N(C$_{1-6}$ alkyl)$_2$, C(=S)NH(C$_{1-6}$ alkyl), C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_1$ alkyl, C$_{1-6}$ perhaloalkyl, C$_{2-6}$ alkenyl, C$_{2-6}$ alkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

A "counterion" or "anionic counterion" is a negatively charged group associated with a cationic quaternary amino group in order to maintain electronic neutrality. Exemplary counterions include halide ions (e.g., F$^-$, Cl$^-$, Br$^-$, I$^-$), NO$_3^-$, ClO$_4^-$, OH$^-$, H$_2$PO$_4^-$, HSO$_4^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

"Halo" or "halogen" refers to fluorine (fluoro, —F), chlorine (chloro, —Cl), bromine (bromo, —Br), or iodine (iodo, —I).

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl, or two R$^{cc}$ groups attached to a nitrogen atom are joined to form a 3-14 membered heterocyclyl or 5-14 membered heteroaryl ring, wherein each alkyl, alkenyl, alkynyl, carbocyclyl, heterocyclyl, aryl, and heteroaryl is independently substituted with 0, 1, 2, 3, 4, or 5 R$^{cc}$ groups, and wherein R$^{aa}$, R$^{bb}$, R$^{cc}$ and R$^{dd}$ are as defined above.

In certain embodiments, the substituent present on a nitrogen atom is a nitrogen protecting group (also referred to as an amino protecting group). Nitrogen protecting groups include, but are not limited to, —OH, —OR$^{aa}$, —N(R$^{cc}$)$_2$, —C(O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, carbocyclyl, heterocyclyl, aralkyl, aryl, and heteroaryl is independently substituted with 0, 1, 2, 3, 4, or 5 R$^{dd}$ groups, and wherein R$^{aa}$, R$^{bb}$, R$^{cc}$, and R$^{dd}$ are as defined herein. Nitrogen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Amide nitrogen protecting groups (e.g., —C(=O)R$^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitophenylacetamide, o-nitrophenoxyacetamide, acetoacetamide, (N'-dithiobenzyloxyacylamino)acetamide, 3-(p hydroxyphenyl)propanamide, 3-(o-nitrophenyl)propanamide, 2-methyl-2-(o nitrophenoxy)propanamide, 2-methyl-2-(ophenylazophenoxy) propanamide, 4-chlorobutanamide, 3-methyl-3-nitrobutanamide, o-nitrocinnamide, N-acetylmethionine, o nitrobenzamide, and o-(benzoyloxymethyl)benzamide.

Carbamate nitrogen protecting groups (e.g., —C(=O) OR$^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl)ethyl carbamate (Pyoc), 2-(N,N-dicyclohexylcarboxamido)ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isoborynl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Sulfonamide nitrogen protecting groups (e.g., —S(=O)$_2$R$^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene) amine, N,N'-isopropylidenediamine, N-p-nitrobenzylideneamine, N-salicylideneamine, N-5-chlorosalicylideneamine, N-(5-chloro-2-hydroxyphenyl) phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to as a hydroxyl protecting group). Oxygen protecting groups include, but are not limited to, —R$^{aa}$, —N(R$^{bb}$)$_2$, —C(=O)SR$^{aa}$, —C(=O)R$^{aa}$, —CO$_2$R$^{aa}$, —C(=O)N(R$^{bb}$)$_2$, —C(=NR$^{bb}$)R$^{aa}$, —C(=NR$^{bb}$)OR$^{aa}$, —C(=NR$^{bb}$)N(R$^{bb}$)$_2$, —S(=O)R$^{aa}$, —SO$_2$R$^{aa}$, —Si(R$^{aa}$)$_3$, —P(R$^{cc}$)$_2$, —P(R$^{cc}$)$_3$, —P(=O)$_2$R$^{aa}$, —P(=O)(R$^{aa}$)$_2$, —P(=O)(OR$^{cc}$)$_2$, —P(=O)$_2$N(R$^{bb}$)$_2$, and —P(=O)(NR$^{bb}$)$_2$, wherein R$^{aa}$, R$^{bb}$, and R$^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl) methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl) ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxido, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxide, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris (levulinoyloxyphenyl)methyl, 4,4',4"-tris (benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9- phenyl-10-oxo)anthryl, 1,3-benzodisulfuran-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napththyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate), benzylsulfonate, and tosylate (Ts).

In certain embodiments, the substituent present on a sulfur atom is a sulfur protecting group (also referred to as a thiol protecting group). Sulfur protecting groups include, but are not limited to, $-R^{aa}$, $-N(R^{bb})_2$, $-C(=O)SR^{aa}$, $-C(=O)R^{aa}$, $-CO_2R^{aa}$, $-C(=O)N(R^{bb})_2$, $-C(=NR^{bb})R^{aa}$, $-C(=NR^{bb})OR^{aa}$, $-C(=NR^{bb})N(R^{bb})_2$, $-S(=O)R^{aa}$, $-SO_2R^{aa}$, $-Si(R^{aa})_3$, $-P(R^{cc})_2$, $-P(R^{cc})_3$, $-P(=O)_2R^{aa}$, $-P(=O)(R^{aa})_2$, $-P(=O)(OR^{cc})_2$, $-P(=O)_2N(R^{bb})_2$, and $-P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3rd edition, John Wiley & Sons, 1999, incorporated herein by reference.

These and other exemplary substituents are described in more detail in the Detailed Description, Examples, and claims. The present invention is not intended to be limited in any manner by the above exemplary listing of substituents.

OTHER DEFINITIONS

The term "pharmaceutically acceptable form thereof" as used herein refers to pharmaceutically acceptable salts, solvates, hydrates, prodrugs, tautomers, isomers, enantiomers, diastereomers, and/or polymorphs of a compound of the present invention.

In certain embodiments, the pharmaceutically acceptable form is a pharmaceutically acceptable salt. The term "pharmaceutically acceptable salt" as used herein refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describe pharmaceutically acceptable salts in detail in *J. Pharmaceutical Sciences*, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

In certain embodiments, the pharmaceutically acceptable form is a hydrate or solvate. The term "hydrate" as used herein refers to a compound non-covalently associated with one or more molecules of water. Likewise, the term "solvate" refers to a compound non-covalently associated with one or more molecules of an organic solvent.

In certain embodiments, the pharmaceutically acceptable form is a prodrug. The term "prodrug" as used herein refers to a derivative of a parent compound that requires transformation within the body in order to release the parent compound. In certain cases, a prodrug has improved physical and/or delivery properties over the parent compound. Prodrugs are typically designed to enhance pharmaceutically and/or pharmacokinetically based properties associated with the parent compound. The advantage of a prodrug can lie in its physical properties, such as enhanced water solubility for parenteral administration at physiological pH compared to the parent compound, or it enhances absorption from the digestive tract, or it may enhance drug stability for long-term storage. In recent years several types of bioreversible derivatives have been exploited for utilization in designing prodrugs. Using esters as a prodrug type for compounds containing a carboxyl or hydroxyl functionality is known in the art as described, for example, in *The Organic Chemistry of Drug Design and Drug Interaction* by Richard Silverman, published by Academic Press (1992).

In certain embodiments, the pharmaceutically acceptable form is a tautomer. The term "tautomer" as used herein includes two or more interconvertable compounds resulting from at least one formal migration of a hydrogen atom and at least one change in valency (e.g., a single bond to a double bond, a triple bond to a single bond, or vice versa). The exact ratio of the tautomers depends on several factors, including temperature, solvent, and pH. Tautomerizations (i.e., the reaction providing a tautomeric pair) may catalyzed by acid or base. Exemplary tautomerizations include keto-to-enol; amide-to-imide; lactam-to-lactim; enamine-to-imine; and enamine-to-(a different) enamine tautomerizations.

In certain embodiments, the pharmaceutically acceptable form is an isomer. The term "isomer" as used herein includes any and all geometric isomers and stereoisomers (e.g., enantiomers, diasteromers, etc.). For example, "isomer" include cis- and trans-isomers, E- and Z-isomers, R- and S-enantiomers, diastereomers, (D)-isomers, (L)-isomers, racemic mixtures thereof, and other mixtures thereof, as falling within the scope of the invention. For instance, an isomer/enantiomer may, in some embodiments, be provided substantially free of the corresponding enantiomer, and may also be referred to as "optically enriched." "Optically-enriched," as used herein, means that the compound is made up of a significantly greater proportion of one enantiomer. In certain embodiments the compound of the present invention is made up of at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including chiral high pressure liquid chromatography (HPLC) and the formation and crystallization of chiral salts or prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); Wilen, S. H. *Tables of Resolving Agents and Optical Resolutions* p. 268 (E. L. Eliel, Ed., Univ. of Notre Dame Press, Notre Dame, Ind. 1972).

In certain embodiments, the pharmaceutically acceptable form is a polymorph. The term "polymorph" as used herein refers to a crystalline compound existing in more than one crystalline form/structure. When polymorphism exists as a result of difference in crystal packing it is called packing polymorphism. Polymorphism can also result from the existence of different conformers of the same molecule in conformational polymorphism. In pseudopolymorphism the different crystal types are the result of hydration or solvation.

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female at any stage of development. A non-human animal may be a transgenic animal.

"Condition," "disease," and "disorder" are used interchangeably herein.

"Treat," "treating" and "treatment" encompasses an action that occurs while a subject is suffering from a condition which reduces the severity of the condition or retards or slows the progression of the condition ("therapeutic treatment").

"Prevent," "preventing" and "prevention" encompasses an action that occurs before a subject begins to suffer from the condition and which inhibits or reduces the severity of the condition ("prophylactic treatment").

An "effective amount" of a compound refers to an amount sufficient to elicit the desired biological response, i.e., treat the condition. As will be appreciated by those of ordinary skill in this art, the effective amount of a compound of the invention may vary depending on such factors as the desired biological endpoint, the pharmacokinetics of the compound, the condition being treated, the mode of administration, and the age and health of the subject. An effective amount encompasses therapeutic and prophylactic treatment.

A "therapeutically effective amount" of a compound is an amount sufficient to provide a therapeutic benefit in the treatment of a condition or to delay or minimize one or more symptoms associated with the condition. A therapeutically effective amount of a compound means an amount of therapeutic agent, alone or in combination with other therapies, which provides a therapeutic benefit in the treatment of the condition. The term "therapeutically effective amount" can encompass an amount that improves overall therapy, reduces or avoids symptoms or causes of the condition, or enhances the therapeutic efficacy of another therapeutic agent.

A "prophylactically effective amount" of a compound is an amount sufficient to prevent a condition, or one or more symptoms associated with the condition or prevent its recurrence. A prophylactically effective amount of a compound means an amount of a therapeutic agent, alone or in combination with other agents, which provides a prophylactic benefit in the prevention of the condition. The term "prophylactically effective amount" can encompass an amount that improves overall prophylaxis or enhances the prophylactic efficacy of another prophylactic agent.

As used herein, the term "in a subject" means in or on a subject. The area to be treated may be on the inside of the subject (e.g., in the blood, in an organ), or it may be a surface on the subject that can be topically treated (e.g., on the scalp, on the skin).

The term "mutant," as used herein, refers to a sequence (e.g., a protein sequence or a nucleic acid sequence) having at least one mutation. The term "mutation," as used herein, refers to a substitution of a residue within a sequence, e.g., a nucleic acid or amino acid sequence, with another residue, or a deletion or insertion of one or more residues within a sequence.

The term "variant," as used herein, refers to variations of the nucleic acid or amino acid sequences of Gwt1. Encompassed within the term "variant" are nucleotide and amino acid substitutions, additions, or deletions of Gwt1 molecules. Also, encompassed within the term "variant" are chemically modified natural and synthetic Gwt1 molecules. For example, variant may refer to polypeptides that differ from a reference polypeptide. Generally, the differences between the polypeptide that differs in amino acid sequence from reference polypeptide, and the reference polypeptide are limited so that the amino acid sequences of the reference and the variant are closely similar overall and, in some regions, identical. A variant and reference polypeptide may differ in amino acid sequence by one or more substitutions, deletions, additions, fusions and truncations that may be conservative or non-conservative and may be present in any combination. For example, variants may be those in which several, for instance from 50 to 30, from 30 to 20, from 20 to 10, from 10 to 5, from 5 to 3, from 3 to 2, from 2 to 1 or 1 amino acids are inserted, substituted, or deleted, in any combination. Additionally, a variant may be a fragment of a polypeptide of the invention that differs from a reference polypeptide sequence by being shorter than the reference sequence, such as by a terminal or internal deletion. A variant of a polypeptide of the invention also includes a polypeptide which retains essentially the same biological function or activity as such polypeptide, e.g., precursor proteins which can be activated by cleavage of the precursor portion to produce an active mature polypeptide. These variants may be allelic variations characterized by differences in the nucleotide sequences of the structural gene coding for the protein, or may involve differential splicing or post-translational modification. Variants also include a related protein having substantially the same biological activity, but obtained from a different species. The skilled artisan can produce variants having single or multiple amino acid substitutions, deletions, additions, or replacements. These variants may include, inter alia: (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more amino acids are deleted from the peptide or protein, or (iii) one in which one or more amino acids are added to the polypeptide or protein, or (iv) one in which one or more of the amino acid residues include a substituent group, or (v) one in which the mature polypeptide is fused with another compound, such as a compound to increase the half-life of the polypeptide (for example, polyethylene glycol), or (vi) one in which the additional amino acids are fused to the mature polypeptide such as a leader or secretory sequence or a sequence which is employed for purification of the mature polypeptide or a precursor protein sequence. A variant of the polypeptide may also be a naturally occurring variant such as a naturally occurring allelic variant, or it may be a variant that is not known to occur naturally.

BRIEF DESCRIPTION OF THE DRAWINGS

FIGS. 22A-D show the determination of the exemplary compounds' specificity using Bactiter Glo. "Yeast gene" means the *S. cerevisiae* gene.

DETAILED DESCRIPTION OF CERTAIN EMBODIMENTS OF THE INVENTION

Figure 1:
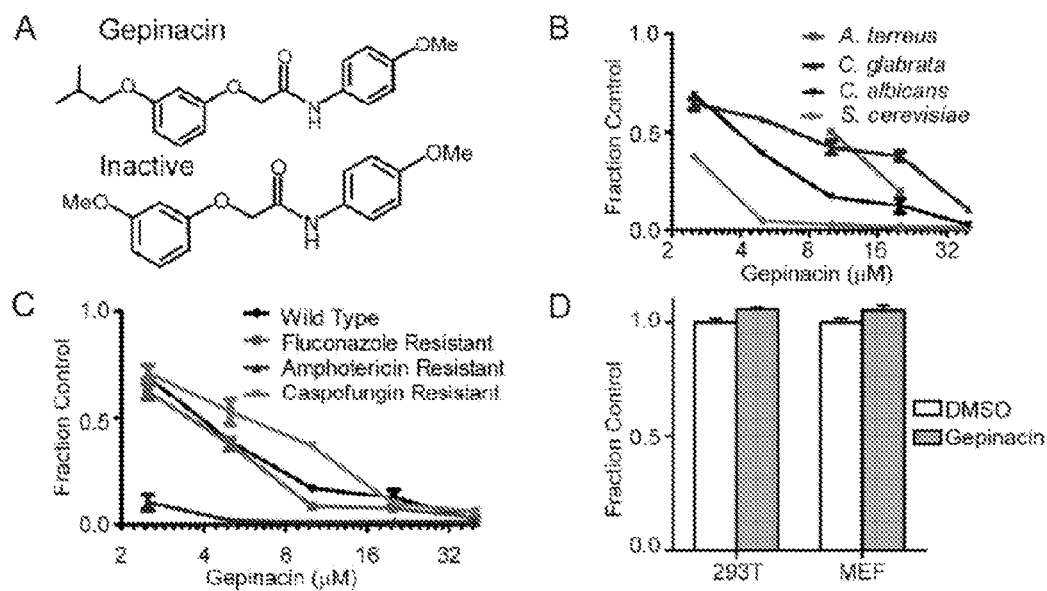
FIG. 1 shows that gepinacin inhibits growth of evolutionarily distant fungi but does not affect mammalian cells. (A) Structures of gepinacin and a similar but inactive compound. (B) Anti-fungal susceptibility testing for an evolutionarily diverse group of fungi treated with gepinacin. For *A. terreus* the MIC50 and MIC80 are plotted. (C) Anti-fungal susceptibility testing for wild type *C. albicans* and strains resistant to the three major classes of anti-fungals treated with gepinacin. (D) Mammalian cell toxicity testing for proliferating human cells in culture (293T) or quiescent cells (mouse embryo fibroblasts). Cells were treated with gepinacin (20 μM) for 48 hours after which relative viable cell number was measured by standard luciferase assay (Cell Titer-Glo®, Promega).

The present invention provides compounds which are useful for inhibiting fungal or parasitic growth. The present invention further provides pharmaceutical compositions of compounds described herein and methods of using the compounds. In certain embodiments, the compound is an inhibitor of GPI-anchor biosynthesis. In certain embodiments, the compound is an acyltransferase inhibitor. In certain embodiments, the compound is a Gwt1 inhibitor. In certain embodiments, the compound is used to prevent and/or treat a fungal or parasitic infection in a subject.

In fungi, the anchoring of proteins to the plasma membrane via their covalent attachment to glycosylphosphatidylinositol (GPI) is essential and thus provides a valuable point of attack for the development of antifungal therapeutics. Unfortunately, studying the underlying biology of GPI-anchor synthesis can be difficult, especially in medically relevant fungal pathogens because they are not genetically tractable. Further compounding these difficulties, many of the genes in this pathway are essential in *Saccharomyces cerevisiae*. The present inventors have discovered that a small molecule they named gepinacin (for GPI acylation inhibitor) selectively inhibits Gwt1, a critical acyltransferase required for the biosynthesis of fungal GPI anchors. After delineating the target specificity of gepinacin using genetic and biochemical techniques, it was used to probe key, therapeutically relevant consequences of disrupting GPI anchor metabolism in fungi. It was found that unlike all three major classes of antifungals in current use, the direct antimicrobial activity of this compound results predominantly from its ability to induce overwhelming stress to the endoplasmic reticulum. Gepinacin did not affect the viability of mammalian cells nor does it inhibit their orthologonal acyltransferase. This enabled its use in co-culture experiments to examine the effects of Gwt1 on host-pathogen interactions. In isolates of *Candida albicans*, the most common fungal pathogen in humans, exposure to gepinacin at sub-lethal concentrations impaired filamentation and unmasked cell wall β-glucan to stimulate a pro-inflammatory cytokine response in macrophages. Gwt1 is a promising antifungal drug target, and gepanacin is a useful probe for studying how disrupting GPI-anchor synthesis impairs viability and alters host-pathogen interactions in fungi.

Compounds

As generally described above, the present invention provides compounds useful as acyltransferase inhibitors, e.g., Gwt1 inhibitors. In one aspect, the present invention provides compound of Formula I:

In one aspect, the present invention provides compound of Formula I:

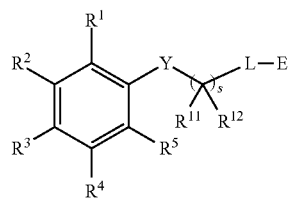

or a pharmaceutically acceptable form thereof,
wherein:

$R^1$, $R^3$, $R^4$, $R^5$, are independently selected from the group consisting of hydrogen, halo, —CN, —NO$_2$, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)OR$^A$, —NR$^B$C(=O)OR$^A$, —OC(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each occurrence of R$^A$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of R$^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two R$^B$ groups are joined to form an optionally substituted heterocyclic ring;

$R^2$ is hydrogen, halogen, or —O—R$^X$ $R^X$ is optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, or optionally substituted heteroaralkyl;

optionally R$^X$ and R$^3$ are taken together with their intervening atoms to form an optionally substituted heterocyclic ring;

Y is a bond, —O—, or —S—;

each instance of R$^{11}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, or optionally substituted heteroaralkyl;

each instance of R$^{12}$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, or optionally substituted heteroaralkyl;

L is a bond, —NR$^{13}$C(=O)—, or —C(=O)NR$^{13}$—;

R$^{13}$ is hydrogen or C$_{1-6}$ alkyl;

E is optionally substituted aryl or optionally substituted heteroaryl; and s is 1, 2, 3, 4, 5, or 6.

In certain embodiments, a compound of formula I is of formula II:

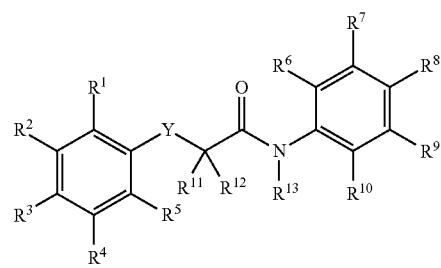

or a pharmaceutically acceptable form thereof,
wherein:

R$^6$, R$^7$, R$^8$, R$^9$, and R$^{10}$ are independently selected from the group consisting of hydrogen, halo, —CN, —NO$_2$, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)OR$^A$, —NR$^B$C(=O)OR$^A$, —OC(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$.

In certain embodiments, a compound of formula I is of formula II-a:

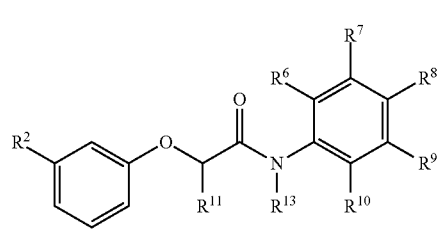

or a pharmaceutically acceptable form thereof.

In certain embodiments, a compound of formula I is of formula II-b:

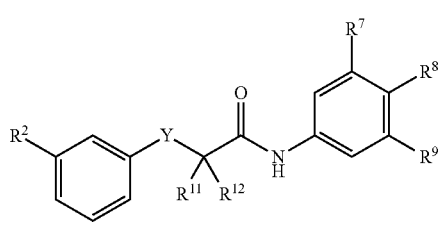

or a pharmaceutically acceptable form thereof.

In certain embodiments, a compound of formula I is formula II-c:

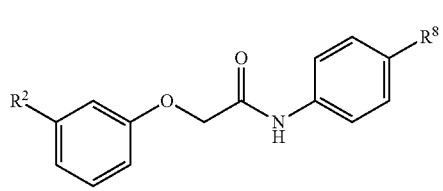

or a pharmaceutically acceptable form thereof.

In certain embodiments, a compound of formula I is of formula II-d:

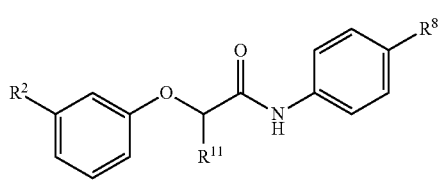

or a pharmaceutically acceptable form thereof.

In certain embodiments, a compound of formula I is of formula III:

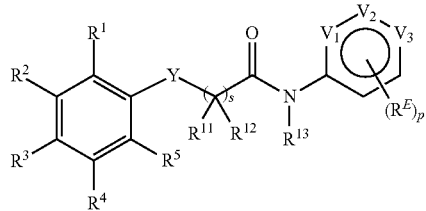

or a pharmaceutically acceptable form thereof,
wherein:
  each instance of $V_1$, $V_2$, and $V_3$ is independently N or C, provided that at least one of $V_1$, $V_2$, and $V_3$ is N;
  each instance of $R^E$ is independently selected from the group consisting of hydrogen, halo, —CN, —NO$_2$, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)OR$^A$, —NR$^B$C(=O)OR$^A$, —OC(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; and
p is 0, 1, 2, 3, 4, or 5 as valency permits.

In certain embodiments, a compound of formula I is formula III-a:

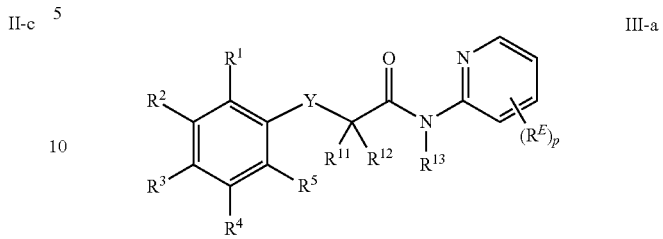

or a pharmaceutically acceptable form thereof.

In certain embodiments, a compound of formula I is of formula III-a1:

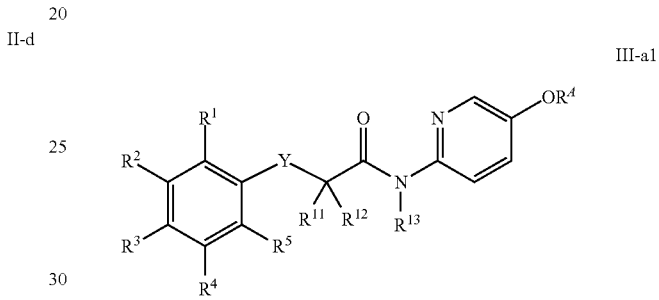

or a pharmaceutically acceptable form thereof.

In certain embodiments, a compound of formula I is of formula III-b:

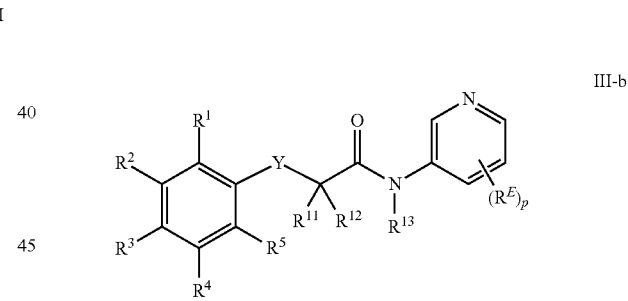

or a pharmaceutically acceptable form thereof.

In certain embodiments, a compound of formula I is formula III-b1:

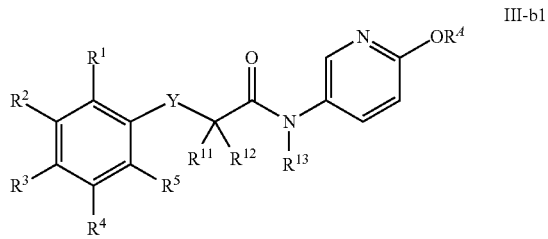

or a pharmaceutically acceptable form thereof.

In certain embodiments, a compound of formula I is of formula III-c:

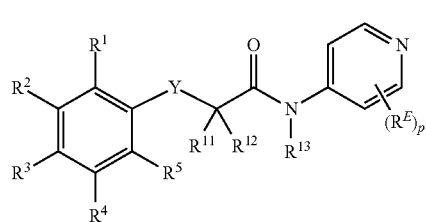

III-c or a pharmaceutically acceptable form thereof.

In certain embodiments, a compound of formula I is of formula IV:

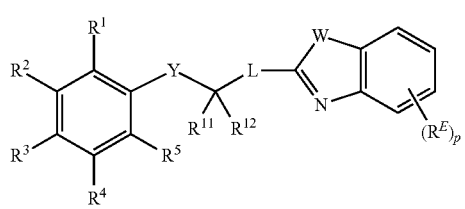

IV or a pharmaceutically acceptable form thereof,
wherein
W is O, S, or $NR^q$; and
$R^q$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group.

In certain embodiments, a compound of formula I is of formula IV-a:

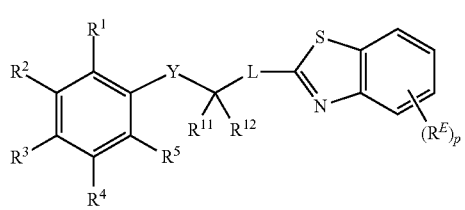

IV-a or a pharmaceutically acceptable form thereof.

In certain embodiments, a compound of formula I is of formula IV-a1:

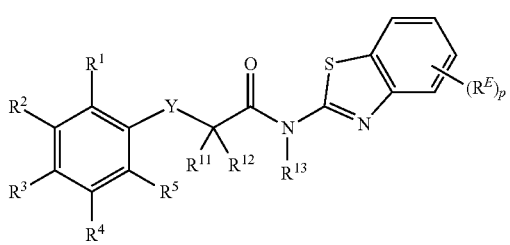

IV-a1 or a pharmaceutically acceptable form thereof.

In certain embodiments, a compound of formula I is of formula IV-a2:

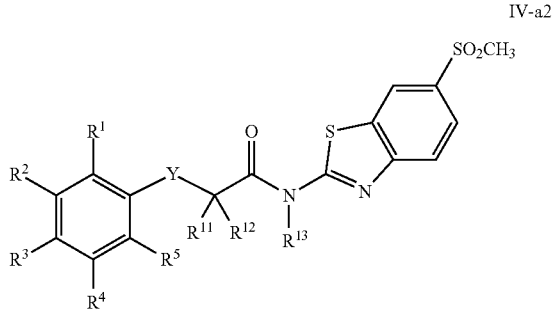

IV-a2 or a pharmaceutically acceptable form thereof.

In certain embodiments, a compound of formula I is of formula IV-a3:

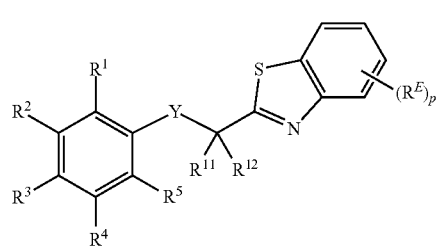

IV-a3 or a pharmaceutically acceptable form thereof.

In certain embodiments, a compound of formula I is of formula IV-a4:

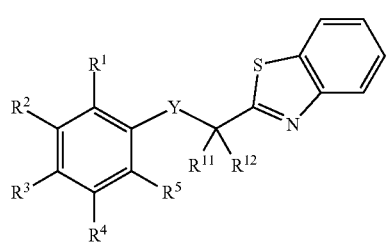

IV-a4 or a pharmaceutically acceptable form thereof.

In certain embodiments, a compound of formula I is of formula IV-b:

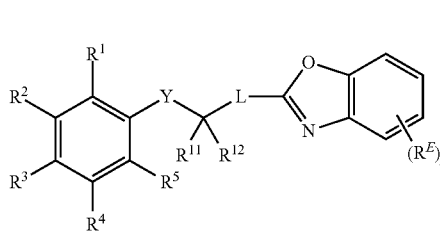

IV-b

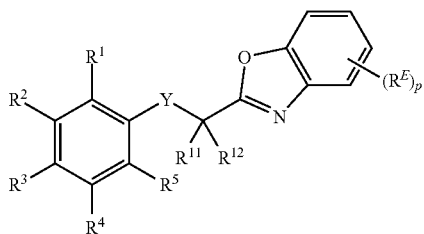

IV-b1 or a pharmaceutically acceptable form thereof.

In certain embodiments, a compound of formula I is of formula IV-b1:
or a pharmaceutically acceptable form thereof.

In certain embodiments, a compound of formula I is of formula IV-b2:

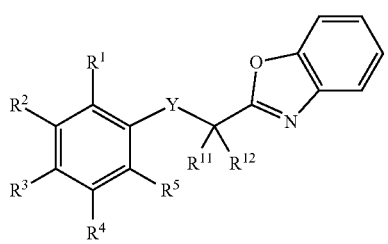

IV-b2 or a pharmaceutically acceptable form thereof.

In certain embodiments, a compound of formula I is of formula V:

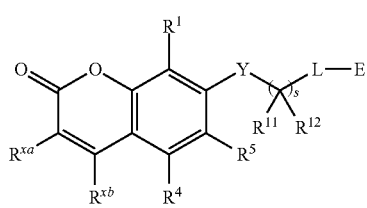

V or a pharmaceutically acceptable form thereof,
wherein:
each of $R^{xa}$ and $R^{xb}$ is independently hydrogen, halogen, or optionally substituted alkyl.

In certain embodiments, a compound of formula I is of formula V-a:

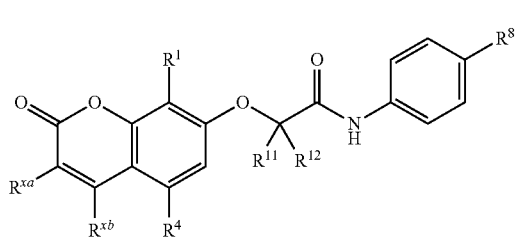

V-a or a pharmaceutically acceptable form thereof.

In certain embodiments, a compound of formula I is of formula V-a1:

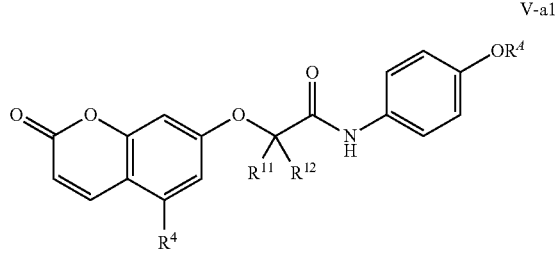

V-a1 or a pharmaceutically acceptable form thereof.

In certain embodiments, the present invention provides compounds of formula VI:

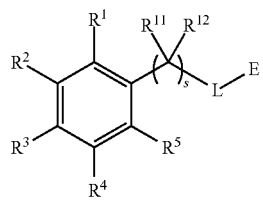

VI or pharmaceutically acceptable forms (e.g., pharmaceutically acceptable salts) thereof, wherein $R^1$, $R^2$, $R^3$, $R^4$, $R^5$, $R^{11}$, $R^{12}$, L, E, and s are as defined herein.

In certain embodiments, the present invention provides compounds of formula VI-a:

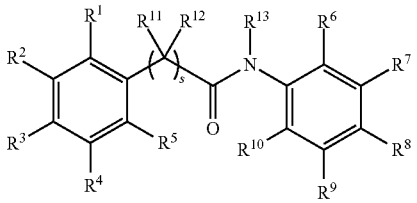

VI-a or pharmaceutically acceptable forms (e.g., pharmaceutically acceptable salts) thereof, wherein $R^1$, $R^2$, $R^3$, $R^4$, $R^5$, $R^6$, $R^7$, $R^8$, $R^9$, $R^{10}$, $R^{11}$, $R^{12}$, and s are as defined herein.

In certain embodiments, a compound of any one of Formula I-VI is not:

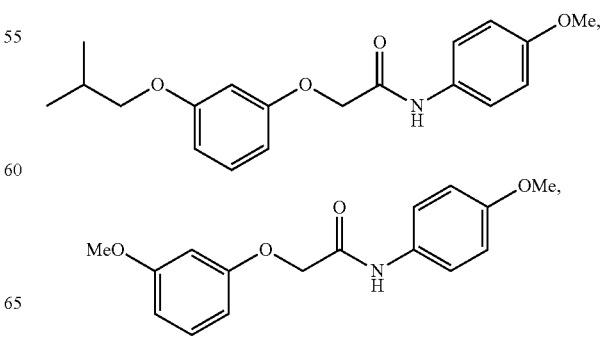

-continued

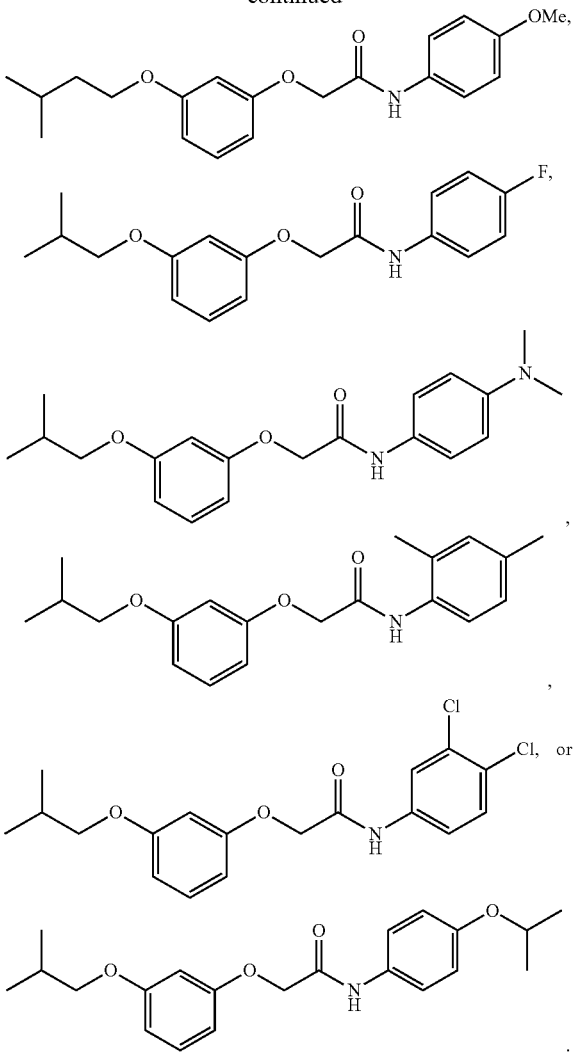

As generally defined above, L is a bond, —NR¹³C(=O)—, or —C(=O)NR¹³—. In certain embodiments, L is a bond. In certain embodiments, L is —NR¹³C(=O)—. In certain embodiments, L is —C(=O)NR¹³—. In certain embodiments, L is —NHC(=O)—. In certain embodiments, L is —C(=O)NH—. In certain embodiments, L is —N(CH₃)—C(=O)—. In certain embodiments, L is —C(=O)—N(CH₃)—. In certain embodiments, L is —N(C₂H₅)—C(=O)—. In certain embodiments, L is —C(=O)—N(C₂H₅)—.

As generally defined above, E is optionally substituted aryl or optionally substituted heteroaryl. In certain embodiments, E is optionally substituted aryl. In certain embodiments, E is of the formula

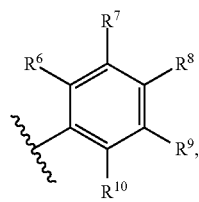

wherein $R^6$, $R^7$, $R^8$, $R^9$, and $R^{10}$ are independently selected from the group consisting of hydrogen, halo, —CN, —NO₂, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^A$, —N(R$^B$)₂, —SR$^A$, —C(=O)R$^A$, —C(=O)OR$^A$, —C(=O)SR$^A$, —C(=O)N(R$^B$)₂, —OC(=O)R$^A$, —NR$^B$C(=O)R$^A$, —NR$^B$C(=O)N(R$^B$)₂, —OC(=O)OR$^A$, —NR$^B$C(=O)OR$^A$, —OC(=O)N(R$^B$)₂, —SC(=O)R$^A$, —C(=NR$^B$)R$^A$, —C(=NR$^B$)N(R$^B$)₂, —NR$^B$C(=NR$^B$)R$^B$, —C(=S)R$^A$, —C(=S)N(R$^B$)₂, —NR$^B$C(=S)R$^A$, —S(=O)R$^A$, —SO₂R$^A$, —NR$^B$SO₂R$^A$, and —SO₂N(R$^B$)₂.

In some embodiments, $R^6$ is hydrogen. In some embodiments, $R^6$ is not hydrogen.

In some embodiments, $R^7$ is hydrogen. In some embodiments, $R^7$ is not hydrogen.

In some embodiments, $R^8$ is hydrogen. In some embodiments, $R^8$ is not hydrogen.

In some embodiments, $R^9$ is hydrogen. In some embodiments, $R^9$ is not hydrogen.

In some embodiments, $R^{10}$ is hydrogen. In some embodiments, $R^{10}$ is not hydrogen.

In certain embodiments, $R^6$ and $R^{10}$ are hydrogen. In certain embodiments, $R^6$, $R^7$, and $R^{10}$ are hydrogen. In certain embodiments, $R^6$, $R^7$, and $R^9$ are hydrogen. In certain embodiments, $R^7$, $R^9$, and $R^{10}$ are hydrogen. In certain embodiments, $R^6$, $R^9$, and $R^{10}$ are hydrogen.

In certain embodiments, $R^8$ is optionally substituted alkyl, e.g., $C_{1-10}$ alkyl. In certain embodiments, $R^8$ is optionally substituted $C_{1-8}$ alkyl, optionally substituted $C_{1-6}$ alkyl, optionally substituted $C_{1-4}$ alkyl, optionally substituted $C_{1-2}$ alkyl, optionally substituted $C_{2-8}$ alkyl, optionally substituted $C_{2-6}$ alkyl, or optionally substituted $C_{2-4}$ alkyl. In certain embodiments, R is methyl, ethyl, propyl, or butyl.

In certain embodiments, $R^8$ is optionally substituted alkenyl, e.g., $C_{2-10}$ alkenyl. In certain embodiments, $R^8$ is optionally substituted $C_{2-8}$ alkenyl, optionally substituted $C_{2-6}$ alkenyl, optionally substituted $C_{2-4}$ alkenyl, or optionally substituted $C_{2-3}$ alkenyl.

In certain embodiments, $R^8$ is optionally substituted alkynyl, e.g., $C_{2-10}$ alkynyl. In certain embodiments, $R^8$ is optionally substituted $C_{2-8}$ alkynyl, optionally substituted $C_{2-6}$ alkynyl, optionally substituted $C_{2-4}$ alkynyl, or optionally substituted $C_{2-3}$ alkynyl.

In certain embodiments, $R^8$ is optionally substituted carbocyclyl, e.g., $C_{3-10}$ carbocyclyl. In certain embodiments, $R^8$ is optionally substituted $C_{3-8}$carbocyclyl, optionally substituted $C_{4-8}$carbocyclyl, optionally substituted $C_{5-8}$carbocyclyl, optionally substituted $C_{5-7}$carbocyclyl, or optionally substituted $C_{5-6}$carbocyclyl.

In certain embodiments, $R^8$ is optionally substituted heterocyclyl, e.g., a 5- to 10-membered optionally substituted heterocyclyl. In certain embodiments, $R^8$ is a 5- to 8-membered optionally substituted heterocyclyl, a 5- to 7-membered optionally substituted heterocyclyl, or a 5- to 6-membered optionally substituted heterocyclyl.

In certain embodiments, $R^8$ is optionally substituted aryl, e.g., $C_6$ aryl or $C_{10}$ aryl. In certain embodiments, $R^8$ is optionally substituted $C_6$ aryl (i.e., phenyl). In certain embodiments, $R^8$ is optionally substituted $C_{10}$ aryl (i.e., napthyl).

In certain embodiments, $R^8$ is optionally substituted heteroaryl, e.g., a 5- to 10-membered optionally substituted heteroaryl. In certain embodiments, $R^8$ is a 5-membered optionally substituted heteroaryl, or a 6-membered optionally substituted heteroaryl.

In certain embodiments, $R^8$ is —$OR^A$. In certain embodiments, $R^8$ is —$OR^A$, wherein $R^A$ is alkyl. In certain embodiments, $R^8$ is —$OR^A$, wherein $R^A$ is $C_{1-6}$ alkyl. In certain embodiments, $R^8$ is —$OR^A$, wherein $R^A$ is $C_{1-3}$ alkyl. In certain embodiments, $R^8$ is —$OCH_3$.

In some embodiments, $R^8$ is —OEt. In some embodiments, $R^8$ is —OPr. In some embodiments, $R^8$ is —OiPr.

In certain embodiments, R is —$SO_2R^A$. In certain embodiments, $R^8$ is —$SO_2R^A$, wherein $R^A$ is alkyl. In certain embodiments, R is —$SO_2R^A$, wherein $R^A$ is $C_{1-6}$ alkyl. In certain embodiments, $R^8$ is —$SO_2R^A$, wherein $R^A$ is $C_{1-3}$ alkyl. In certain embodiments, $R^8$ is —$SO_2CH_3$. In some embodiments, $R^8$ is —$SO_2$Et. In some embodiments, $R^8$ is —$SO_2$Pr. In some embodiments, $R^8$ is —$SO_2$iPr.

In certain embodiments, $R^8$ is halo. In certain embodiments, $R^8$ is fluoro. In certain embodiments, $R^8$ is chloro. In certain embodiments, $R^8$ is bromo.

In certain embodiments, $R^8$ is —$N(R^B)_2$. In certain embodiments, $R^8$ is —$N(R^B)_2$, wherein $R^B$ is alkyl. In certain embodiments, $R^8$ is —$N(R^B)_2$, wherein $R^B$ is $C_{1-6}$ alkyl. In certain embodiments, $R^8$ is —$N(R^B)_2$, wherein $R^B$ is $C_{1-3}$ alkyl. In certain embodiments, $R^8$ is —$N(CH_3)_2$.

In certain embodiments, E is optionally substituted heteroaryl. In certain embodiments, E is substituted heteroaryl. In certain embodiments, E is unsubstituted heteroaryl. In certain embodiments, E is optionally substituted 5-membered heteroaryl. In certain embodiments, E is optionally substituted 6-membered heteroaryl. In certain embodiments, E is optionally substituted bicyclic heteroaryl. In certain embodiments, E is an optionally substituted monocyclic heteroaryl ring fused with an optionally substituted monocyclic aryl ring. In certain embodiments, E is an optionally substituted monocyclic heteroaryl ring fused with another optionally substituted monocyclic heteroaryl ring. E may be an optionally substituted 6,5-membered heteroaryl ring or an optionally substituted 5,6-membered heteroaryl ring. In certain embodiments, E is of the formula

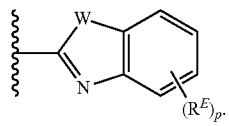

In certain embodiments, W is —O—. In certain embodiments, W is —S—. In certain embodiments, E is of the formula

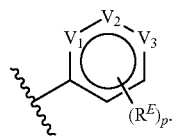

As generally defined herein, each instance of $V_1$, $V_2$, and $V_3$ is independently N or C, provided that at least one of $V_1$, $V_2$, and $V_3$ is N. In certain embodiments, $V_1$ is N, and $V_2$ and $V_3$ are C. In certain embodiments, $V_2$ is N, and $V_1$ and $V_3$ are C. In certain embodiments, $V_3$ is N, and $V_1$ and $V_2$ are C.

As generally defined herein, each instance of $R^E$ is independently selected from the group consisting of hydrogen, halo, —CN, —$NO_2$, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^A$, —$N(R^B)_2$, —$SR^A$, —C(=O) $R^A$, —C(=O)$OR^A$, —C(=O)$SR^A$, —C(=O)$N(R^B)_2$, —OC (=O)$R^A$, —$NR^B$C(=O)$R^A$, —$NR^B$C(=O)$N(R^B)_2$, —OC (=O)$OR^A$, —$NR^B$C(=O)$OR^A$, —OC(=O)$N(R^B)_2$, —SC (=O)$R^A$, —C(=$NR^B$)$R^A$, —C(=$NR^B$)$N(R^B)_2$, —$NR^B$C (=$NR^B$)$R^B$, —C(=S)$R^A$, —C(=S)$N(R^B)_2$, —$NR^B$C(=S) $R^A$, —S(=O)$R^A$, —$SO_2R^A$, —$NR^B SO_2 R^A$, and —$SO_2$N $(R^B)_2$.

In certain embodiments, $R^E$ is optionally substituted alkyl, e.g., $C_{1-10}$ alkyl. In certain embodiments, $R^E$ is optionally substituted $C_{1-8}$ alkyl, optionally substituted $C_{1-6}$ alkyl, optionally substituted $C_{1-4}$ alkyl, optionally substituted $C_{1-2}$ alkyl, optionally substituted $C_{2-8}$ alkyl, optionally substituted $C_{2-6}$ alkyl, or optionally substituted $C_{2-4}$ alkyl. In certain embodiments, $R^E$ is methyl, ethyl, propyl, or butyl.

In certain embodiments, $R^E$ is optionally substituted alkenyl, e.g., $C_{2-10}$ alkenyl. In certain embodiments, $R^E$ is optionally substituted $C_{2-8}$ alkenyl, optionally substituted $C_{2-6}$ alkenyl, optionally substituted $C_{2-4}$ alkenyl, or optionally substituted $C_{2-3}$ alkenyl.

In certain embodiments, $R^E$ is optionally substituted alkynyl, e.g., $C_{2-10}$ alkynyl. In certain embodiments, $R^E$ is optionally substituted $C_{2-8}$ alkynyl, optionally substituted $C_{2-6}$ alkynyl, optionally substituted $C_{2-4}$ alkynyl, or optionally substituted $C_{2-3}$ alkynyl.

In certain embodiments, RE is optionally substituted carbocyclyl, e.g., $C_{3-10}$carbocyclyl. In certain embodiments, $R^8$ is optionally substituted $C_{3-8}$carbocyclyl, optionally substituted $C_{4-8}$carbocyclyl, optionally substituted $C_{5-8}$carbocyclyl, optionally substituted $C_{5-7}$carbocyclyl, or optionally substituted $C_{5-6}$carbocyclyl.

In certain embodiments, $R^E$ is optionally substituted heterocyclyl, e.g., a 5- to 10-membered optionally substituted heterocyclyl. In certain embodiments, $R^E$ is a 5- to 8-membered optionally substituted heterocyclyl, a 5- to 7-membered optionally substituted heterocyclyl, or a 5- to 6-membered optionally substituted heterocyclyl.

In certain embodiments, $R^E$ is optionally substituted aryl, e.g., $C_6$ aryl or $C_{10}$ aryl.

In certain embodiments, $R^E$ is optionally substituted $C_6$ aryl (i.e., phenyl). In certain embodiments, $R^8$ is optionally substituted $C_{10}$ aryl (i.e., napthyl).

In certain embodiments, $R^E$ is optionally substituted heteroaryl, e.g., a 5- to 10-membered optionally substituted heteroaryl. In certain embodiments, $R^E$ is a 5-membered optionally substituted heteroaryl, or a 6-membered optionally substituted heteroaryl.

In certain embodiments, $R^E$ is —$OR^A$. In certain embodiments, $R^E$ is —$OR^A$, wherein $R^A$ is alkyl. In certain embodiments, $R^E$ is —$OR^A$, wherein $R^A$ is $C_{1-6}$ alkyl. In certain embodiments, $R^E$ is —$OR^A$, wherein $R^A$ is $C_{1-3}$ alkyl. In certain embodiments, $R^E$ is —$OCH_3$. In some embodiments, $R^E$ is —OEt. In some embodiments, $R^E$ is —OPr. In some embodiments, $R^E$ is —OiPr.

In certain embodiments, $R^E$ is —$SO_2R^A$. In certain embodiments, $R^E$ is —$SO_2R^A$ wherein $R^A$ is alkyl. In certain embodiments, $R^E$ is —$SO_2R^A$, wherein $R^A$ is $C_{1-6}$ alkyl. In certain embodiments, $R^E$ is —$SO_2R^A$, wherein $R^A$ is $C_{1-3}$ alkyl. In certain embodiments, $R^E$ is —$SO_2CH_3$. In some embodiments, $R^E$ is —$SO_2$Et. In some embodiments, $R^E$ is —$SO_2$Pr. In some embodiments, $R^E$ is —$SO_2$iPr.

In certain embodiments, $R^E$ is halo. In certain embodiments, $R^E$ is fluoro. In certain embodiments, $R^E$ is chloro. In certain embodiments, $R^E$ is bromo.

In certain embodiments, $R^E$ is —$N(R^B)_2$. In certain embodiments, $R^E$ is —$N(R^B)_2$, wherein $R^B$ is alkyl. In certain embodiments, $R^E$ is —N($R^B$)$_2$, wherein $R^B$ is $C_{1-6}$ alkyl. In certain embodiments, $R^E$ is —N($R^B$)$_2$, wherein $R^B$ is $C_{1-3}$ alkyl. In certain embodiments, $R^E$ is —N(CH$_3$)$_2$.

As generally defined herein, p is 0, 1, 2, 3, 4, or 5 as valency permits. In certain embodiments, p is 0. In certain embodiments, p is 1. In certain embodiments, p is 2. In certain embodiments, p is 3. In certain embodiments, p is 4. In certain embodiments, p is 5. In certain embodiments, p is 6.

In certain embodiments, E is of the formula

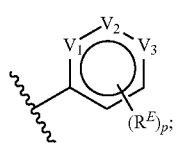

and p is 0. In certain embodiments, E is of the formula

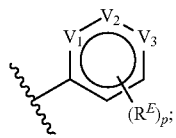

p is 1; and $R^E$ is alkyl or —OR$^A$. In certain embodiments, E is of the formula

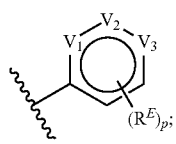

p is 2; and $R^E$ is alkyl or —OR$^A$. In certain embodiments, E is of the formula

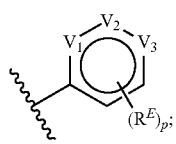

p is 3; and $R^E$ is alkyl or —OR$^A$. In certain embodiments, E is of the formula

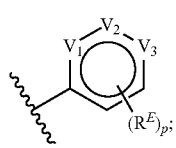

p is 4; and RE is alkyl or —OR$^A$. In certain embodiments, E is of the formula

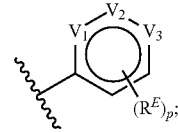

$V_1$ is N; $V_2$ and $V_3$ are C; p is 1; and $R^E$ is —O-alkyl. In certain embodiments, E is of the formula

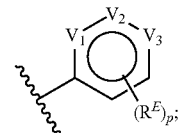

$V_1$ is N; $V_2$ and $V_3$ are C; p is 1; and $R^E$ is —O-methyl. In certain embodiments, E is of the formula

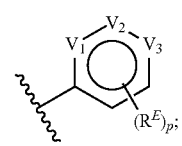

$V_2$ is N; $V_1$ and $V_3$ are C; p is 1; and $R^E$ is —OR$^A$. In certain embodiments, E is of the formula

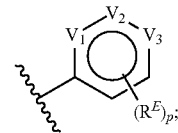

$V_2$ is N; $V_1$ and $V_3$ are C; p is 1; and $R^E$ is —O-alkyl. In certain embodiments, E is of the formula

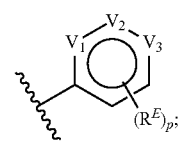

$V_2$ is N; $V_1$ and $V_3$ are C; p is 1; and $R^E$ is —O-methyl. In certain embodiments, E is of the formula

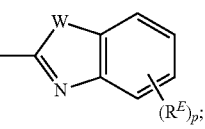

p is 0. In certain embodiments, E is of the formula

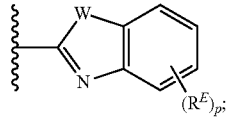

p is 1; and $R^E$ is halogen, alkyl, —$OR^A$, or —$SO_2R^A$. In certain embodiments, E is of the formula

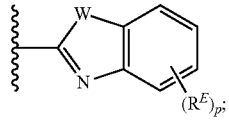

p is 2; and $R^E$ is halogen, alkyl, —$OR^A$, or —$SO_2R^A$. In certain embodiments, E is of the formula

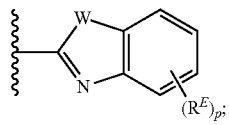

p is 3; and $R^E$ is halogen, alkyl, —$OR^A$, or —$SO_2R^A$. In certain embodiments, E is of the formula

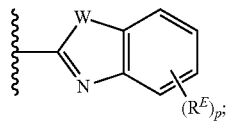

p is 4; and $R^E$ is halogen, alkyl, —$OR^A$, or —$SO_2R^A$. In certain embodiments, E is of the formula

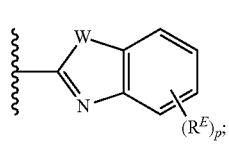

p is 5; and $R^E$ is halogen, alkyl, —$OR^A$, or —$SO_2R^A$. In certain embodiments, E is of the formula

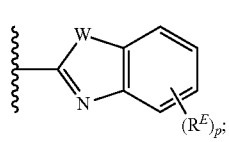

p is 1; and R is halogen, alkyl, —O-alkyl, or —$SO_2$-alkyl. In certain embodiments, E is of the formula

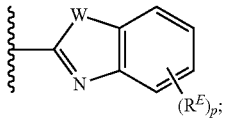

W is S; p is 1; and $R^E$ is halogen, alkyl, —O-alkyl, or —$SO_2$-alkyl. In certain embodiments, E is of the formula

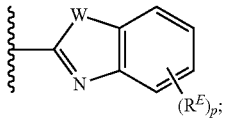

W is S; p is 1; and $R^E$ is —$SO_2$-alkyl. In certain embodiments, E is of the formula

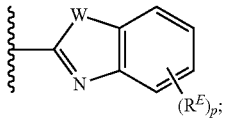

W is O; p is 1; and $R^E$ is halogen, alkyl, —O-alkyl, or —$SO_2$— alkyl.

As generally defined above, $R^1$, $R^3$, $R^4$, and $R^5$ are independently selected from the group consisting of hydrogen, halo, —CN, —$NO_2$, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —$OR^A$, —$N(R^B)_2$, —$SR^A$, —C(=O)$R^A$, —C(=O)$OR^A$, —C(=O)$SR^A$, —C(=O)$N(R^B)_2$, —OC(=O)$R^A$, —$NR^BC$(=O)$R^A$, —$NR^BC$(=O)$N(R^B)_2$, —OC(=O)$OR^A$, —$NR^BC$(=O)$OR^A$, —OC(=O)$N(R^B)_2$, —SC(=O)$R^A$, —C(=$NR^B$)$R^A$, —C(=$NR^B$)$N(R^B)_2$, —$NR^BC$(=$NR^B$)$R^B$, —C(=S)$R^A$, —C(=S)$N(R^B)_2$, —$NR^BC$(=S)$R^A$, —S(=O)$R^A$, —$SO_2R^A$, —$NR^BSO_2R^A$, and —$SO_2N(R^B)_2$.

In some embodiments, $R^1$ is hydrogen. In some embodiments, $R^1$ is not hydrogen. In certain embodiments, $R^1$ is $CF_3$.

In some embodiments, $R^2$ is hydrogen. In some embodiments, $R^2$ is not hydrogen.

In some embodiments, $R^3$ is hydrogen. In some embodiments, $R^3$ is not hydrogen. In certain embodiments, $R^3$ is optionally substituted alkyl, e.g., $C_{1-10}$ alkyl. In certain embodiments, $R^3$ is optionally substituted $C_{5-8}$ alkyl, optionally substituted $C_{1-6}$ alkyl, optionally substituted $C_{1-4}$ alkyl, optionally substituted $C_{1-2}$ alkyl, optionally substituted $C_{2-8}$ alkyl, optionally substituted $C_{2-6}$ alkyl, or optionally substituted $C_{2-4}$ alkyl. In certain embodiments, $R^3$ is methyl, ethyl, propyl, or butyl. In certain embodiments, $R^3$ is $CF_3$. In certain embodiments, $R^3$ is optionally substituted alkenyl, e.g., $C_{2-10}$ alkenyl. In certain embodiments, $R^3$ is optionally substituted $C_{2-8}$ alkenyl, optionally substituted $C_{2-6}$ alkenyl, optionally substituted $C_{2-4}$ alkenyl, or optionally substituted $C_{2-3}$ alkenyl. In certain embodiments, $R^3$ is —$OR^A$. In certain embodiments, $R^3$ is —$OR^A$, wherein $R^A$ is alkyl. In certain embodiments, $R^3$ is —$OR^A$, wherein $R^A$ is $C_{1-6}$ alkyl. In certain embodiments, $R^3$ is —$OR^A$, wherein $R^A$ is $C_{1-3}$ alkyl. In certain embodiments, $R^3$ is —$OCH_3$. In some embodiments, $R^3$ is —OEt. In some embodiments, $R^3$ is —OPr. In some embodiments, R is —OiPr. In certain embodiments, R is —SO$_2$R$^4$. In certain embodiments, $R^3$ is —SO$_2$R$^A$, wherein R$^A$ is alkyl. In certain embodiments, $R^3$ is —SO$_2$R$^A$, wherein R$^A$ is $C_{1-6}$ alkyl. In certain embodiments, $R^3$ is —SO$_2$R$^A$, wherein R$^A$ is $C_{1-3}$ alkyl. In certain embodiments, $R^3$ is —SO$_2$CH$_3$. In some embodiments, $R^3$ is —SO$_2$Et. In some embodiments, $R^3$ is —SO$_2$Pr. In some embodiments, $R^3$ is —SO$_2$iPr. In certain embodiments, $R^3$ is halo. In certain embodiments, $R^3$ is fluoro. In certain embodiments, $R^3$ is chloro. In certain embodiments, $R^3$ is bromo.

In some embodiments, $R^4$ is hydrogen. In some embodiments, $R^4$ is not hydrogen. In certain embodiments, $R^4$ is optionally substituted alkyl, e.g., $C_{1-10}$ alkyl. In certain embodiments, $R^4$ is optionally substituted $C_{5-8}$ alkyl, optionally substituted $C_{1-6}$ alkyl, optionally substituted $C_{1-4}$ alkyl, optionally substituted $C_{1-2}$ alkyl, optionally substituted $C_{2-8}$ alkyl, optionally substituted $C_{2-6}$ alkyl, or optionally substituted $C_{2-4}$ alkyl. In certain embodiments, $R^4$ is methyl, ethyl, propyl, or butyl. In certain embodiments, $R^4$ is CF$_3$. In certain embodiments, $R^4$ is halo. In certain embodiments, $R^4$ is fluoro. In certain embodiments, $R^4$ is chloro. In certain embodiments, $R^4$ is bromo.

In some embodiments, $R^5$ is hydrogen. In some embodiments, $R^5$ is not hydrogen.

In certain embodiments, $R^1$, $R^3$, $R^4$, and $R^5$ are hydrogen. In certain embodiments, $R^1$, $R^3$, and $R^4$ are hydrogen. In certain embodiments, $R^1$, $R^2$, and $R^4$ are hydrogen.

As described generally above, $R^2$ is halogen, or —O—Rx, wherein $R^X$ is optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, or optionally substituted heteroaralkyl. In certain embodiments, $R^2$ is hydrogen.

In certain embodiments, $R^X$ is optionally substituted alkyl, e.g., $C_{1-10}$ alkyl. In certain embodiments, $R^X$ is optionally substituted $C_{1-8}$ alkyl, optionally substituted $C_{1-6}$ alkyl, optionally substituted $C_{1-4}$ alkyl, optionally substituted $C_{1-2}$ alkyl, optionally substituted $C_{2-8}$ alkyl, optionally substituted $C_{2-6}$ alkyl, or optionally substituted $C_{2-4}$ alkyl. In certain embodiments, $R^X$ is $C_3$-$C_8$ alkyl. In certain embodiments, $R^X$ is $C_4$-$C_6$ alkyl. In certain embodiments, $R^X$ is $C_4$ alkyl. In certain embodiments, $R^X$ is isobutyl. In certain embodiments, $R^X$ is $C_5$ alkyl. In certain embodiments, $R^X$ is isopentyl. In some embodiments, $R^X$ is n-butyl or sec-butyl. In some embodiments, $R^X$ is alkylcycloalkyl (e.g., cyclopropylmethyl). In some embodiments, $R^X$ is a substituted alkyl group. In some embodiments, $R^X$ is substituted one or more times with fluorine.

In certain embodiments, $R^X$ is optionally substituted alkenyl, e.g., $C_{2-10}$ alkenyl. In certain embodiments, $R^X$ is optionally substituted $C_{2-8}$ alkenyl, optionally substituted $C_{2-6}$ alkenyl, optionally substituted $C_{2-4}$ alkenyl, or optionally substituted $C_{2-3}$ alkenyl.

In certain embodiments, $R^X$ is optionally substituted alkynyl, e.g., $C_{2-10}$ alkynyl. In certain embodiments, $R^X$ is optionally substituted $C_{2-8}$ alkynyl, optionally substituted $C_{2-6}$ alkynyl, optionally substituted $C_{2-4}$ alkynyl, or optionally substituted $C_{2-3}$ alkynyl.

In certain embodiments, $R^X$ is optionally substituted carbocyclyl, e.g., $C_{3-10}$carbocyclyl. In certain embodiments, $R^X$ is optionally substituted $C_{3-8}$carbocyclyl, optionally substituted $C_{4-8}$carbocyclyl, optionally substituted $C_{5-8}$carbocyclyl, optionally substituted $C_{5-7}$carbocyclyl, or optionally substituted $C_{5-6}$carbocyclyl. In some embodiments, $R^X$ is cyclopropyl, cyclobutyl, cyclopentyl, or cyclohexyl.

In certain embodiments, $R^X$ is optionally substituted heterocyclyl, e.g., a 5- to 10-membered optionally substituted heterocyclyl. In certain embodiments, $R^X$ is a 5- to 8-membered optionally substituted heterocyclyl, a 5- to 7-membered optionally substituted heterocyclyl, or a 5- to 6-membered optionally substituted heterocyclyl.

In certain embodiments, $R^X$ is optionally substituted aryl, e.g., $C_6$ aryl or $C_{10}$ aryl. In certain embodiments, $R^X$ is optionally substituted $C_6$ aryl (i.e., phenyl). In certain embodiments, $R^X$ is optionally substituted $C_{10}$ aryl (i.e., napthyl).

In certain embodiments, $R^X$ is optionally substituted heteroaryl, e.g., a 5- to 10-membered optionally substituted heteroaryl. In certain embodiments, $R^X$ is a 5-membered optionally substituted heteroaryl, or a 6-membered optionally substituted heteroaryl. In certain embodiments, $R^X$ is a 5- or 6-membered heteroaryl having 1-3 heteroatoms selected from nitrogen, oxygen, and sulfur. In certain embodiments, $R^X$ is a 6-membered heteroaryl having 1-3 nitrogens. In certain embodiments, $R^X$ is pyridyl. In some embodiments, $R^X$ is pyrimidyl, pyrazinyl, or triazinyl.

In certain embodiments, $R^X$ is optionally substituted aralkyl. In certain embodiments, $R^X$ is optionally substituted benzyl. In certain embodiments, $R^X$ is unsubstituted benzyl. In certain embodiments, $R^X$ is optionally substituted heteroaralkyl.

In certain embodiments, $R^X$ and $R^3$ are taken together with their intervening atoms to form an optionally substituted heterocyclic ring. In certain embodiments, a compound of formula (I) is of formula V As described generally above, $R^{11}$ and $R^{12}$ are independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, or optionally substituted heteroaralkyl. In certain embodiments, $R^{11}$ is hydrogen. In certain embodiments, $R^{12}$ is hydrogen. In certain embodiments, both $R^{11}$ and $R^{12}$ are hydrogen. In certain embodiments, one of $R^{11}$ and $R^{12}$ is hydrogen. In certain embodiments, at least one of $R^{11}$ and $R^{12}$ is hydrogen. In certain embodiments, $R^{11}$ is methyl and $R^{12}$ is hydrogen.

In certain embodiments, Y is a bond. In certain embodiments, Y is —O—. In certain embodiments, Y is —S—.

As described generally above, $R^{13}$ is hydrogen or $C_{1-6}$ alkyl. In certain embodiments, $R^{13}$ is hydrogen. In certain embodiments, $R^{13}$ is $C_{1-6}$ alkyl. In certain embodiments, $R^{13}$ is methyl, ethyl, propyl, or butyl. In certain embodiments, $R^{13}$ is methyl.

In certain embodiments, a provided compound is any one of the following formulae:

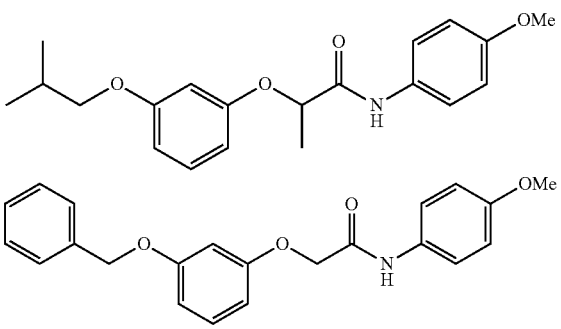

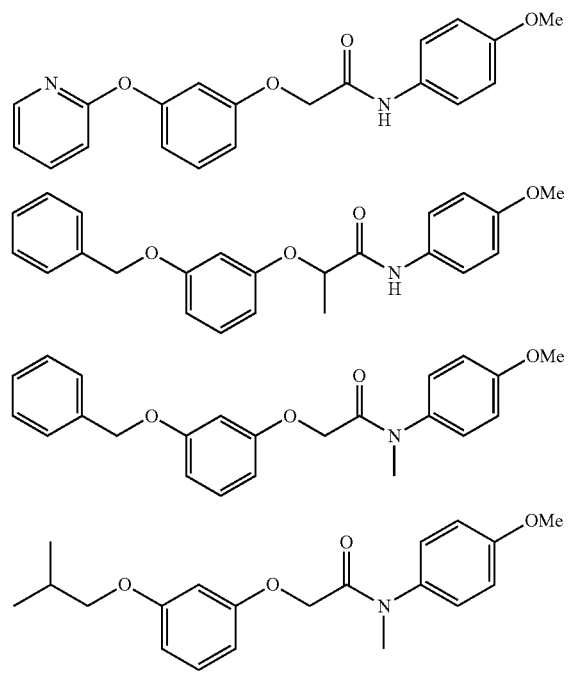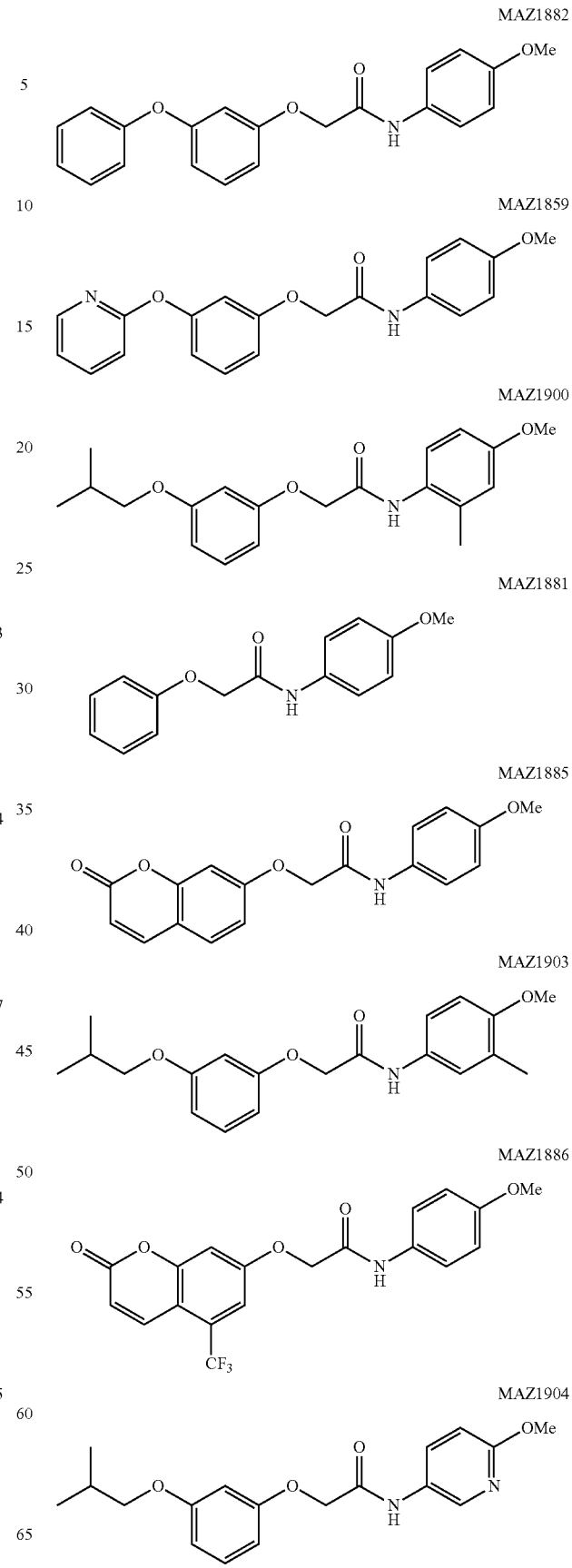

-continued
MAZ1883
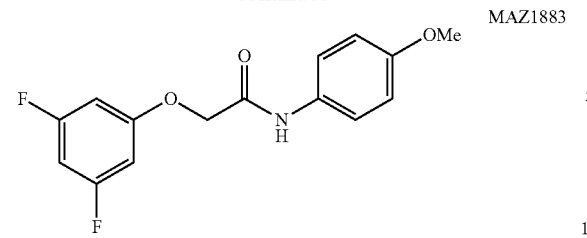
MAZ1905
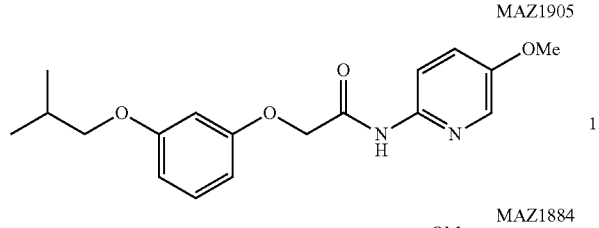
MAZ1884
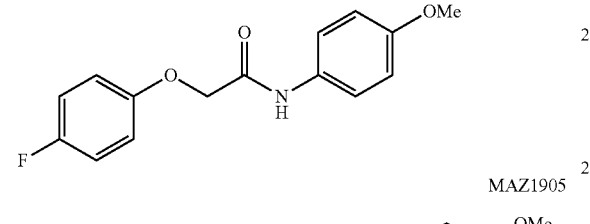
MAZ1905
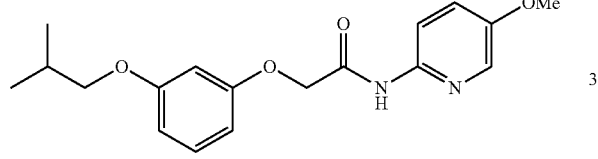
MAZ1884
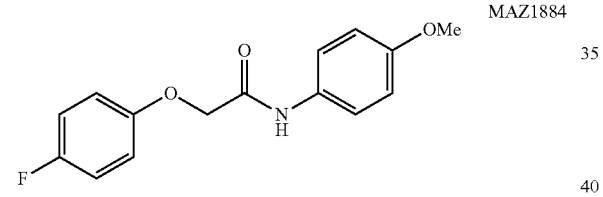
MAZ839
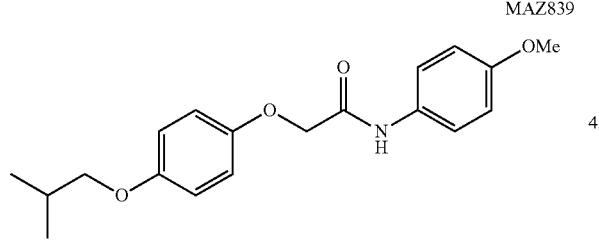
MAZ1909
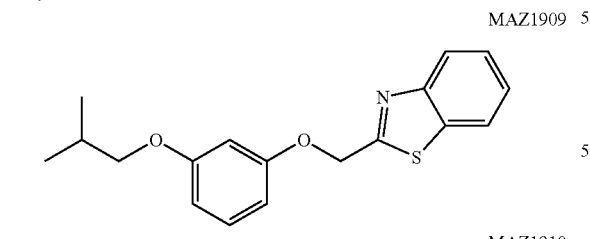
MAZ1910
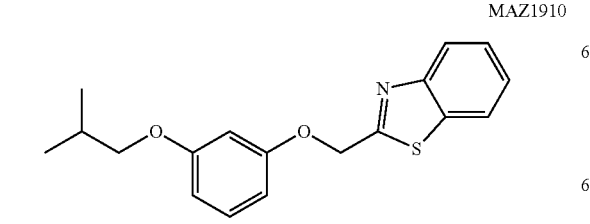
-continued
MAZ1911
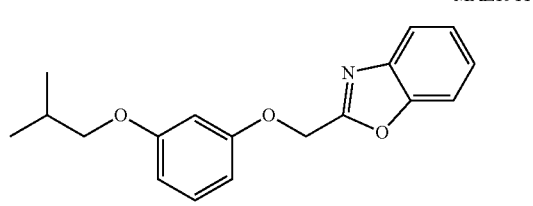
CM1 T0501-2364
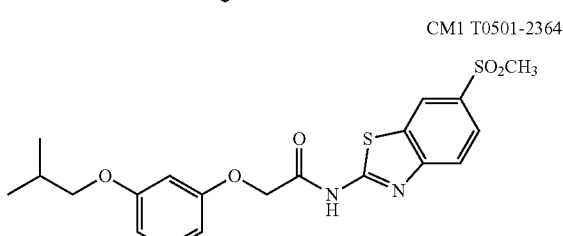
MAZ1887
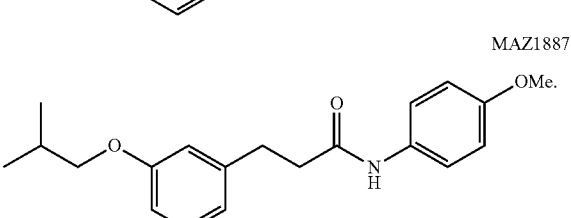
In certain embodiments, a compound useful in methods described herein is:
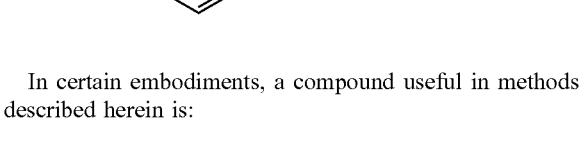
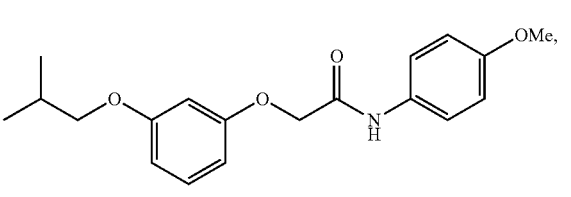
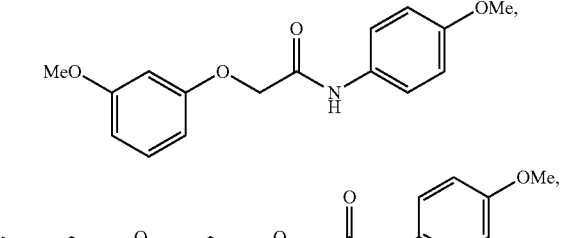
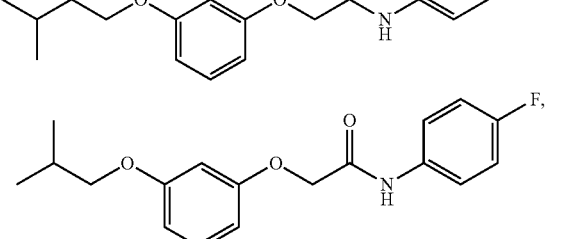
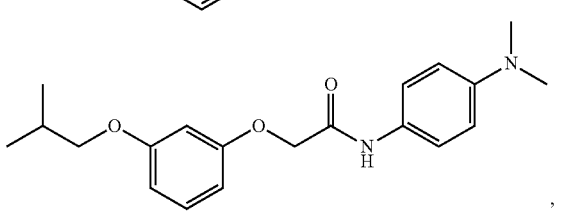

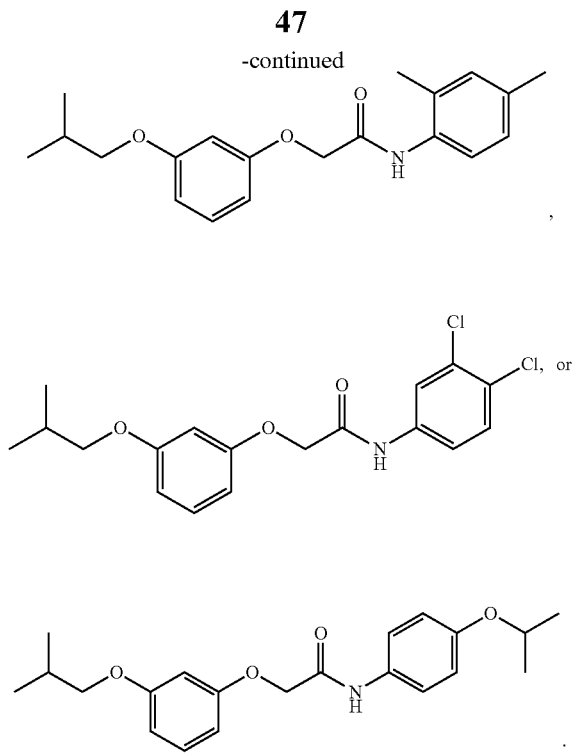

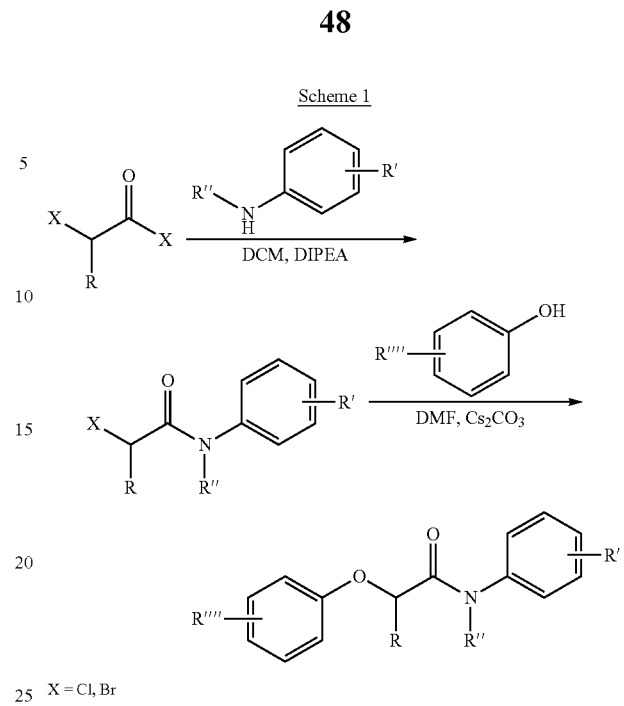

Scheme 1

In certain embodiments, a compound useful in methods described herein is:

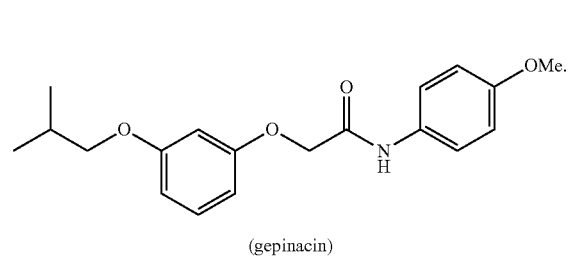 [SMILES: COc1ccc(NC(=O)COc2cccc(OCC(C)C)c2)cc1]

(gepinacin)

In certain embodiments, a compound useful in methods described herein inhibits Gwt1, or a mutant or variant thereof. In certain embodiments, the compound inhibits Gwt1, or a mutant or variant thereof, at an EC50 less than 40 μM. In certain embodiments, the compound inhibits Gwt1, or a mutant or variant thereof, at an EC50 less than 10 μM. In certain embodiments, the compound inhibits Gwt1, or a mutant or variant thereof, at an EC50 less than 5 μM. In certain embodiments, the compound inhibits Gwt1, or a mutant or variant thereof, at an EC50 less than 1 μM. In certain embodiments, the compound inhibits Gwt1, or a mutant or variant thereof, at an EC50 less than 0.5 μM. In certain embodiments, the compound is selective for Gwt1 when compared with its human ortholog, PigW. In certain embodiments, the compound is at least 10 times more active against Gwt1 than PigW. In certain embodiments, the compound is at least 5 times more active against Gwt1 than PigW. In certain embodiments, the compound is at least 2 times more active against Gwt1 than PigW. In certain embodiments, the compound is inactive against PigW at concentrations up to 40 μM.

In some embodiments, compounds of Formula (I) can be prepared using methods shown in Scheme 1 or Scheme 2. An exemplary synthetic scheme of compound MAZ1887 is shown in Scheme 3.

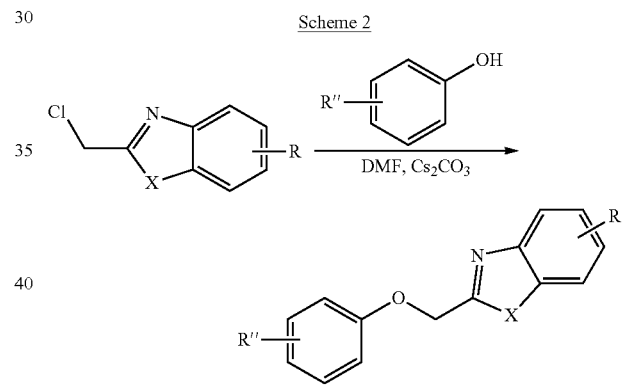

Scheme 2

X = O, S, NR'

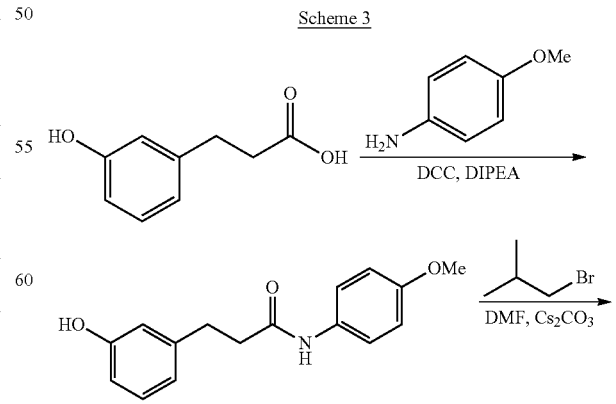

Scheme 3

-continued

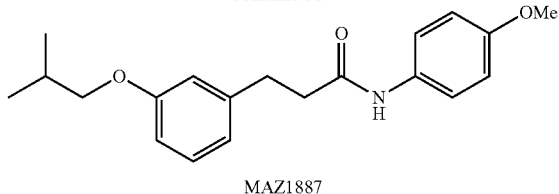

MAZ1887

Pharmaceutical Compositions and Administration

The present invention provides pharmaceutical compositions comprising a compound described herein, e.g., a compound of Formula I, or a pharmaceutically acceptable form thereof, as described herein, and optionally a pharmaceutically acceptable excipient. In certain embodiments, the compound of the present invention, or a pharmaceutically acceptable form thereof, is provided in an effective amount in the pharmaceutical composition. In certain embodiments, the effective amount is a therapeutically effective amount. In certain embodiments, the effective amount is an amount effective for treating a fungal infection. In certain embodiments, the effective amount is an amount effective for treating a parasitic infection. In certain embodiments, the effective amount is a prophylactically effective amount. In certain embodiments, the effective amount is an amount effective to prevent a fungal infection. In certain embodiments, the effective amount is an amount effective to prevent a parasitic infection.

Pharmaceutically acceptable excipients include any and all solvents, diluents, or other liquid vehicles, dispersions, suspension aids, surface active agents, isotonic agents, thickening or emulsifying agents, preservatives, solid binders, lubricants, and the like, as suited to the particular dosage form desired. General considerations in formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21st Edition (Lippincott Williams & Wilkins, 2005).

Pharmaceutical compositions described herein can be prepared by any method known in the art of pharmacology. In general, such preparatory methods include the steps of bringing the compound of the present invention (the "active ingredient") into association with a carrier and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable excipient, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, and mixtures thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, and mixtures thereof.

Exemplary surface active agents and/or emulsifiers include natural emulsifiers (e.g., acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g., bentonite (aluminum silicate) and Veegum (magnesium aluminum silicate)), long chain amino acid derivatives, high molecular weight alcohols (e.g., stearyl alcohol, cetyl alcohol, oleyl alcohol, triacetin monostearate, ethylene glycol distearate, glyceryl monostearate, and propylene glycol monostearate, polyvinyl alcohol), carbomers (e.g., carboxy polymethylene, polyacrylic acid, acrylic acid polymer, and carboxyvinyl polymer), carrageenan, cellulosic derivatives (e.g., carboxymethylcellulose sodium, powdered cellulose, hydroxymethyl cellulose, hydroxypropyl cellulose, hydroxypropyl methylcellulose, methylcellulose), sorbitan fatty acid esters (e.g., polyoxyethylene sorbitan monolaurate (Tween 20), polyoxyethylene sorbitan (Tween 60), polyoxyethylene sorbitan monooleate (Tween 80), sorbitan monopalmitate (Span 40), sorbitan monostearate (Span 60], sorbitan tristearate (Span 65), glyceryl monooleate, sorbitan monooleate (Span 80)), polyoxyethylene esters (e.g., polyoxyethylene monostearate (Myrj 45), polyoxyethylene hydrogenated castor oil, polyethoxylated castor oil, polyoxymethylene stearate, and Solutol), sucrose fatty acid esters, polyethylene glycol fatty acid esters (e.g., Cremophor™), polyoxyethylene ethers, (e.g., polyoxyethylene lauryl ether (Brij 30)), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F68, Poloxamer 188, cetrimonium bromide, cetylpyridinium chloride, benzalkonium chloride, docusate sodium, and/or mixtures thereof.

Exemplary binding agents include starch (e.g., cornstarch and starch paste), gelatin, sugars (e.g., sucrose, glucose, dextrose, dextrin, molasses, lactose, lactitol, mannitol, etc.), natural and synthetic gums (e.g., acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch arabogalactan), alginates, polyethylene oxide, polyethylene glycol, inorganic calcium salts, silicic acid, polymethacrylates, waxes, water, alcohol, and/or mixtures thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, and mixtures thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, and mixtures thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and mixtures thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor™, alcohols, oils, modified oils, glycols, polysorbates, cyclodextrins, polymers, and mixtures thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polyethylene glycols and the like.

The active ingredient can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose, or starch. Such dosage forms may comprise, as is normal practice, additional substances other than inert diluents, e.g., tableting lubricants and other tableting aids such a magnesium stearate and microcrystalline cellulose. In the case of capsules, tablets, and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat. Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

Formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically-administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation.

Compounds provided herein are typically formulated in dosage unit form for ease of administration and uniformity of dosage. It will be understood, however, that the total daily usage of the compositions of the present invention will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), and/or the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder, and/or it may achieve different effects.

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually.

Exemplary additional therapeutically active agents include, but are not limited to, antimicrobial agents, antifungal agents, antiparasitic agents, anti-inflammatory agents, and a pain-relieving agent. Therapeutically active agents include small organic molecules such as drug compounds (e.g., compounds approved by the U.S. Food and Drug Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins, and cells.

In certain embodiments, the additional therapeutic agent is an antifungal agent. Exemplary antifungal agents include, but are not limited to, BIQ, E1210, amphotericin B, candidicin, filipin, hamycin, natamycin, nystatin, rimocidin, bifonazole, butoconazole, clotrimazole, enconazole, fenticonazole, isoconazole, ketoconazole, miconazole, omoconazole, oxiconazole, sertaconazole, sulconazole, tioconazole, albaconazole, fluconazole, isavuconazole, itraconazole, posaconazole, ravuconazole, terconazole, voriconazole, abafungin, amorolfin, butenafine, naftifine, terbinafine, anidulafungin, caspofungin, micafungin, benzoic acid, ciclopirox, flucytosine, griseofulvin, haloprogin, polygodial, tolanftate, undecylenic acid, crystal violet, piroctone olamine, and zinc pyrithione.

Also encompassed by the invention are kits (e.g., pharmaceutical packs). The kits provided may comprise an inventive pharmaceutical composition or compound and a container (e.g., a vial, ampule, bottle, syringe, and/or dispenser package, or other suitable container). In some embodiments, provided kits may optionally further include a second container comprising a pharmaceutical excipient for dilution or suspension of an inventive pharmaceutical composition or compound. In some embodiments, the inventive pharmaceutical composition or compound provided in the container and the second container are combined to form one unit dosage form.

Methods of Use and Treatment

Compounds and compositions described herein are generally useful for the inhibition of fungal or parasitic growth. In some embodiments, compounds and compositions described herein are useful in inhibiting of the activity of acyltransferases, e.g., Gwt1, or a mutant or variant thereof. In some embodiments, compounds and compositions described herein are useful in inhibiting GPI-anchor biosynthesis. In one aspect, methods of treating fungal infection in a subject are provided which comprise administering an effective amount of a compound described herein (e.g., a compound of Formula I), or a pharmaceutically acceptable form (e.g., pharmaceutically acceptable salt) thereof, to a subject in need of treatment. In certain embodiments, the effective amount is a therapeutically effective amount. In certain embodiments, the effective amount is a prophylactically effective amount. In certain embodiments, the subject is suffering from a fungal infection. In certain embodiments, the subject is susceptible to a fungal infection. In certain embodiments, the subject is suffering from a parasitic infection. In certain embodiments, the subject is susceptible to a parasitic infection. In certain embodiments, the subject is immunocompromised.

The present invention further provides a method of inhibiting an acyltransferase, the method comprising contacting an acyltransferase with a compound described herein (e.g., a compound of Formula I), or a pharmaceutically acceptable form (e.g., pharmaceutically acceptable salt) thereof, in an amount sufficient to inhibit the acyltransferase's activity. In some embodiments, the present invention provides a method of inhibiting Gwt 1, or a mutant or variant thereof, the method comprising contacting the Gwt1, or mutant or variant thereof, with a compound described herein (e.g., a compound of Formula I), or a pharmaceutically acceptable form thereof, in an amount sufficient to inhibit the activity of the Gwt1, or mutant or variant thereof. The Gwt1 may be purified or crude, and may be present in a cell, tissue, or subject. Thus, such methods encompasses both inhibition of in vitro and in vivo Gwt1 activity. In certain embodiments, the method is an in vitro method, e.g., such as an assay method useful as a research tool. Research tools contemplated may be assays in assessing a particular compound's inhibitory activity against Gwt1 or the GPI-anchor biosynthetic pathway, e.g., in the SAR study of the molecular scaffold.

In some embodiments, the present invention provides a method of inhibiting GPI-anchor biosynthesis in a cell, the method comprising contacting the cell with a compound described herein (e.g., a compound of Formula I), or a pharmaceutically acceptable form thereof, in an amount sufficient to inhibit GPI-anchor biosynthesis in the cell. In certain embodiments, the cell is a fungus. In certain embodiments, the cell is a parasite.

In some embodiments, the present invention provides a method of inhibiting fungal growth, the method comprising contacting a fungus with a compound described herein (e.g., a compound of Formula I), or a pharmaceutically acceptable form thereof, in an amount sufficient to inhibit growth of the fungus. The fungus may be any fungus including, but not limited to, a genus selected from the group consisting of Candida, Aspergillus, Coccidioides, Cryptococcus, Fusarium, Histoplasma, Mucor, Pneumocystis, Stachybotrys, and Saccharomyces. In certain embodiments, the fungus is Candida albicans, Candida glabrata, Candida rugosa, Candida parapsilosis, Candida tropicalis, Candida dubliniensis, Aspergillus fumigatus, Aspergillus flavus, Aspergillus clavatus, Aspergillus terreus, Coccidioides immitis, Cryptococcus neoformans, Cryptococcus laurentii, Cryptococcus albidus, Cryptococcus gattii, Fusarium solani, Histoplasma capsulatum, Mucor circinelloides, Pneumocystis jirovecii, Pneumocystis carinii, Stachybotrys chartarum, or Saccharomyces cerevisiae. In certain embodiments, the fungus is Candida albicans. In certain embodiments, the fungus is Aspergillus fumigatus. In certain embodiments, the fungus is Candida glabrata. In certain embodiments, the fungus is Aspergillus terreus. In certain embodiments, the fungus is a drug-resistant fungus. In certain embodiments, the fungus is an azole-resistant fungus. In certain embodiments, the fungus is resistant to fluconazole. In certain embodiments, the fungus is resistant to amphotericin B. In certain embodiments, the fungus is resistant to caspofungin. In certain embodiments, the fungus is fluconazole-resistant C. albicans. In certain embodiments, the fungus is amphotericin B-resistant C. albicans. In certain embodiments, the fungus is caspofungin-resistant C. albicans. In certain embodiments, the fungus is in a subject, and a therapeutically effective amount of the compound is administered to the subject. In certain embodiments, the subject is suffering from a fungal infection. In certain embodiments, the subject is susceptible to a fungal infection. In certain embodiments, the subject is immunocompromised.

In some embodiments, the present invention provides a method of inhibiting parasitic growth, the method comprising contacting a parasite with a compound described herein (e.g., a compound of Formula I), or a pharmaceutically acceptable form thereof, in an amount sufficient to inhibit growth of the parasite. The parasite may be any parasite including, but not limited to, a genus selected from the group consisting of Plasmodium, Trypanosoma, Entamoeba, Giardia, Leishmania, Toxoplasma, and Schistosoma. In certain embodiments, the parasite is Plasmodium falciparum, Plasmodium yoelii, Plasmodium berghei, Trypanosoma brucei, Trypanosoma cruzi, Entamoeba histolytica, Giardia lamblia, Leishmania major, Leishmania tropica, Leishmania aethiopica, Leishmania mexicana, Leishmania braziliensis, Leishmania donovani, Toxoplasma gondii, or Schistosoma mansonii. In certain embodiments, the parasite is Plasmodium falciparum. In certain embodiments, the parasite is Trypanosoma brucei. In certain embodiments, the parasite is Trypanosoma cruzi. In certain embodiments, the fungus is a drug-resistant parasite. In certain embodiments, the parasite is in a subject, and a therapeutically effective amount of the compound is administered to the subject. In certain embodiments, the subject is suffering from a parasitic infection. In certain embodiments, the subject is susceptible to a parasitic infection. In certain embodiments, the subject is immunocompromised.

Methods of Screening

The present invention also provides an assay to determine the inhibitory effect of a test compound on Gwt1. The assay comprises contacting Gwt1, or a mutant or variant thereof, with a compound described herein (e.g., a compound of Formula I), or a salt thereof, and determining whether the compound inhibits Gwt1, or a mutant or variant thereof.

In certain embodiments, the Gwt1 protein is a recombinant, full length Gwt1 protein. In other embodiments, the Gwt1 protein is a purified Gwt1 protein. In still other embodiments, the Gwt1 protein is a crude Gwt1 protein. In further embodiments, the Gwt1 protein is purified from natural sources. In other embodiments, the Gwt1 protein is a modified form of an Gwt1 protein. In other embodiments, the Gwt1 protein is a mutant form of an Gwt1 protein. In other embodiments, the Gwt1 protein is a truncated form of an Gwt1 protein. In still other embodiments, the Gwt1 protein is a truncated form of an Gwt1 protein which includes at least an active site.

In certain embodiments, a library of compounds of Formula I is screened for inhibition of Gwt1. In certain embodiments, multiple compounds are assayed in parallel. In other embodiments, at least 10 compounds are assayed in parallel. In still other embodiments, at least 50 compounds are assayed in parallel. In further embodiments, at least 100 compounds are assayed in parallel. In certain embodiments, at least 500 compounds are assayed in parallel. In other embodiments, at least 1000 compounds are assayed in parallel.

In certain embodiments, the compound or library of compounds is also screened against PigW, and selectivity for Gwt 1 compared with PigW is determined.

EXAMPLES

In order that the invention described herein may be more fully understood, the following examples are set forth. It should be understood that these examples are for illustrative purposes only and are not to be construed as limiting this invention in any manner.

In the course of high-throughput screening, the present inventors encountered a compound, gepinacin, that possessed anti-fungal activity against a surprisingly diverse range of fungi. Under screening conditions, the compound induced swelling of the yeast, Saccharomyces cerevisiae, which caused it to score in a cell growth assay. Closer examination revealed that gepinacin was actually toxic to yeast. In contrast, no growth inhibition was seen when gepinacin was incubated with mammalian cells in culture. The model fungal organism S. cerevisiae was used to identify the target of gepinacin and to understand the basis of its selective toxicity to fungi. Following target validation, gepinacin was used as a chemical probe to further characterize its mode of action and explore the therapeutic implications of target inhibition in azole-resistant isolates of the far less genetically tractable but more medically relevant fungal pathogen, C. albicans.

Preparation of the Compounds.

Compounds described herein may be synthesized according to Schemes 1 to 3 and/or methods known in the art, using known starting materials and equipment.

Compound MAZ1887 may be prepared by the following method: A solution of 2.26 g (20 mmol) chloroacetyl chloride in 5 mL THF was slowly added to a solution of 2.46 g (20 mmol) 4-methoxy aniline and 3.22 g (25 mmol) diisopropylethylamine (DIPEA) in 100 mL THF at 0° C. After 10 min the reaction mixture was warmed to room temperature, and ethyl acetate was added. The organic layer was washed with dilute HCl, brine, and saturated $NaHCO_3$, and dried over sodium sulfate. After removal of the solvent the reddish-white solids were washed with diethyl ether to yield the desired chloroacetyl anilide as off-white crystals in quantitative yield. An amount of 100 mg of the chloroacetyl anilide and 100 mg of 3-isobutoxyphenol were dissolved in 5 mL DMF followed by the addition of 500 mg cesium carbonate. The resulting mixture was heated for 2 hr at 60° C. After cooling to room temperature, diethyl ether was added, and the organic layer was washed with brine and diluted LiCl solution. After drying over sodium sulfate the solvent was removed, and the crude product was purified on silica with hexanes/ethyl acetate to afford MAZ1887.

Materials.

Gepinacin, acetamide, N-(4-methoxyphenyl)-2-[3-(2-methylpropoxyl) phenoxy, CAS registry 304692-07-7 was purchased from Ryan Scientific, Inc. The inactive compound, CAS registry 3922235-70-0 was purchased from Scientific Exchange, Inc.

Plasmids.

Harvard Institute of Proteomics FLEXGene Saccharomyces cerevisiae (yeast) ORF collection (pBY011 expression vector) (Hu, et al. (2007) Genome Res 17, 536-543) and PIG-W entry clone HsCD00295253 were obtained from the Dana Farber/HCC DNA Resource Core. All other gateway vectors used are available from Addgene (Alberti, et al. (2007) Yeast 24, 913-919). The reporter for the unfolded protein response, pRS304-4XUPRE-GFP, was a gift from Peter Walter (UCSD).

Fungal Strains.

Archives of all strains were maintained in 25% glycerol at −80° C. Standard S. cerevisiae lab strains W303, BY4741, BY4742 and BY4743 were used for experiments. The C. albicans wild type strain in FIG. 1 was CaI4, a standard laboratory strain (Fonzi, et al. (1993) Genetics 134, 717-728). The C. albicans fluconazole-resistant strains CaCi-2, CaCi-8 and CaCi17 were generously provided by Ted White and originally collected by Spencer Redding and colleagues (White, (1997) Antimicrob Agents Chemother 41, 1488-1494; White, (1997) Antimicrob Agents Chemother 41, 1482-1487; White, et al. (1997) Oral Dis 3 Suppl 1, S102-109). The sequenced C. albicans wild type strain, Sc5314 (Gillum, et al. (1984) Mol Gen Genet 198, 179-182) used in P-glucan experiments was a gift from John Perfect's lab. CaAmphR, an amphotericin B-resistant strain is from ATCC (#20095). Caspofungin-resistant strain Cfr1 was derived by plating Sc5314 on caspofungin plates and isolating resistant colonies. A. terreus was purchased from ATCC (MYA-3633). The C. glabrata strain CgL5c was obtained from John Bennett's lab. The YKO heterozygous diploid strain collection is from Open Biosystems and was generated in BY4743. Haploid deletion strains were from the Yeast Knock-out Deletion Collection and purchased from Invitrogen. The over-expression library was made by transforming BY4741 with the Harvard Institute of Proteomics Flexgene library.

Mammalian Cell Lines.

293T, NIH 3T3, and the RAW264.7 murine macrophage line were purchased from ATCC. Primary MEF were generated from day 13.5 mouse embryos using standard techniques.

Antifungal Susceptibility Testing.

Sensitivity to gepinacin was determined in 96-well, flat bottom microtiter plates using a modification of the NCCLS broth microdilution protocol CLS M27-A3 and RPMI as culture medium. Fungi were inoculated at ~$10^3$ cells per ml and incubated for 48 hours at 37° C. after which plates were sealed, shaken and the optical density read at 600 nm ($OD_{600}$) on a Tecan Safire 2 plate reader. All samples were run in duplicate or triplicate and assays were repeated at least once. Results are expressed as fraction of growth in the absence of compound and the mean and standard deviation are plotted. For the mold A. terreus, inoculum was $10^4$ cells per ml and plates were incubated at 35° C. for 48 hours in the dark. Plates were then visually scored as specified by CLSI document M38-A2 to determine the MIC50 and MIC80.

Mammalian Cell Toxicity Testing.

For co-culture experiments, confluent layers of NIH 3T3 cells were established in 6-well plates. The following day, the medium was replaced with RPMI1640+10% FBS containing the amphotericin-resistant strain CaAmphR at $10^3$ colony forming units per ml and 40 µM gepinacin or an equivalent amount of DMSO. Co-cultures were incubated for 24 hours at 37° C. in a micro-isolator box. Images were acquired on a Nikon Eclipse TS100 microscope at 40×.

Genetic Screening.

Flexgene plasmids were transformed in parallel into S. cerevisiae strain BY4741. The resulting library was arrayed in 384-well plates, grown to saturation in selective media, diluted and replicated using a Tecan EVO robot. Gepinacin (20 µM) or an equivalent amount of DMSO in SGal-URA-$NH_4$ media was added to duplicate plates before incubation in a humidified chamber at 23° C. in the dark. Plates were sealed, shaken, and read at 24 hours and then 4 more times over the next 2 days. The heterozygous deletion collection was pooled and grown at 30° C. in SGal-CSM with shaking to an $OD_{600}$ of approximately 1-2 and then diluted to an $OD_{600}$ of 0.05 in fresh media containing DMSO or 1.25 µM gepinacin. This was repeated 4 times with dilutions every ~12 hours. Genomic DNA preparation, PCR and chip hybridization were done as previously described (Giaever, et al. (2002) Nature 418, 387-391; Hoon, et al. (2008) Nat Chem Biol 4, 498-506; Pierce, et al. (2006) Proc Natl Acad Sci USA 105, 20918-20923). All hits were re-tested by growth assay in 384-well plate format and the relevant deletion confirmed by PCR with deletion specific primers.

In Vitro Acylation Assays.

Experiments were performed using a previously published protocol (Umemara, et al. (2003) J Biol Chem 278, 23639-23647) with the following modifications; UDP[$^3$H]GlcNAc was used instead of [$^{14}$C] and TLC plates were imaged by autoradiography. Lipid extracts were treated overnight with phosphatidylinositol-specific phospholipase C to confirm that the band identified as GlcN-(acyl)PI was resistant to cleavage (data not shown).

Filamentation.

For liquid assays, C. albicans strains were grown overnight in YPD with DMSO or 5 µM gepinacin. After dilution to an $OD_{600}$ of 0.1 in Spider media, growth was continued for an additional 3 hours with agitation at 37° C. in the presence of compound before transfer to a 24 well plate for imaging (Shen, et al. (2008) Proc Natl Acad Sci USA 105, 20918-20923). Assays with S. cerevisiae strain Sigma 1278B on solid media were performed as previously described (Liu, et al. (1994) Science 266, 1723-1726) except gepinacin was added directly to partially cooled plate media and colonies were imaged after growth for 6 or 9 days at 30° C.

Protein Trafficking Analysis.

HA-tagged GAS1 was expressed in strain BY4741 CPY-GFP (Yeast GFP collection (Huh, et al. (2003) Nature 425, 686-691) under control of its own promoter using plasmid pCM-HA-GAS1. This construct was created as previously reported except in a gateway plasmid backbone (Fujita, et al. (2006) Mol Biol Cell 17, 834-850). To assess effects on trafficking, strains were incubated for 1 hour at 30° C. with test compounds. Total cellular protein (5 µg) was separated by electrophoresis (Invitrogen 8% gels) and transferred to nitrocellulose membranes. Blots were hybridized with antibodies against HA (Covance), GFP (Roche), or CPY (Invitrogen). Sizes for the various post-translationally modified products of Gas1HA2 and CPY have been previously reported (Fujita, et al. (2006) Mol Biol Cell 17, 834-850). CPY-GFP was used to facilitate discrimination of CPY processing steps because GFP is cleaved from CPY in the yeast vacuole. The experiment, however, was also performed with untagged CPY with the same results.

Unfolded Protein Response.

The plasmid pRS304-4XUPRE-GFP was linearized and integrated into the TRP1 locus of S. cerevisiae (W303) to construct a reporter strain as previously described (Cox, et al. (1993) Cell 73, 1197-1206; Pollard, et al. (1998) Mol Cell 1, 171-182). Reporter cells were grown to log phase and exposed to compound at 23° C. for 5 hours before analysis. GFP reporter induction was monitored on a Guava EasyCyte Plus cytometer. The average mean channel fluorescence of duplicate samples was determined, and the experiment was performed twice with similar results.

β-Glucan Staining.

Overnight treatment and staining of C. albicans strain Sc5314 was performed as previously described for caspofungin treatment using YPD media at 30° C. to maintain growth in the yeast form (Wheeler, et al. (2006) PLoS Pathog 2, e35). Antibody to (1-3) β-D-glucan was obtained from Biosupplies (Australia). Cells were propidium iodide (PI) stained to assess viability and only PI-negative cells were analyzed. Microscopy was performed on a Nikon Eclipse microscope with a 100× oil objective.

Macrophage Stimulation and TNFα Measurement.

Cultures of C. albicans Sc5314 cells were drug treated as described for β-glucan staining. After overnight incubation, cultures were washed extensively, counted, and added to cultures of the mouse macrophage cell line RAW264.7 at a macrophage:yeast ratio of 1:2.5 in the continued presence of drug. After 2 hours supernatants were harvested and TNFα concentration measured by ELISA using a kit according to manufacturer's instructions (DY410, R&D Systems).

Suppressor Strains to Identify Mechanisms of Resistance.

Approximately $2 \times 10^7$ W303 MATa cells were spread on a YPD plate containing 20 µM gepinacin. Three colonies were recovered 5 days later. Of these, only two grew sufficiently for further experimentation. They were designated strains 20-1 and 20-2, and they were mated and sporulated. The gepinacin-resistant phenotype segregated 2:2 in the progeny indicating that the mutation conferring resistance was a single trait or more than one, but closely linked trait. The sensitivity of strains to cycloheximide was the same as wild type suggesting that the resistant phenotype was target-related, not efflux pump-mediated.

Genomic Sequencing

Using an Illumina HiSeq platform, we performed whole genome shotgun (WGS) sequencing of wild-type and gepinacin-resistant strains, obtaining two lanes of 76 base pair, paired-end reads and one lane of 101 base pair, paired-end reads for each genome. Raw reads are available via NCBI under BioProject accession number PRJNA16764 (derived strains), and SRA accession numbers SRX118359 and SRX118360 (wild-type). Depth of coverage averaged 100-fold.

Humanized Yeast Strain.

Because GWT1 deletion is lethal in S. cerevisiae strain BY4741, a haploid shuttle strain was constructed in which the genomic copy of GWT1 was deleted and replaced by GWT1 on a plasmid that also encoded the URA3 gene and a G418-resistance gene. To construct this shuttle strain a gwt1Δ/GWT1 heterozygous deletion mutant was transformed with pAGGPD416-GWT1, sporulated and dissected. A colony was selected that grew on both SD-URA and G418-containing plates. PCR with the deletion specific primers (http://wwwsequence.stanford.edu/group/yeast_deletion_project/deletions3.html) was performed to confirm the GWT1 deletion. To change the source of GWT, this shuttle strain was transformed with plasmids containing GWT1 (as a control) or PIG-W and the LEU2 auxotrophy gene followed by selection for growth on SD-LEU plates. Plasmids were constructed by conventional Gateway technology using a GWT1 encoding entry vector and either pAG415GPDccdB or pAG425GPDccdB as the destination vectors. Positive colonies were selected and grown on 5-fluoroorotic acid (5-FOA)-containing plates to promote loss of the pAGGPD416-GWT1 plasmid. The colonies from this plate were then tested for return of uridine auxotrophy to confirm pAGGPD416-GWT1 loss. The PIG-W expression vector was constructed by recombination in yeast as follows. The pAG415GPDccdB vector was cut with Xho1 and Xba1 and the larger piece was gel and column purified. The coding sequence of PIG-W was PCR amplified from the entry clone so that it would have ends facilitating recombination with the cut vector. The shuttle strain was then transformed with these two DNA fragments and plated on SD-LEU plates to select for recombinants. PIG-W plasmid was isolated from the final strain and sequence verified.

Protein Lysis Procedure.

Yeast were spun down, washed two times with $H_2O$ and lysed in ethanol containing phenylmethylsulfonyl fluoride. An equivalent volume of glass beads were added and after beating, samples were transferred to a −80° C. freezer for an hour. The samples were then evaporated to dryness in a Savant SpeedVac concentrator. Solubilization buffer (200 ul of 2% SDS in 20 mM Tris HCl pH 6.8) was added to the dry beads which were vortexed and then boiled 5 min. Protein concentrations were determined by BCA assay (Pierce) and equal amounts of total protein were diluted into 5× reducing loading buffer (0.5 M DTT, 20 mM Tris HCl, 50% Glycerol) for subsequent analysis by SDS-PAGE.

Data Analysis of Over-Expression Screen.

Raw data for each gepinacin-treated 384-well plate was quantile normalized to achieve the same distribution as one of the DMSO replicates at the corresponding reading time.

The R package limma (Smyth, (2004) *Stat Appl Genet Mol Biol* 3, Article 3) was then used to compute empirical Bayes moderated t-statistics for each gene. Genes were flagged as hits if the mean difference in normalized optical density scores between DMSO and gepinacin was at least 0.1 at any reading time, and if the p-value for this difference had an associated FDR (false discovery rate) of at most 0.2. Hits were re-tested and plasmids sequenced to confirm their identity.

Analysis of Sequencing Data.

After quality control was performed on raw reads for each genome, we aligned the filtered reads against the *S. cerevisiae* reference sequence sacCer2, (June 2008 assembly, downloaded from UCSC on Apr. 1, 2011: http://hgdownload.cse.ucsc.edu/goldenPath/sacCer2/chromosomes/) using the BWA aligner (Li, et al. (2009) *Bioinformatics* 25, 1754-1760). For each of the strains, we called SNPs and indels with respect to the reference using mpileup from the SAMtools package (Li, et al. (2009) *Bioinformatics* 25, 2078-2079). To identify SNPs and indels unique to each of the resistant strains, we compared the parental strain to individual resistant lines. We used a combination of custom code and the Genome Analysis Toolkit (GATK) (DePristo, et al. (2011) *Nat Genet* 43, 491-498) to locate, and then rank by quality, the SNPs and indels detected in open reading frames that were present only in the suppressor strains. Alignments of the reads for the top ranked SNPs and indels were then visually inspected.

Highly Selective Antifungal Activity Against a Diverse Range of Fungi

Gepinacin (FIG. 1a) inhibited the growth of diverse yeasts and molds separated by approximately 800 million years of evolution, including *S. cerevisiae, Candida glabrata, Candida albicans* and *Aspergillus terreus* (Heckman, et al. (2001) *Science* 293, 1129-1123). This suggested the involvement of a mechanism widely conserved among fungi (FIG. 1b). Importantly, it inhibited the growth of multiple isolates of the common fungal pathogen *C. albicans*. These strains were chosen to represent resistance to each of the three major classes of antifungals that are currently in clinical use (FIG. 1c). The lack of cross-resistance and the absence of structural similarity to established antifungal drugs suggested the compound might exert its activity through a novel mode of action. Lack of cytotoxicity for mammalian cells suggested sufficient divergence of target and/or mechanism between humans and fungi to provide a useful therapeutic index for eventual development of the chemotype as an antimicrobial (FIG. 1d).

Target Identification Using Yeast Genetics

Figure 2:
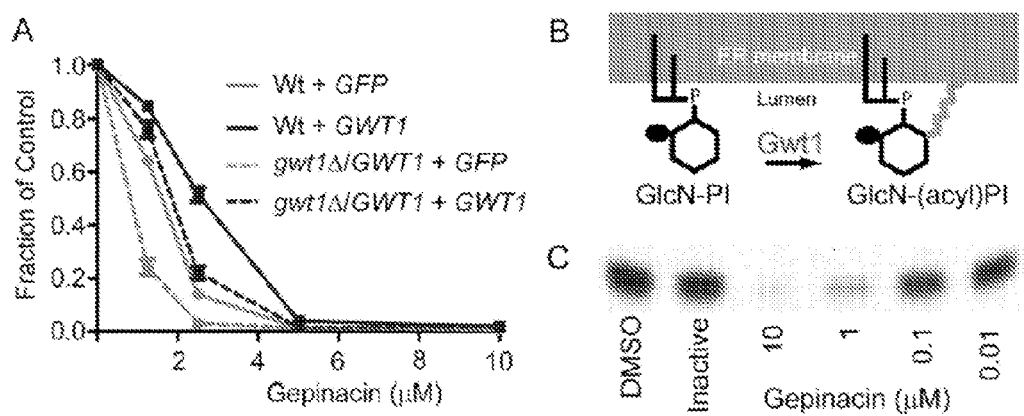
FIG. 2 shows that Gwt1 is the target of gepinacin. (A) Anti-fungal susceptibility testing of *S. cerevisiae* strains with graded levels of Gwt1 expression treated with gepinacin. Wild type diploids (Wt) or diploids with one copy of GWT1 deleted (gwt1/GWT1) were transformed with low copy (CEN) plasmids encoding GWT1 or GFP (as a control). (B) Schematic of Gwt1 protein function in cells. Glucosamine (shown as a black circle) phosphatidyl inositol (GlcN-PI) is acylated (orange zigzag) by Gwt1 to become GlcN-(acyl)PI. (C) Autoradiograph depicting the relative amount of GlcN-(acyl)PI product formed in acylation reactions supplemented with various concentrations of gepinacin or an inactive analog (10 μM). The structure of the inactive compound is shown in FIG. 1.
Figure 8:
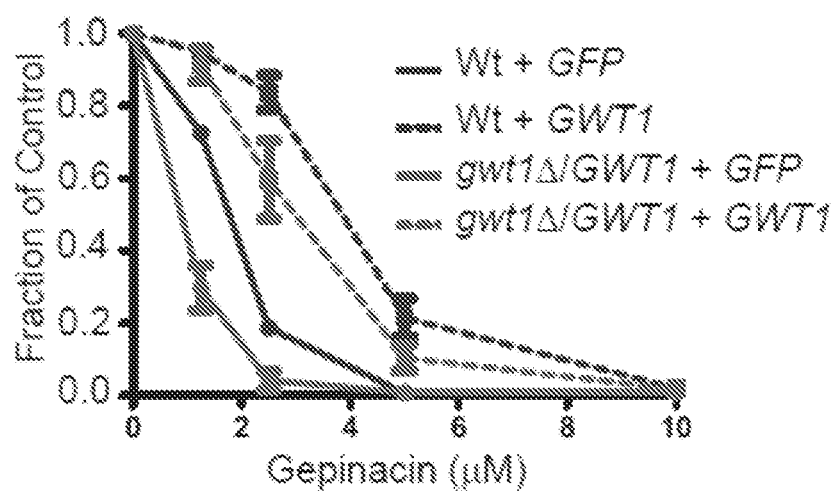
FIG. 8 shows that GWT1 copy number determines gepinacin sensitivity. Anti-fungal susceptibility testing of wild type diploids (Wt) or diploids with one copy of GWT1 deleted (gwt1Δ/GWT1) transformed with high copy (2 micron) plasmids containing GWT1 or GFP (as a control). The strains were treated with gepinacin for 48 hours and the growth was monitored by measuring the optical density at 600 nm ($OD_{600}$). The results are expressed as a fraction of the OD600 measured in the absence of gepinacin.

To determine the mechanism responsible for the antifungal activity of the compound, the powerful genetic tools available in the model fungal organism *S. cerevisiae* were utilized. Both an arrayed haploid over-expression library and a pooled heterozygous deletion library were screened for enhancement or suppression of toxicity. The over-expression library consisted of 5336 individual haploid strains arrayed in 384-well plate format. With each strain expressing one open reading frame (ORF), this library covered approximately 90% of the yeast genome. (Hu, et al. (2007) *Genome Res* 17, 536-543). The heterozygous deletion library consisted of a pool of 5797 diploid strains in which one copy of approximately 95% of the ORFs in the *S. cerevisiae* genome had been disrupted previously by targeted insertion of a bar-coded antibiotic resistance cassette (Giaever, et al. (2002) *Nature* 418, 387-391). Only one gene, GWT1 was recovered as a hit shared by both libraries. Gwt1 is essential for growth of *S. cerevisiae* under normal conditions and has previously been characterized as an acyltransferase that is critical for GPI-anchor biosynthesis (Umemara, et al. (2003) *J Biol Chem* 278, 23639-23647). When GWT1 was over-expressed, it rescued gepinacin toxicity and when it was deleted, toxicity was enhanced. Furthermore, GWT1 was not identified as a hit for 8 unrelated compounds that were tested in parallel for other projects. To confirm the effect of GWT1 yeast strains were engineered to express a wide range of GWT1 gene copies (FIG. 2a). Starting with a wild type diploid (Wt) strain that carries two genomic copies of GWT1, a low copy (CEN) plasmid was introduced expressing GWT1 or GFP (as a control). In parallel, the same plasmids were transduced into a heterozygous deletion strain (gwt1Δ/GWT1) which had only one genomic copy of GWT1. As expected, the toxicity of gepinacin inversely correlated with GWT1 copy number. High level expression of GWT1 driven by a two micron plasmid further decreased gepinacin activity in both genotypes (FIG. 8). These genetic data establish Gwt1, or at least the pathway in which it acts, as the most functionally relevant target for the antifungal activity of gepinacin.

Biochemical Validation of Gwt1 as the Target

Figure 9:
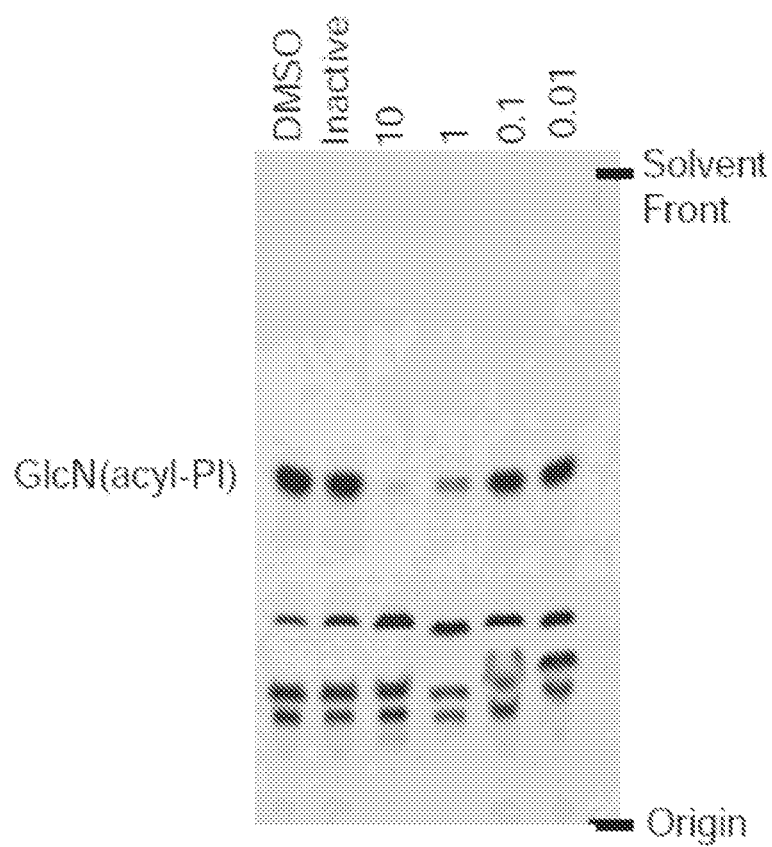
FIG. 9 shows that GWT1 is the target of gepinacin. Full autoradiograph depicting the relative amounts of radioactive product formed in acylation reactions supplemented with gepinacin. The GlcN(acyl-PI)-labeled product of interest is shown in FIG. 2C.
Figure 10:
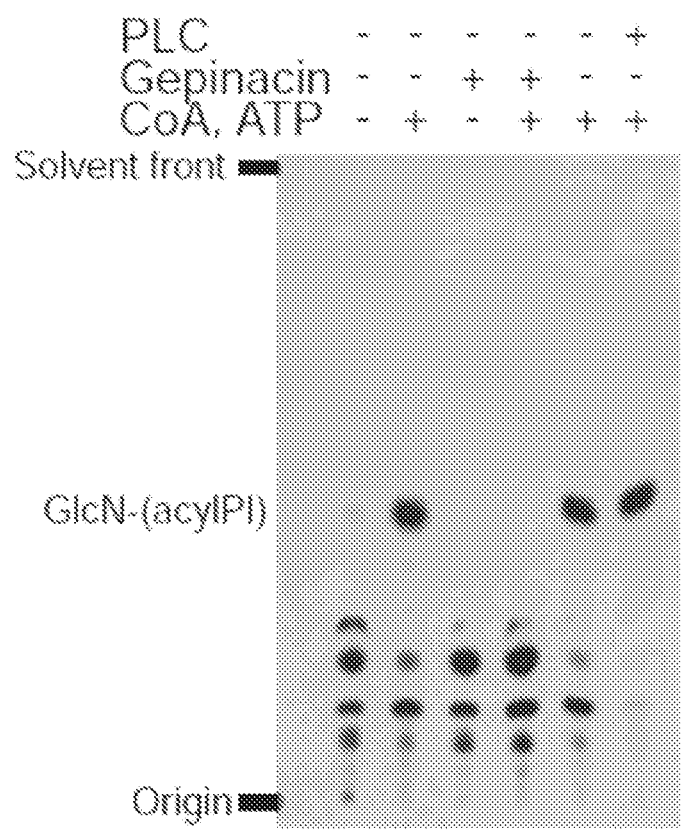
FIG. 10 shows that the phospholipase-C insensitive product GlcN-(acylPI is not produced in the presence of gepinacin. Autoradiograph depicting the relative amounts of radioactive product formed in acylation reactions. The second to the last lane on the right is a solvent control reaction. It was processed in the same manner as the last lane on the right except that phospholipase-C was omitted.
Figure 11:
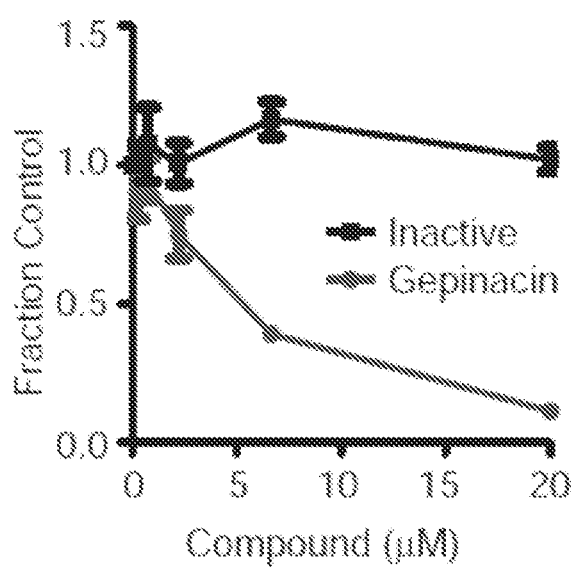
FIG. 11 shows that a close structural analog of gepinacin does not inhibit growth. Anti-fungal susceptibility testing of a fluconazole-resistant *C. albicans* strain under standard conditions. Yeast were incubated at 30° C. for 24 hours with serial dilutions of the indicated compounds. Growth was monitored by $OD_{600}$ and is expressed as fraction of the growth observed in the absence of compound.

Production of GPI-anchors begins on the cytoplasmic surface of the ER but is completed on the luminal side. Gwt1 (in yeast) or PIG-W (mammalian) acts at the first step on the luminal side of the ER, the acylation of glucosamine phosphatidylinositol (GlcN-PI) (FIG. 2b) (Sagane, et al. (2011) *J Biol Chem* 286, 14649-14658; Murakami, et al. (2003) *Mol Biol Cell* 14, 4285-4295). To provide direct biochemical evidence that Gwt1 is the proximal protein target of gepinacin in vitro acylation reactions were performed using yeast membrane preparations. UDP[$^3$H]GlcNAc was incubated with the membranes, and the resulting lipid products were recovered by chemical extraction and fractionated by silica gel thin layer chromatography (TLC). The appearance of a phospholipase-C insensitive band indicated the production of the acylated product. Gepinacin inhibited the acylation of GlcN-PI at low micromolar concentration (FIG. 2c; full autoradiograph provided in FIG. 9, phospholipase-C control provided in FIG. 10) while a compound that was structurally very similar but biologically inactive did not (FIG. 1a, FIG. 11).

Figure 3:
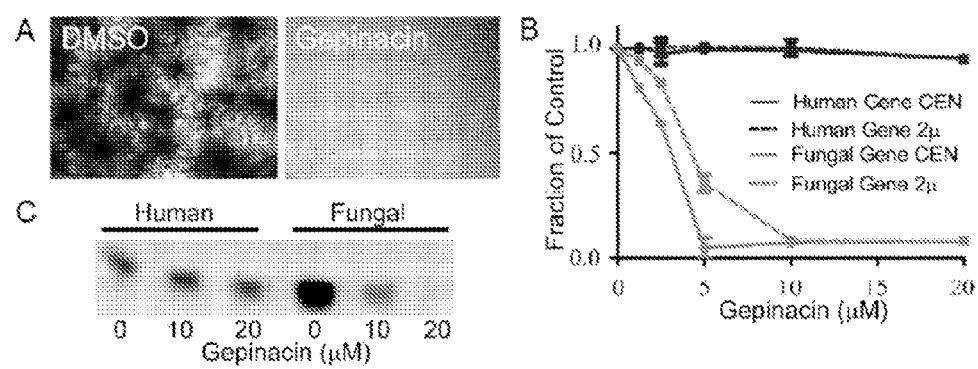
FIG. 3 shows that gepinacin inhibits Gwt1 but not its human ortholog, PIG-W. (A) Representative photomicrograph of mammalian cells (NIH3T3) co-cultured with amphotericin-resistant *C. albicans* following addition of DMSO or 40 μM gepinacin. Photographs were taken after 24 hours. DMSO-treated cultures have large, dense colonies of *C. albicans* which are not present in gepinacin-treated cultures. (B) Anti-fungal susceptibility testing of *S. cerevisiae* strains in which the endogenous GWT1 gene had been replaced by plasmid-driven expression of the human gene (PIG-W), or the fungal gene (GWT1). CEN plasmids are low copy, 2 t plasmids are high copy. (C) Autoradiograph depicting the relative amount of GlcN-(acyl)PI product formed in acylation reactions supplemented with gepinacin and using membranes prepared from the low copy plasmid strains presented in panel B. These results confirm that activity of the human enzyme is not inhibited by gepinacin.

Having determined the target of gepinacin in fungi, gepinacin's effect on the human ortholog of Gwt1, PIG-W, was examined. To determine if gepinacin remained active under mammalian cell culture conditions cultured fungi were cultured (either an amphotericin B-resistant (FIG. 3a) or fluconazole-resistant (data not shown) isolate of *C. albicans*) and mammalian cells together with 40 µM gepinacin. These co-culture experiments demonstrated profound inhibition of proliferation for both fungal strains under serum-containing cell culture conditions, with no effect on mammalian cells in the same well. PIG-W (and GPI anchor biosynthesis) is not essential for mammalian cells in culture. Therefore, these experiments do not rule out the possibility that gepinacin inhibits PIG-W, but they do show that gepinacin remains active in this complex co-culture environment.

Figure 12:
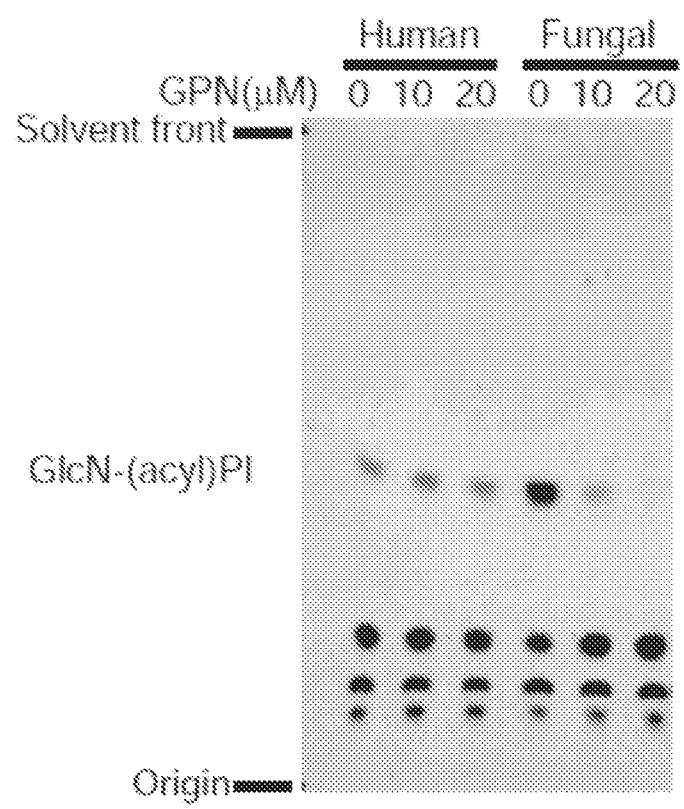
FIG. 12 shows that gepinacin inhibits Gwt1 but not its human ortholog, PIG-W. Full autoradiograph depicting the relative amounts of radioactive product formed in acylation reactions supplemented with gepinacin and membranes prepared from the engineered yeast strains shown in FIG. 3B. The GlcN(acyl-PI)-labeled product of interest is shown in FIG. 3C.

The genetic tractability of *S. cerevisiae* was employed to determine whether gepinacin is selective for the fungal protein. Gwt1 is essential in this organism, and the human protein is capable of fulfilling its essential function (Watanabe, et al. (2012) *Antimicrob Agents Chemother* 56, 960-971). We constructed a pair of transgenic strains in which a deletion of the GWT1 gene was rescued by heterologous expression of either the human or yeast genes (PIG-W or GWT1, respectively). While gepinacin was inactive in the PIG-W expressing strain, it potently inhibited both cell growth and acyltransferase activity in the strain expressing the yeast gene (FIG. 3b, 3c, full autoradiograph provided in FIG. 12). These results establish the proximal determinant of gepinacin toxicity as the fungal Gwt1 protein and demonstrate highly species-selective activity for the compound.

Deletion of Trafficking Adaptor Protein EMP24 Partially Suppresses Toxicity

Figure 4:
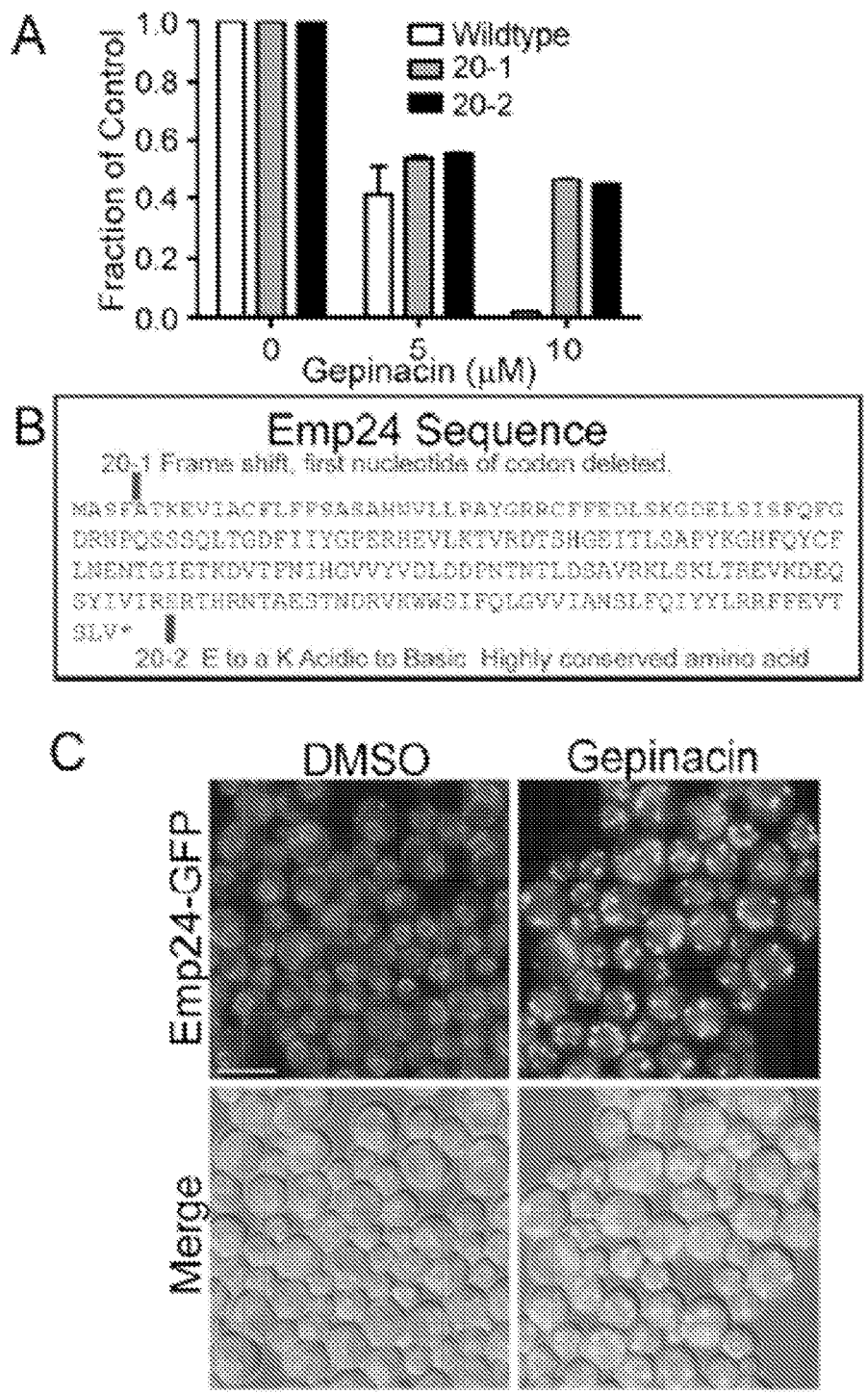
FIG. 4 shows that EMP24 deletion decreases gepinacin toxicity. (A) Anti-fungal susceptibility testing of gepinacin using suppressor strains 20-1 and 20-2. (B) The sequence of EMP24 in *S. cerevisiae* is shown with the location of mutations found by whole genome sequencing in the suppressor strains 20-1 and 20-2 indicated. The sequence in FIG. 4B corresponds to SEQ ID NO: 1. (C) Micrographs showing the redistribution of Emp24-GFP after overnight incubation with 5 μM gepinacin. Green fluorescence and DIC images are merged in the lower panels. Scale bar; 5 μm.
Figure 13:
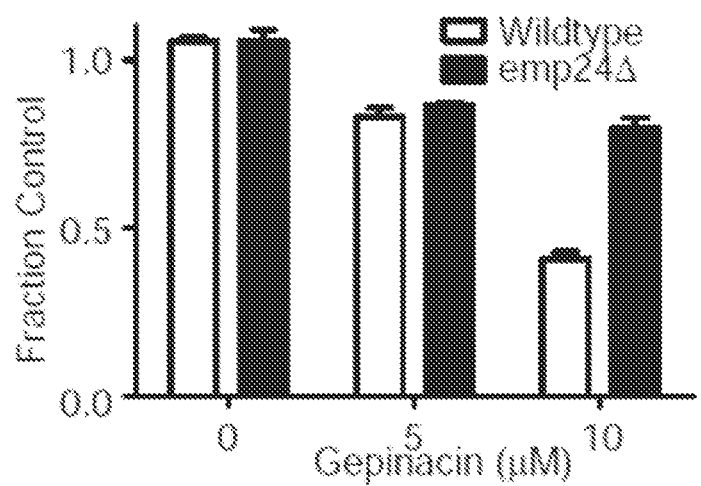
FIG. 13 shows that EMP24 deletion partially suppresses inhibition of growth by gepinacin. Anti-fungal susceptibility testing of *S. cerevisiae* strains that are wild type or deleted for EMP24. Growth was assessed by measuring the $OD_{600}$ following gepinacin treatment for 48 hours at 30° C. in 96-well plate format. Mean and standard deviation of triplicate determinations are shown.

To identify mechanisms that might confer resistance, two spontaneously arising gepinacin-resistant clones carrying mutations that partially suppressed gepinacin toxicity in S. cerevisiae were isolated (FIG. 4a). Whole genome sequencing of these strains showed that resistance was due to two different mutations in the gene EMP24 (FIG. 4b). This finding was recapitulated with targeted deletion of EMP24 (FIG. 13). The non-essential protein Emp24 is a component of a large multi-protein complex that regulates GPI-anchored protein transport and quality control (Strating, et al. (2009) Biol Cell 101, 495-509). GPI-anchored proteins do not contain transmembrane domains. As an integral membrane protein, Emp24 specifically interacts with the anchor portion of GPI-anchored proteins monitoring the completion of their processing and assisting their incorporation into ER to Golgi transport vesicles (Castillon, et al. (2011) Mol Biol Cell 22, 2924-2936). When GPI-anchored proteins are incompletely remodeled, Emp24 is thought to facilitate their return to the ER. The deletion or inactivation of EMP24 has been shown to allow GPI-anchored proteins to bypass this quality control step and to exit the ER (Castillon, et al. (2011) Mol Biol Cell 22, 2924-2936). Deletion of EMP24 could suppress gepinacin toxicity in an analogous manner by relieving a trafficking block induced by the compound.

To determine if gepinacin does indeed alter trafficking and change Emp24 distribution yeast in which GFP was fused in frame to the 3' end of genomic EMP24 were examined. Emp24-GFP normally shows a classical ER distribution pattern consisting of well-defined circles in the interior of the cell with a fainter cortical ring and a few bright dots consistent with some Golgi localization. After overnight culture in gepinacin, however, Emp24-GFP dramatically re-localized into large, bright dotlike structures (FIG. 4c). This pattern indicates that the compound had induced severe disorganization of the ER, and/or a profound block in retrograde trafficking that would normally return Emp24 to the ER as part of its physiological cycling.

GPI-Specific Trafficking Defects Caused by Gepinacin Induce ER Stress

Figure 5:
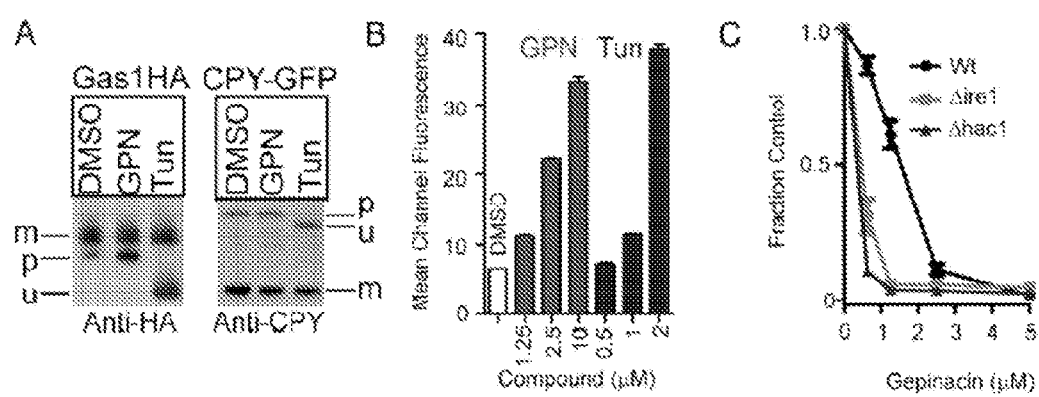
FIG. 5 shows that Gwt1 inhibition by gepinacin impairs GPI-anchored protein maturation and causes ER-related toxicity. (A) Immunoblots of lysates prepared from *S. cerevisiae* treated with gepinacin showing GPI-anchor-selective impairment of protein maturation. The unprocessed (u), precursor (p), and mature (m) forms of the reporter proteins are indicated. The identity of the tagged reporter proteins (top of panel) and the antibodies used for their detection (bottom of panel) are also indicated. Treatment conditions are DMSO (0.05%), gepinacin (GPN, 10 μM) or tunicamycin (Tun, 10 μM). The same lysate was used for both blots. (B) Induction of the unfolded protein response in cells carrying a GFP reporter construct showing strong induction by gepinacin. GFP expression was monitored by flow cytometry. (C) Anti-fungal susceptibility testing of strains deleted for IRE1 (activator of the UPR) or HAC1 (effector of the UPR) showing their increased sensitivity to gepinacin.

To further pursue the effects of gepinacin on protein trafficking in the secretory compartment, the effects of gepinacin on maturation of the sentinel proteins Gas1 and CPY were compared. Both proteins undergo characteristic molecular weight changes as they are processed in transit through specific cellular compartments, a feature that has been used extensively to study protein trafficking in the secretory system. Gas1 travels through the ER where it acquires a GPI-anchor before translocating to the Golgi and outward to the cell surface (Fankhauser, et al. (1991) Eur J Biochem 195, 439-448). CPY is not GPI-anchored but undergoes sorting and processing in the secretory pathway before ending up in the yeast vacuole (Bryant, et al. (1998) Microbiol Mol Biol Rev 62, 230-247). In actively growing wild type yeast, the mature (m), Golgi-processed form of Gas constitutes the predominant species, relative to the precursor (p) form found in the ER (FIG. 5a). This distribution was inverted following exposure to gepinacin. In contrast, the processing of CPY which is not GPI-anchored was identical in control and gepinacin-treated cells. This confirms a highly restricted effect of Gwt1 inhibition on the trafficking of GPI-anchored proteins. The control compound, tunicamycin, a natural product that blocks production of all N-linked glycoproteins, alters the processing of both proteins as expected (Heifetz, et al. (1979) Biochemistry 18, 2186-2192).

Figure 14:
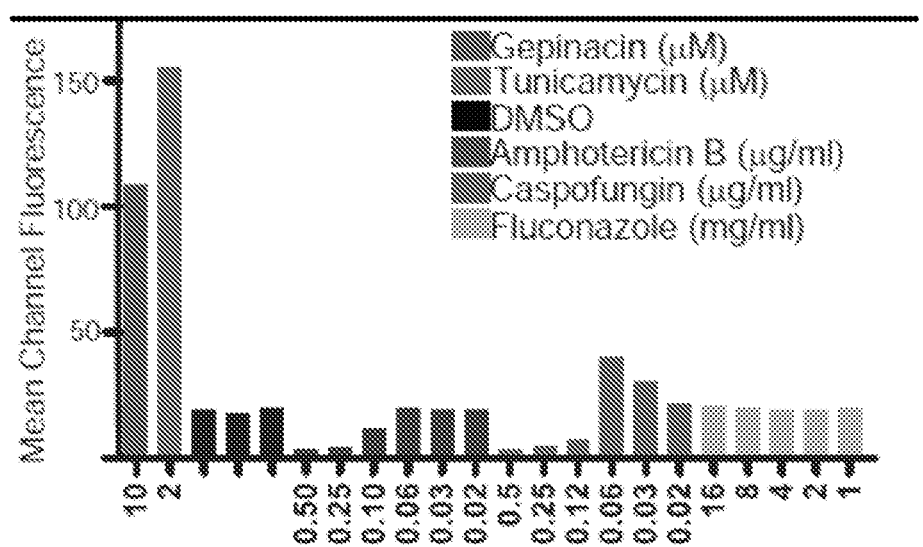
FIG. 14 shows that conventional anti-fungal drugs do not induce the UPR. Induction of the unfolded protein response in cells carrying a GFP reporter construct was monitored by flow cytometry after exposure to serial dilutions of the indicated compounds for 5 hrs. Strong induction by gepinacin and tunicamycin but not by conventional anti-fungal drugs is evident.
Figure 15:
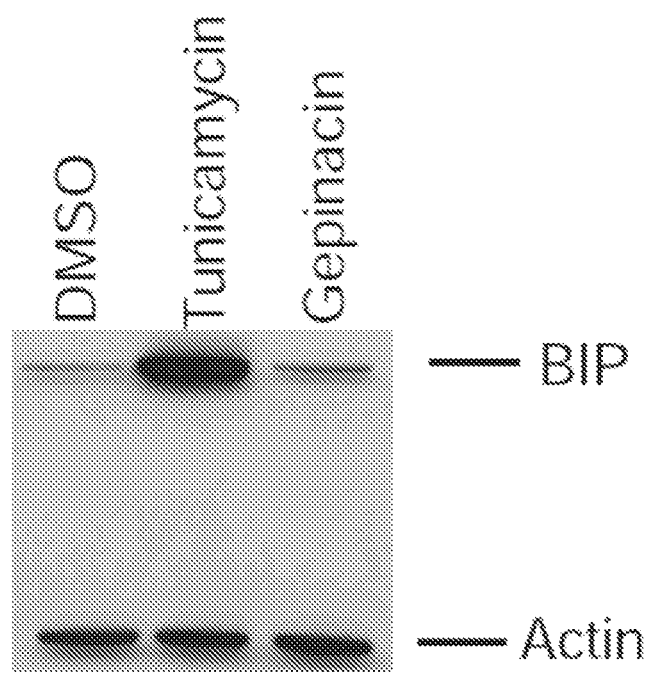
FIG. 15 shows that BIP level, an indicator of the UPR in mammalian cells, is not increased after gepinacin treatment. Immunoblot of lysates prepared from human leukemia cells (K562) using an antibody to BIP after 28 hour exposure to tunicamycin (1 μg ml$^{-1}$), gepinacin (20 μM) or solvent vehicle (DMSO, 0.1%). Betaactin was blotted as a loading control.
Figure 16:
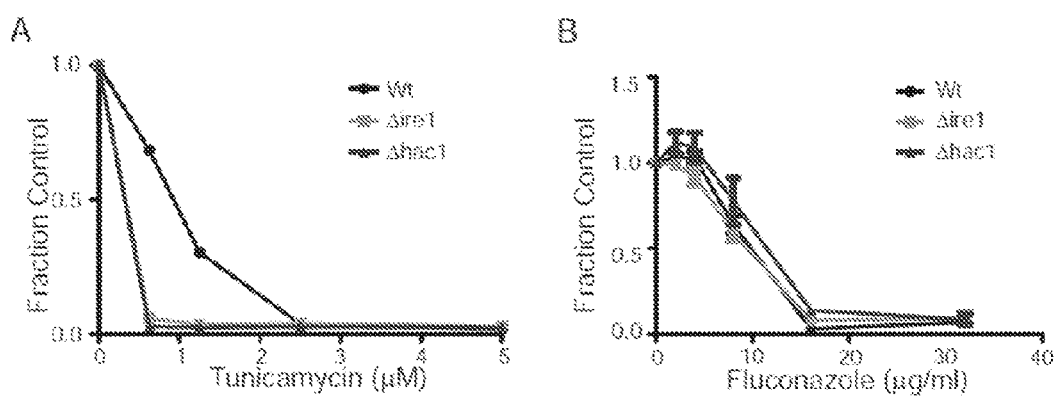
FIG. 16 shows that compromising the UPR enhances tunicamycin toxicity but does not alter the toxicity of fluconazole. Anti-fungal susceptibility testing of strains bearing deletion of IRE1 (activator of the UPR) or HAC1 (effector of the UPR) using either tunicamycin (A) or fluconazole (B). Growth was measured by $OD_{600}$ after 48 hour exposure to serial dilutions of the compounds as indicated. Results are expressed as a fraction of the $OD_{600}$ measured in the absence of gepinacin. The mean and standard deviation of triplicate determinations are shown.

The specific effects of gepinacin on GPI-anchored proteins provided a highly selective tool to investigate the impact of inhibition of inositol acylation on protein homeostasis within the ER. Culture for 5 hours in gepinacin induced a massive, concentration-dependent activation of the unfolded protein response (UPR) as monitored by the GFP reporter construct (UPRE-GFP) which encodes GFP under the transcriptional control of the KAR2 unfolded protein response element. Reporter activation was similar in extent to the effect produced by tunicamycin (FIG. 5b). Activation of the UPR was not seen when yeast were treated with representative compounds from the three major classes of anti-fungals: amphotericin B, caspofungin and fluconazole (FIG. 14). As expected based on its target selectivity, gepinacin did not perturb ER function in mammalian cells as monitored by induction of BIP, an ER-resident chaperone and classical marker of the UPR in mammalian cells (FIG. 15) (Walter, et al. (2011) Science 334, 1081-1086; Ma, et al. (2001) Cell 107, 827-830). Deletions of HAC1 and IRE1 which are essential components of the UPR activation pathway in yeast, both greatly increased the toxicity of gepinacin (FIG. 5c). As a positive control, similar enhancement of tunicamycin toxicity was seen in association with deletion of these genes (FIG. 16a). In contrast, toxicity of the conventional antifungal fluconazole which targets ergosterol biosynthesis was completely unaffected by these UPR-disabling deletions (FIG. 16b) (Ostrosky-Zeichner, et al. (2010) Nat Rev Drug Discov 9, 719-727).

Gwt1 Inhibition Blocks Filamentation

GPI-anchoring of proteins is conserved in all eukaryotes. However, major differences in the utilization of this post-translational modification between species provide an attractive point of attack in developing new antimycotics. In fungi, unlike mammalian cells, GPI-anchored proteins become covalently linked to β-1,6 glucan following translocation to the cell surface which helps maintain integrity of the cell wall. In addition, their presence at the cell surface permits GPI-anchored proteins in fungi to play important roles in adhesion, filamentation and sensing of the environment. Also important to pathogenesis, they provide a heavily glycosylated and phosphorylated outer coat to shield fungi from recognition and attack by the immune system of the mammalian hosts they invade (Orlean, et al. (2007) J Lipid Res 48, 993-1011; Klis, et al. (2009) FEMS Yeast Res 9, 1013-1028).

Figure 6:
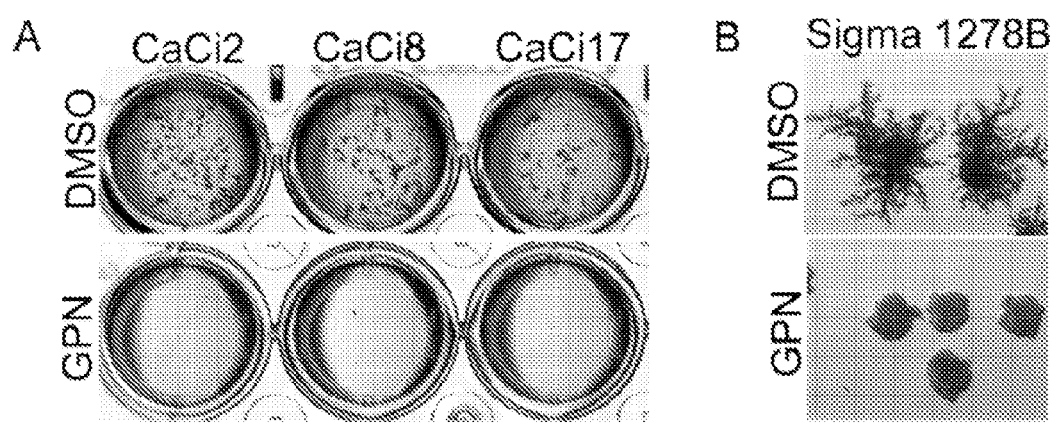
FIG. 6 shows that gepinacin blocks filamentation in liquid and solid culture models. (A) Fluconazole resistant *C. albicans* strains were treated overnight with DMSO (0.025%) or gepinacin (GPN) (5 μM) in filamentation media and then imaged macroscopically. (B) *S. cerevisiae* strain Sigma 1278B was grown on filamentation-inducing plates containing DMSO (0.025%) or gepinacin (GPN) (5 μM) for 6 days and then imaged microscopically.
Figure 17:
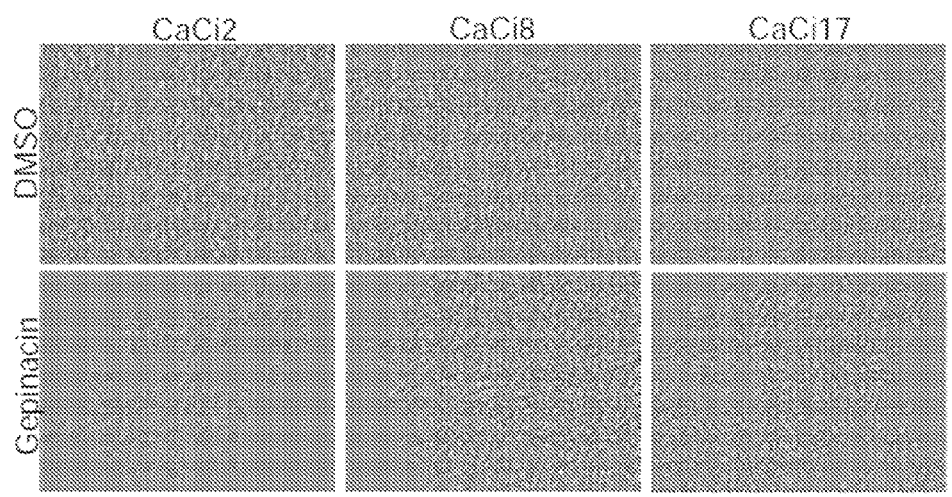
FIG. 17 shows that gepinacin blocks morphogenic switching in *C. albicans*. Three drug-resistant strains of *C. albicans* were treated with DMSO or gepinacin (5 μM) and induced to filament for 3 hours. DIC images were acquired at 60×.

Because of its role in tissue invasion, a key determinant of fungal virulence is the ability to switch between yeast and filamentous forms (Shapiro, et al. (2011) Microbiol Mol Biol Rev 75, 213-267; Sudbery, (2011) Nat Rev Microbiol 9, 737-748; Noble, et al. (2010) Nat Genet 42, 590-598). A previous report has shown that mature GPI-anchors are required for this process (Richard, et al. (2002) Microbiology 148, 2125-2133). To determine whether gepinacin impairs this important process in C. albicans, a series of three increasingly fluconazole-resistant clinical isolates that had been isolated over a two year period from an HIV patient treated with fluconazole, strains CaCi2, 8 and 17, were used (White, et al. (1997) Oral Dis 3 Suppl 1, S102-109). These strains were grown overnight with gepinacin or vehicle control in rich medium at 30° C. to maintain the cells in the yeast form. To induce morphogenic transformation they were then transferred to filamentation medium (Spider medium) at 37° C. for 3 hours in the continued presence or absence of gepinacin (Liu, et al. (1994) *Science* 266, 1723-1726). In the absence of gepinacin, all three drug-resistant clinical isolates underwent marked transformation to large macroscopic mats, readily visible to the eye. Because this process is so dependent on GPI-anchored proteins, however, a concentration of gepinacin that minimally reduced proliferation completely blocked the ability of all three strains to undergo such filamentation (FIG. 6a). The inability to form filaments was also apparent at the cellular level as demonstrated by the photomicrographs provided in FIG. 17. Comparable results were obtained when using serum-containing medium to induce filamentation instead of "Spider medium." Gepinacin also blocked filamentation on solid media using the well-characterized *S. cerevisiae* strain Sigma 1278B, which spontaneously grows as filamentous mats on agar substrates (FIG. 6b). The ability of gepinacin to inhibit conversion of fungi to their invasive filamentous forms is broadly relevant to diverse species and growth conditions with important implications for their pathogenicity in animal hosts.

Gwt1 Inhibition Enhances Immunogenicity

Figure 7:
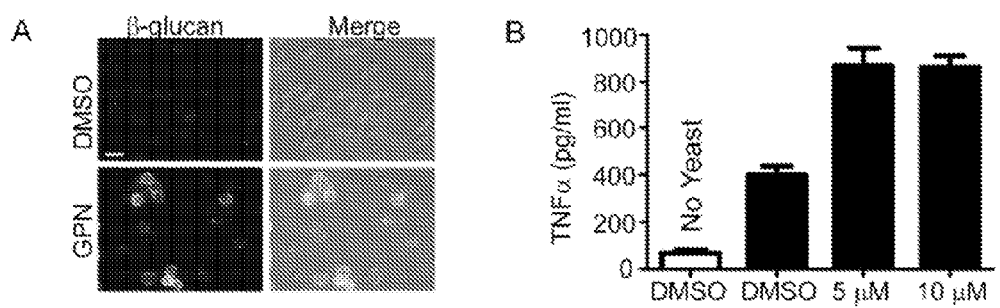
FIG. 7 shows that gepinacin treatment increases β-glucan exposure on the cell surface and enhances TNFα secretion from macrophages. (A) Fluorescence photomicrographs depicting the β-glucan (green) immunoreactivity of *C. albicans* after treatment with DMSO or 5 μM gepinacin (GPN). Cells were also imaged with DIC and counter-stained with a viability marker. Representative fields of live cells are shown here. Scale bar; 5 μm. (B) Measurement of TNFα concentration in macrophage supernatant by ELISA. Supernatants were harvested after co-culture of RAW264.7 murine macrophages and *C. albicans* treated with DMSO or gepinacin at the concentrations indicated.

The fungal selectivity of gepinacin was exploited to investigate another key determinant of fungal virulence, namely the ability to escape immune recognition. The large amount of β-glucan in the cell wall of fungi constitutes a potent pro-inflammatory stimulus, but it is normally masked by a mannoprotein coat (Poulain, et al. (2004) *Curr Opin Microbiol* 7, 342-349). In previous studies, mutation of GWT1 was shown to change the cell wall composition such that the outer mannoprotein layer became thinner and the inner glucan layer became thicker (Tsukahara, et al. (2003) *Mol Microbiol* 48, 1029-1042). It was predicted that disrupting GPI-anchor synthesis through inhibition of Gwt1 would unmask β-glucan leading to enhanced recognition of *Candida* by mammalian immune cells. Indeed, as revealed by immunostaining and fluorescence microscopy, sub-lethal concentrations of gepinacin did dramatically increase β-glucan presentation on the cell surface of *C. albicans* (FIG. 7a). Quantitation of this effect by flow cytometry confirmed a 4.5-fold increase in median channel fluorescence for gepinacin-treated *candida* compared to control-treated yeast. Such β-glucan exposure has been demonstrated previously for caspofungin, an echinochandin that perturbs cell wall synthesis. In contrast to gepinacin, however, the effect of caspofungin is limited to only filamentous forms of *C. albicans* (Wheeler, et al. (2008) *PLoS Pathog* 4, e1000227). As an important functional consequence of increased β-glucan exposure, incubation of gepinacin-treated *C. albicans* with a mouse macrophage cell line (RAW264.7) more than doubled the secretion of the major pro-inflammatory cytokine TNFα by these professional antigen-presenting cells (FIG. 7b).

Gwt1 as a Target for Antifungal Drugs

Figure 18:
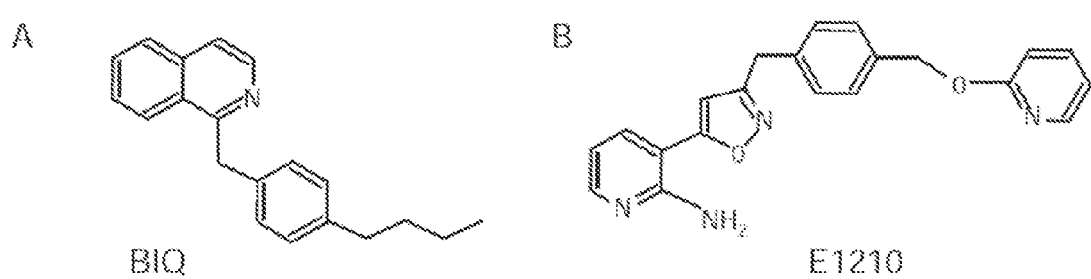
FIG. 18 depicts previously reported Gwt1 inhibitors that are structurally distinct from gepinacin. (A) BIQ (Tsukahara, et al. (2003) *Mol Microbiol* 48, 1029-1042) and (B) E1210 (Hata, et al. (2011) *Antimicrob Agents Chemother* 55, 4543-4551).

The biosynthesis of GPI anchors in fungi was first proposed as a potential antifungal drug target by Tsukahara et al. ((2003) *Mol Microbiol* 48, 1029-1042). In an extensive screening effort, they identified 1-[4-butylbenzyl]isoquinoline (BIQ) as an inhibitor of the surface expression of GPI-anchored proteins (structure in FIG. 18a). GWT1 was subsequently cloned as a dosage-dependent suppressor of BIQ-induced phenotypes. Further discovery and optimization efforts by this group led to better anti-fungal candidates (Nakamoto, et al. (2010) *Bioorg Med Chem Lett* 20, 4624-4626) and the synthesis of E1210, a potent and selective Gwt1 inhibitor with properties suitable for clinical development (structure in FIG. 18b). E1210 shows good activity in vitro and in mouse models against a broad spectrum of yeast and molds including medically relevant species of *candida, aspergillus* and *fusarium* (Miyazaki, et al. (2011) *Antimicrob Agents Chemother* 55, 4652-4658; Hata, et al. (2011) *Antimicrob Agents Chemother* 55, 4543-4551). E1210 has also been shown to decrease fungal adherence to polystyrene and inhibit biofilm formation. Like gepinacin, it is non-toxic to mammalian cells at concentrations that far exceed those required for antifungal activity (Watanabe, et al. (2012) *Antimicrob Agents Chemother* 56, 960-971). The unusually high degree of selectivity for both gepinacin and E1210 arises from species-specific discrimination at the biochemical level of target inhibition and from the different roles that GPI-anchored proteins play at the biological level in fungi versus mammals.

Although the structurally distinct compounds gepinacin and E1210 were discovered through completely different screening strategies, they share key biological properties rooted in Gwt1, the molecular target they hold in common. Both compounds inhibit fungal proliferation, compromise the cell wall and impair the morphogenic filamentation program which is required for pathogenicity in animal hosts (Watanabe, et al. (2012) *Antimicrob Agents Chemother* 56, 960-971). Our discovery of a new chemotype that selectively inhibits the fungal protein Gwt1 highlights the suitability of this protein as a highly druggable, therapeutic target. This is noteworthy from the drug development perspective because Gwt1 and its close mammalian ortholog are multi-pass transmembrane proteins for which atomic-level structural information is not available to help guide medicinal chemistry efforts. In pursuing the work presented here, the present inventors have constructed gene-swapped yeast strains in which the sole source of essential acyltransferase activity for GPI anchor synthesis is provided by either Gwt1 or its human ortholog PIG-W. These strains can now be used for SAR studies to optimize the potency and selectivity of the known chemotypes and also to efficiently screen for yet other compounds that preferentially inhibit the fungal enzyme or alternatively that inhibit the human enzyme to study its role in mammalian biology (Murakami, et al. (2003) *Mol Biol Cell* 14, 4285-4295). Similar strains have also been created by N. Watanabe et al ((2012) *Antimicrob Agents Chemother* 56, 960-971).

Using gepinacin as a probe in medically relevant pathogens for which few genetic tools are available, new consequences of Gwt1 inhibition with important clinical implications have been uncovered. First, Gwt1 inhibition profoundly stresses the fungal ER leading to critical dependence on activation of compensatory response pathways. Such dependence creates new liabilities for the organism that might be targeted in future work to synergistically enhance the antifungal activity of Gwt1 inhibition. Second, the cell wall compromise caused by Gwt1 inhibition in fungi not only exposes β-glucan on the cell surface, but enhances recognition by antigen-presenting cells and activation of a pro-inflammatory immune response. These effects would be expected to enhance clearance by host defense mechanisms and decrease the emergence of resistance. In concert, these new insights further advance Gwt1 as a promising antifungal drug target and validate a useful new probe for studying the mechanisms by which inhibition of fungal GPI-anchor synthesis directly impairs viability and indirectly disrupts the complex process of pathogenesis.

Gepinacin Analogs

The following gepinacin analogs were tested for activity against Gwt1. Gepinacin, M3, CM2, CM4, CM6, CM7, CM8, and 857621-56-8 were available commercially. The compounds were tested using the "Antifungal Susceptibility Testing" protocol described above. Fungi tested are described in the "Fungal Strains" section above.
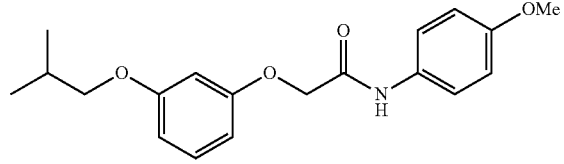
gepinacin (LW16)
M3
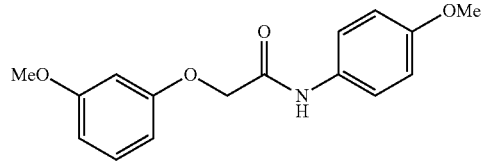
MAZ1839
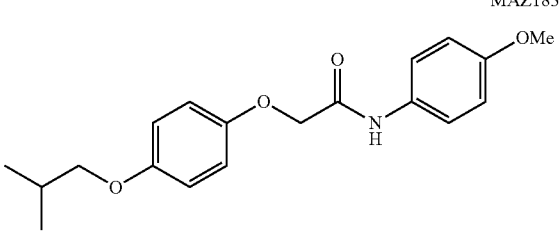
MAZ1843
MAZ1844
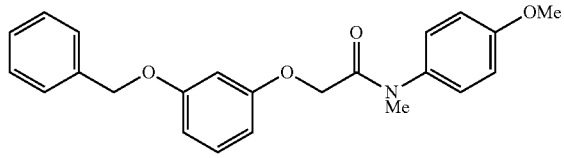
MAZ1857
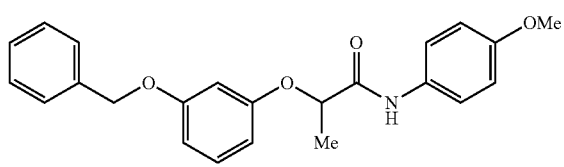
MAZ1859
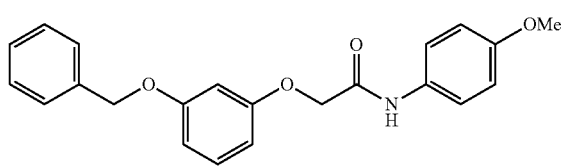
-continued
MAZ1854
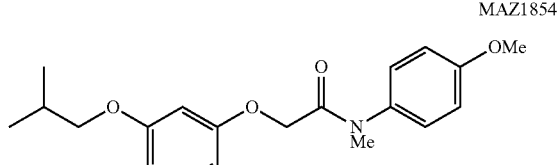
MAZ1855
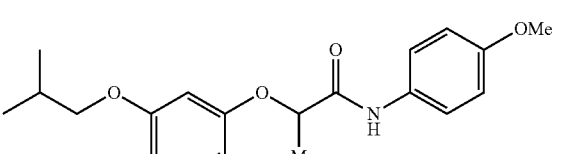
CM7
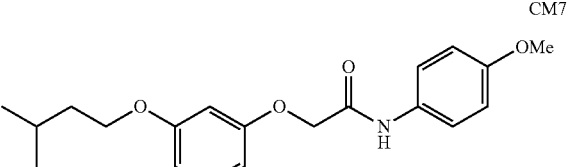
CM2
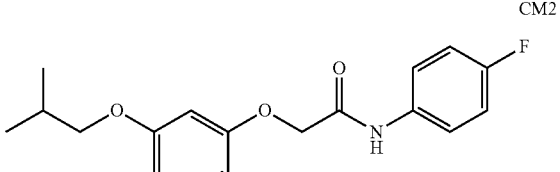
CM3
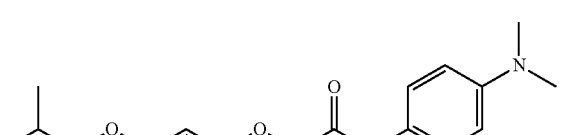
CM4
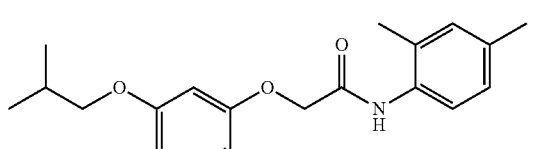
CM6
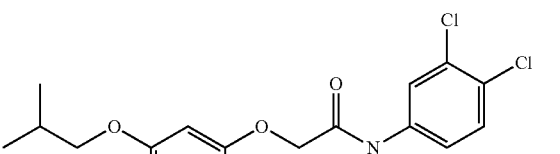
CM8
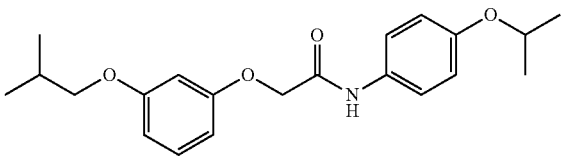

-continued 857621-56-8

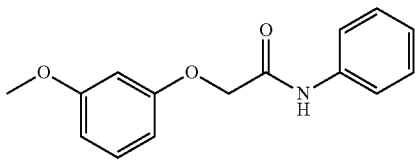

The data are shown in the table below (EC50 values in µM units).

| Wildtype S. cerevisiae BY4741 | | |
| --- | --- | --- |
| | Avg | Stdev |
| CM2 | 7.05 | 0.636396 |
| CM3 | 18.15 | 1.767767 |
| CM7 | 2.65 | 0.070711 |
| LW16 | 2.9 | 0.424264 |
| Screening strains | | |
| | Low Copy GWT1 | High Copy GWT1 |
| LW16 | 0.6 | 1.17 |
| CM2 | 1.16 | 3.07 |
| CM7 | 1.314 | 6.2 |
| MAZ1855 | 12.8 | 93.14 |
| LW16 | 0.29 | 1.89 |
| MAZ1857 | 176.9 | 267.6 |
| MAZ1859 | 4.9 | 7.2 |
| LW16 | 5.9 | 8.6 |

*This is set at a later time point

Compounds not listed in the table were inactive against Gwt1 at concentrations up to 40 µM. MAZ1844 was active against PigW but not Gwt1.

Protocol for *P. falciparum* (3D7) Drug Testing In Vitro

The stock culture was synchronized with 5% sorbitol, and then approximately 96 h later, the level of parasitemia was determined by light microscopy by counting of a minimum of 500 erythrocytes on a Giemsa-stained thin blood smear. Parasites were noted to be late-ring and early trophozoites, with no evident schizonts. The stock culture was then diluted with complete medium and normal human erythrocytes to a starting 4% hematocrit and 0.5% parasitemia.

90 µl of the cell suspension was put into each test well; in addition, several wells containing nonparasitized erythrocytes at 4% hematocrit served as reference controls. Stock solutions of the test drugs were prepared at a concentration of 10 mM in DMSO (chloroquine in water), serially diluted in complete medium, and dispensed into triplicate test wells to yield final concentrations ranging from 0 to 10 exp 5 M. Final well volumes were 100 ul for the fluorescence assay.

After 24 h of growth, 100 ul of SYBR Green I in lysis buffer (0.2 ul of SYBR Green/ml of lysis buffer) was added to each well, and the contents were mixed until no visible erythrocyte sediment remained. After 1 h of incubation in the dark at room temperature, fluorescence was measured with a fluorescence multiwell plate reader with excitation and emission wavelength bands centered at 485 and 530 nm, respectively.

Protocol for Inhibition Assay on *T. brucei Brucei* (427 Strain)

The assay is performed in 96 well white sterile plates for 24-28 hours. Each compound should be tested in duplicate. The controls in triplicate.

Reagents.

HMI-9 medium—Iscove's modification of DMEM (IMDM; Cell Gro) supplemented with 10% FBS, 10%, Serum plus (SAFC), 0.05 mM Bathocuproinesulfonate, 1.5 mM L-cysteine, 1 mM hypoxanthine, 0.2 mM β-mercaptoethanol, 0.16 mM thymidine 1 mM pyruvate (stock: 100 mM). Alamar Blue (Sigma)

Controls.

Medium alone, parasites alone, parasites+100 uM of Ionomycin

Protocol.

Compounds were thawed out. Parasites were spun for 10 min at 900 g (2 acceleration, 0 break). Meanwhile, 100 µL of HMI-9 medium were added per well in the 96 well white plate. Compounds were vortexed. 2 µL of each compound+ 98 µL of fresh medium were added to the first row, pipetted up and down to mix, and then transferred 100 µL to the next row in order to make serial dilutions. After centrifugation, medium was discarded by careful aspiration. Parasites were resuspended in warm medium and counted in Newbauer chamber. Parasites were diluted at $5\times10^6$ cells/ml ($5\times10^5$ cells/well) and plated 100 µL per well with multichannel pipette. After 22-24 hours, 20 µL of Alamar blue were added per well. Incubated at 37° C. for 4 hours, and read fluorescence at excitation 530 nm and 590 nm emission wavelengths.

Growth Inhibition Assay for HTS in 96 Well Plates

Notes.

Final volume per well for cells+parasites+compound was 200 µl. Final volume after adding substrate was 250 µl. Compounds were tested in duplicate or triplicate. The assay was performed in DMEM without Phenol red+2% FBS and 1% PSG to avoid interference of phenol red with the 590 nm absorbance reading.

Controls.

1. cells+parasites
2. cells without parasites
3. cells+parasites+Amphotericin B 4 µM (2.96 µL of 270 µM stock/well)
4. medium only Protocol for β-Gal Assay on *T. cruzi*

Protocol.

Parasites were harvested (*T. cruzi* expressing β-galactosidase) in 50 ml tubes and spin 7 min at 2500 rpm. Parasites were rinsed twice with DMEM without Phenol red+2% FBS and 1% PSG. Spun again at 2500 rpm for 7 min. Tubes were taken cautiously out of the centrifuge, placed them on a rack in the incubator to let trypomastigotes swim out of the pellet for 3-5 hours. In the meantime, 100 µL (50.000 NIH 3t3 cells) were plated per well with a multichannel pipette. Put back in incubator for 3 hours to allow cells to attach. Thawed compounds and added them at desired concentration. Add 100 µL of parasite in each well. Incubated for 4 days. Added 50 µL of substrate solution (500 M CPRG in PBS+0.5% NP404) per well of 96 well plate with multipipette. Incubated for 4 hours. Read absorbance at 590-595 nm Inhibition of Parasitic Growth

Figure 19:
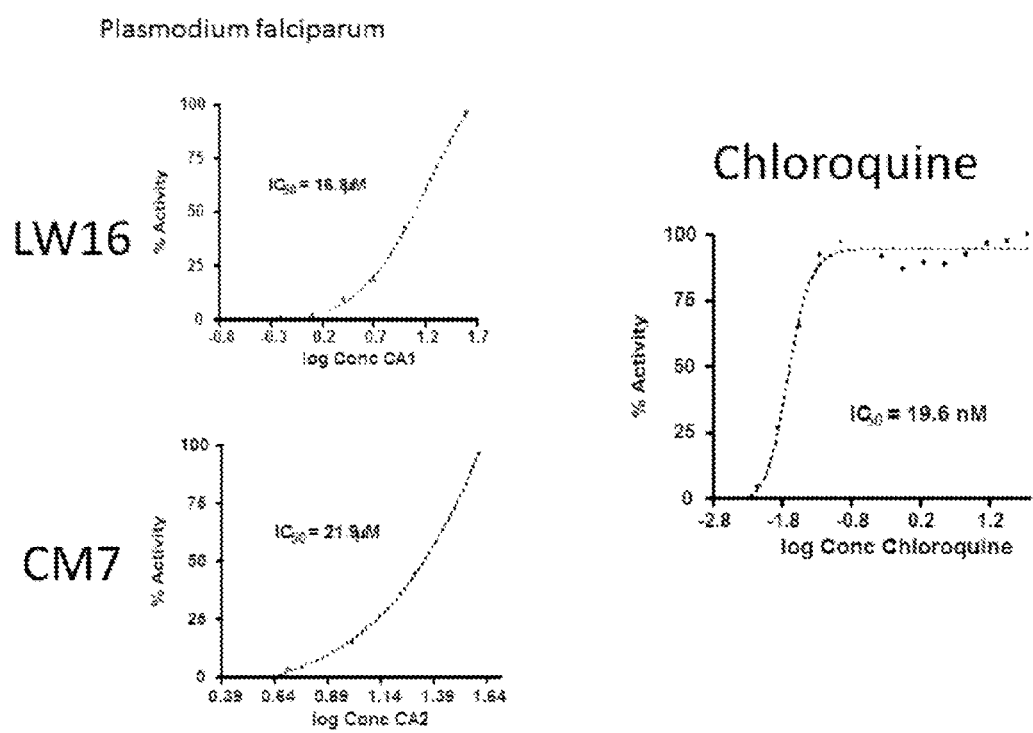
FIG. 19 shows *P. falciparum* data for chloroquine, gepinacin, and CM7.
Figure 20:
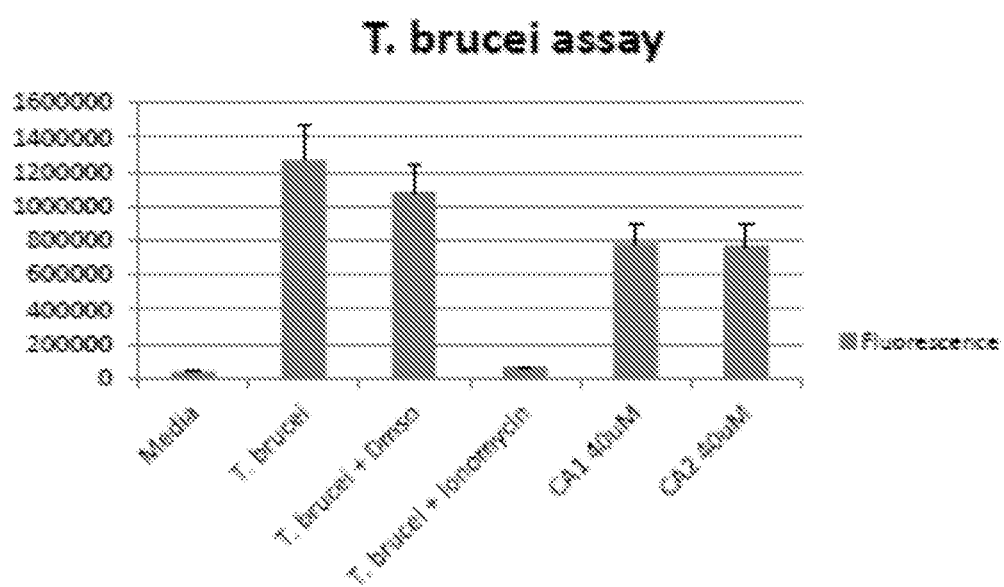
FIG. 20 shows *T. brucei* data for ionomycin, gepinacin, and CM7.
Figure 21:
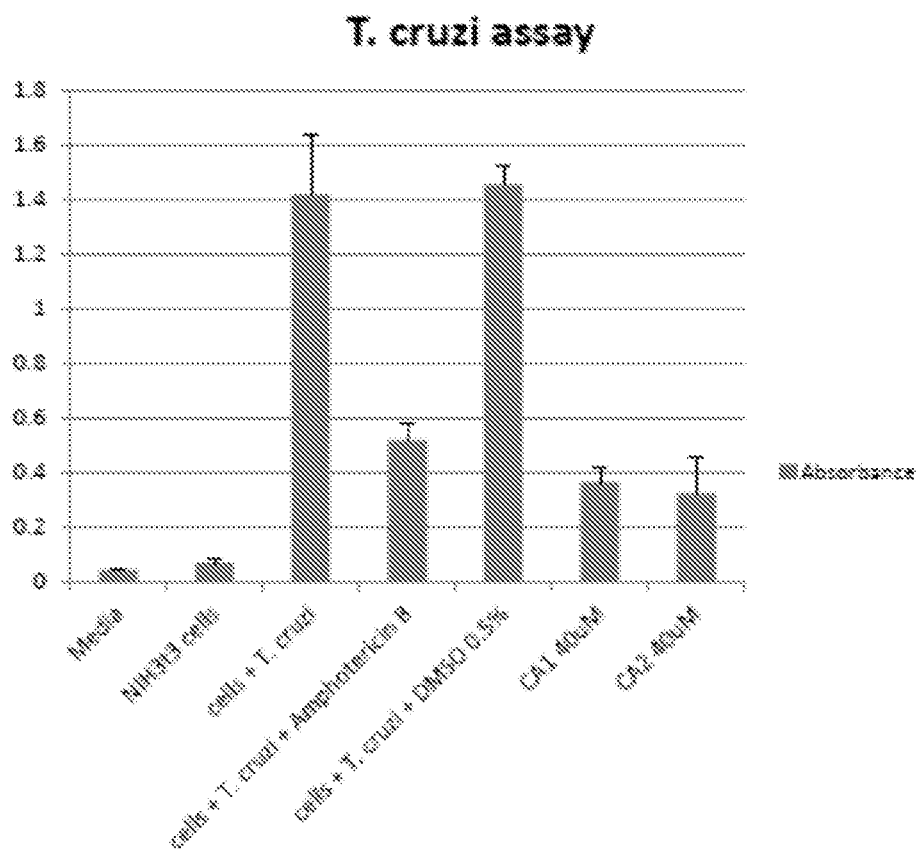
FIG. 21 shows *T. cruzi* data for amphotericin B, gepinacin, and CM7.

*P. falciparum* data for gepinacin, CM7, and chloroquine are shown in FIG. 19. *T. brucei* data for ionomycin, gepinacin, and CM7 are shown in FIG. 20. *T. cruzi* data for amphotericin B, gepinacin, and CM7 are shown in FIG. 21.

Determination of the Compounds' Specificity for Fungal Genes

An *S. cerevesiae* strain was generated in which the endogenous Gwt1 gene was deleted. Plasmids (either high copy or low copy) with either *S. cerevesiae* or human Gwt1 were introduced to produce strains bearing such plasmids expressing either *S. cerevesiae* or human Gwt1 from a constitutive promoter. Yeast strains were cultured in liquid media in the presence of indicated compounds. Shown in FIGS. 22A-D show the effect of the indicated compounds on growth (assessed by $OD_{600}$) and viability (assessed using Bactiter Glo) of the yeast strain with high copy or low copy plasmid containing *S. cerevesiae* Gwt1. The compounds had no effect on strains with the human Gwt1, thus showing the compounds' sensitivity for the fungal (yeast) Gwt1 gene.

EQUIVALENTS AND SCOPE

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of formula I:

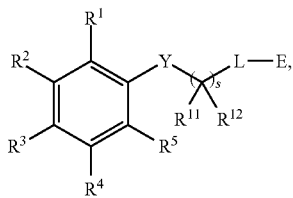

or a pharmaceutically acceptable salt, solvate, hydrate, tautomer, enantiomer, or diastereomer thereof, wherein:

each one of $R^1$ and $R^5$ is hydrogen;

each one of $R^3$ and $R^4$ is independently selected from the group consisting of hydrogen, halo, —CN, —NO$_2$, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)OR$^A$, —NR$^B$C(=O)OR$^A$, —OC(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$;

each occurrence of $R^A$ is independently hydrogen, optionally substituted alkyl, optionally substituted alkenyl, optionally substituted alkynyl, optionally substituted carbocyclyl, optionally substituted heterocyclyl, optionally substituted aryl, or optionally substituted heteroaryl; and each occurrence of $R^B$ is independently hydrogen, optionally substituted alkyl, optionally substituted alkenyl, optionally substituted alkynyl, optionally substituted carbocyclyl, optionally substituted heterocyclyl, optionally substituted aryl, optionally substituted heteroaryl, or an amino protecting group, or two $R^B$ groups are joined to form an optionally substituted heterocyclic ring;

$R^2$ is —O—R$^x$;

$R^x$ is optionally substituted $C_{3-8}$ alkyl, optionally substituted alkenyl, optionally substituted alkynyl, optionally substituted carbocyclyl, optionally substituted heterocyclyl, optionally substituted aryl, optionally substituted heteroaryl, optionally substituted aralkyl, or optionally substituted heteroaralkyl;

or $R^x$ and $R^3$ are taken together with their intervening atoms to form an optionally substituted heterocyclic ring;

Y is —O— or —S—;

each instance of $R^{11}$ is independently hydrogen or optionally substituted alkyl;

each instance of $R^{12}$ is independently hydrogen or optionally substituted alkyl;

L is —C(=O)NR$^{13}$—;

$R^{13}$ is hydrogen or $C_{1-6}$ alkyl;

E is of the formula

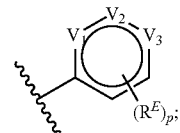

s is 1, 2, 3, 4, 5, or 6;

each instance of $V_1$, $V_2$, and $V_3$ is independently N or C, provided that at least one of $V_1$, $V_2$, and $V_3$ is N;

each instance of $R^E$ is independently selected from the group consisting of hydrogen, halo, —CN, —NO$_2$, halogen, optionally substituted alkyl, optionally substituted alkenyl, optionally substituted alkynyl, optionally substituted carbocyclyl, optionally substituted heterocyclyl, optionally substituted aryl, optionally substituted heteroaryl, —OR$^A$, —N(R$^B$)$_2$, —SR$^A$, —C(=O)R$^A$, —C(=O)OR$^A$, —C(=O)SR$^A$, —C(=O)N(R$^B$)$_2$, —OC(=O)R$^A$, —NR$^B$C(=O)R$^A$, —NR$^B$C(=O)N(R$^B$)$_2$, —OC(=O)OR$^A$, —NR$^B$C(=O)OR$^A$, —OC(=O)N(R$^B$)$_2$, —SC(=O)R$^A$, —C(=NR$^B$)R$^A$, —C(=NR$^B$)N(R$^B$)$_2$, —NR$^B$C(=NR$^B$)R$^B$, —C(=S)R$^A$, —C(=S)N(R$^B$)$_2$, —NR$^B$C(=S)R$^A$, —S(=O)R$^A$, —SO$_2$R$^A$, —NR$^B$SO$_2$R$^A$, and —SO$_2$N(R$^B$)$_2$; and p is 0, 1, 2, 3, or 4, as valency permits.

2. The compound of claim 1, wherein the compound is of formula III-a:

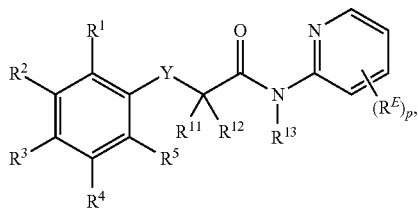

III-a or a pharmaceutically acceptable salt, solvate, hydrate, tautomer, enantiomer, or diastereomer thereof.

3. The compound of claim 1, wherein the compound is of formula V:

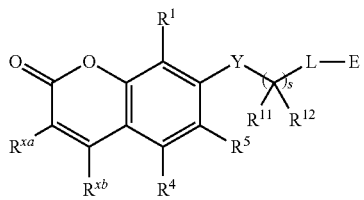

V or a pharmaceutically acceptable salt, solvate, hydrate, tautomer, enantiomer, or diastereomer thereof, wherein:
each of $R^{xa}$ and $R^{xb}$ is independently hydrogen, halogen, or optionally substituted alkyl.

4. The compound of claim 1, wherein Y is —O—.
5. The compound of claim 1, wherein at least one of $R^{11}$ and $R^{12}$ is hydrogen.
6. The compound of claim 1, wherein $R^{11}$ and $R^{12}$ are hydrogen.
7. The compound of claim 1, wherein $R^{11}$ is methyl and $R^{12}$ is hydrogen.
8. The compound of claim 1, wherein L is —C(=O)NH—.
9. The compound of claim 1, wherein the compound is of the formula:

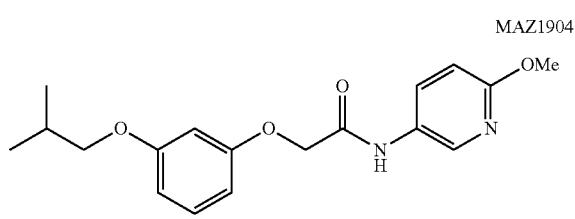

MAZ1904 or

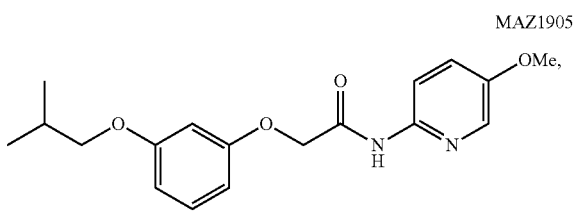

MAZ1905 or a pharmaceutically acceptable salt, solvate, hydrate, tautomer, enantiomer, or diastereomer thereof.

10. The compound of claim 1, wherein the compound is of formula III-b:

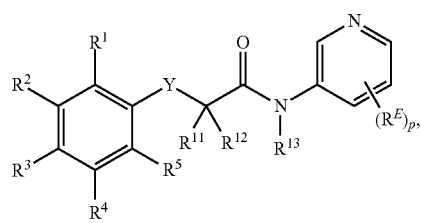

III-b or a pharmaceutically acceptable salt, solvate, hydrate, tautomer, enantiomer, or diastereomer thereof.

11. The compound of claim 1, wherein the compound is of formula III-b1:

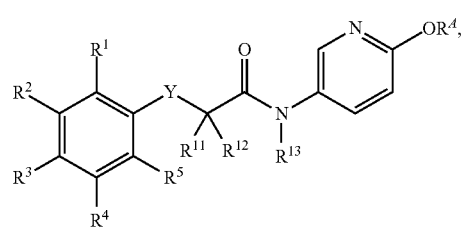

III-b1 or a pharmaceutically acceptable salt, solvate, hydrate, tautomer, enantiomer, or diastereomer thereof.

12. The compound of claim 11, wherein Y is —O—.
13. The compound of claim 11, wherein each one of $R^3$ and $R^4$ is hydrogen.
14. The compound of claim 11, wherein $R^X$ is optionally substituted $C_{3-8}$ alkyl.
15. The compound of claim 11, wherein $R^A$ is optionally substituted $C_{1-6}$ alkyl.
16. The compound of claim 1, wherein the compound is of the formula:

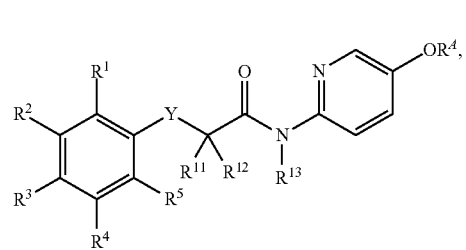

III-a1 or a pharmaceutically acceptable salt, solvate, hydrate, tautomer, enantiomer, or diastereomer thereof.

17. The compound of claim 1, wherein $R^3$ is halogen, optionally substituted $C_{1-6}$ alkyl, or —$OR^A$.
18. The compound of claim 1, wherein $R^4$ is halogen or optionally substituted $C_{1-6}$ alkyl.
19. The compound of claim 1, wherein $R^3$ is hydrogen.
20. The compound of claim 1, wherein $R^4$ is hydrogen.
21. The compound of claim 1, wherein $R^X$ is optionally substituted $C_{3-8}$ alkyl.

22. The compound of claim 1, wherein $R^X$ is optionally substituted aryl.

23. The compound of claim 1, wherein $R^X$ is optionally substituted heteroaryl.

24. The compound of claim 1, wherein $R^X$ is optionally substituted aralkyl.

25. The compound of claim 1, wherein $R^X$ and $R^3$ are taken together with their intervening atoms to form an optionally substituted heterocyclic ring.

26. The compound of claim 1, wherein s is 1.

27. The compound of claim 1, wherein $V_1$ is N, and $V_2$ and $V_3$ are C.

28. The compound of claim 1, wherein $V_2$ is N, and $V_1$ and $V_3$ are C.

29. The compound of claim 1, wherein $V_3$ is N, and $V_1$ and $V_2$ are C.

30. The compound of claim 1, wherein the compound is of formula 111-c:

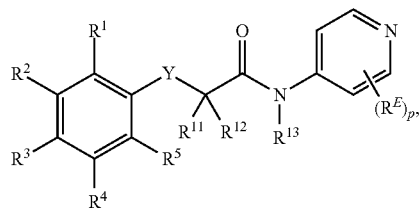

III-c or a pharmaceutically acceptable salt, solvate, hydrate, tautomer, enantiomer, or diastereomer thereof.

31. A pharmaceutical composition comprising a compound of claim 1, and a pharmaceutically acceptable excipient.

32. A method of inhibiting Gwt1, or a mutant or variant thereof, comprising contacting the Gwt1, or mutant or variant thereof, with an effective amount of a compound of claim 1.

33. A method of inhibiting fungal growth comprising contacting a fungus with an effective amount of a compound of claim 1.

34. The method of claim 33, wherein the fungus is in a subject, and a therapeutically effective amount of the compound is administered to the subject.

35. The method of claim 33, wherein the fungus is *Candida albicans, Aspergillus fumigatus, Candida glabrata*, or *Aspergillus terreus*.

36. A method of inhibiting parasitic growth comprising contacting a parasite with an effective amount of a compound of claim 1.

37. The method of claim 36, wherein the parasite is in a subject, and a therapeutically effective amount of the compound is administered to the subject.

38. The method of claim 36, wherein the parasite is *Plasmodium falciparum, Trypanosome brucei*, or *Trypanosome cruzi*.

* * * * *

SEQUENCE LISTING

<160> NUMBER OF SEQ ID NOS: 1

<210> SEQ ID NO 1
<211> LENGTH: 203
<212> TYPE: PRT
<213> ORGANISM: Saccharomyces cerevisiae

<400> SEQUENCE: 1

```
Met Ala Ser Phe Ala Thr Lys Glu Val Ile Ala Cys Phe Leu Phe Phe
1               5                   10                  15

Ser Ala Ser Ala Gly Asn Val Leu Leu Pro Ala Tyr Gly Arg Arg Cys
            20                  25                  30

Phe Phe Glu Asp Leu Ser Lys Gly Asp Glu Leu Ser Ile Ser Phe Gln
        35                  40                  45

Phe Gly Asp Arg Asn Pro Gln Ser Ser Ser Gln Leu Thr Gly Asp Phe
    50                  55                  60

Ile Ile Tyr Gly Pro Glu Arg His Glu Val Leu Lys Thr Val Arg Asp
65                  70                  75                  80

Thr Ser His Gly Glu Ile Thr Leu Ser Ala Pro Tyr Lys Gly His Phe
                85                  90                  95

Gln Tyr Cys Phe Leu Asn Glu Asn Thr Gly Ile Glu Thr Lys Asp Val
```

```
                  100             105                 110
Thr Phe Asn Ile His Gly Val Val Tyr Val Asp Leu Asp Asp Pro Asn
            115                 120              125

Thr Asn Thr Leu Asp Ser Ala Val Arg Lys Leu Ser Lys Leu Thr Arg
        130             135              140

Glu Val Lys Asp Glu Gln Ser Tyr Ile Val Ile Arg Glu Arg Thr His
145             150                 155              160

Arg Asn Thr Ala Glu Ser Thr Asn Asp Arg Val Lys Trp Trp Ser Ile
                165         170              175

Phe Gln Leu Gly Val Val Ile Ala Asn Ser Leu Phe Gln Ile Tyr Tyr
            180             185              190

Leu Arg Arg Phe Phe Glu Val Thr Ser Leu Val
        195             200
```